United States Patent [19]
Good

[11] Patent Number: 6,099,457
[45] Date of Patent: Aug. 8, 2000

[54] ENDOCURIETHERAPY

[75] Inventor: Roger Good, Omaha, Nebr.

[73] Assignee: EndoTech, Inc., Spokane, Wash.

[21] Appl. No.: 07/741,038

[22] Filed: Aug. 6, 1991

Related U.S. Application Data

[63] Continuation-in-part of application No. 07/565,714, Aug. 13, 1990, Pat. No. 5,342,283.
[51] Int. Cl.⁷ ....................................................... A61N 5/00
[52] U.S. Cl. .................................................................. 600/8
[58] Field of Search ............................................. 600/1–8

[56] References Cited

U.S. PATENT DOCUMENTS

| | | | |
|---|---|---|---|
| 4,702,228 | 10/1987 | Russell, Jr. et al. | 600/8 |
| 4,754,745 | 7/1988 | Horowitz | 600/8 |
| 4,994,013 | 2/1991 | Suthanthiran | 600/8 |

*Primary Examiner*—John P. Lacyk
*Attorney, Agent, or Firm*—Vincent L. Carney

[57] ABSTRACT

To provide versatile radioactive implants and methods of radiation therapy, plating methods such sputtering, as are used to coat single elements such as microspheres, wires and ribbons with radioactive metals, protective layers and identification layers. The resulting solid, radioactive, multilayered seamless elements are implanted individually or combined in intercavity applicators, with fabrics and in ribbons. Because they have selected half-lives and intensities, they provide flexibility in treatment, permitting low intensity or high intensity treatment. using temporary or permanent implants and implants with high intensity or low intensity or controured intensity to permit different therapies.

16 Claims, 17 Drawing Sheets

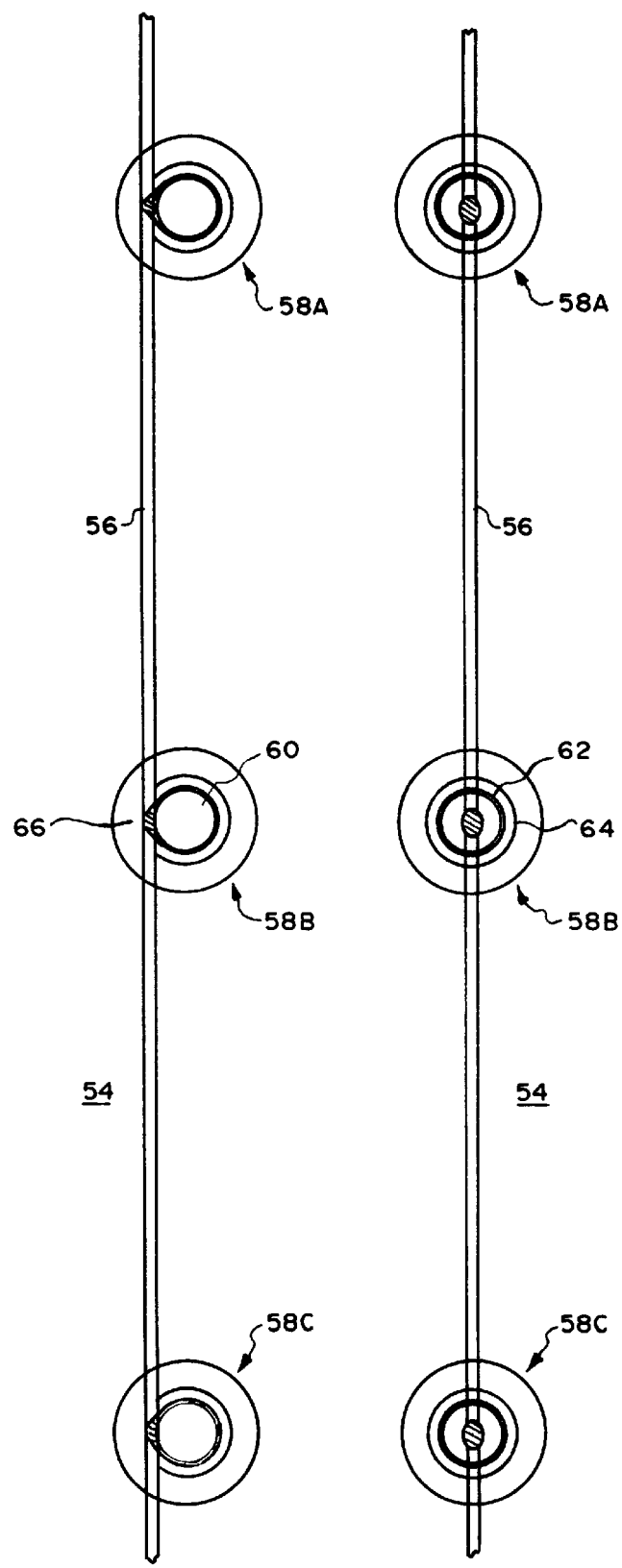

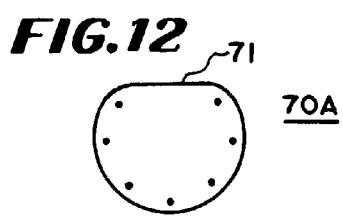
FIG.12
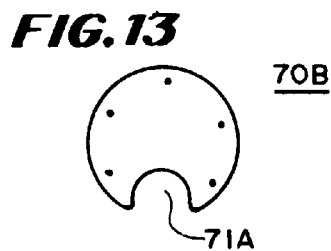
FIG.13
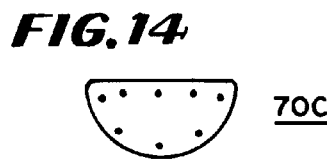
FIG.14
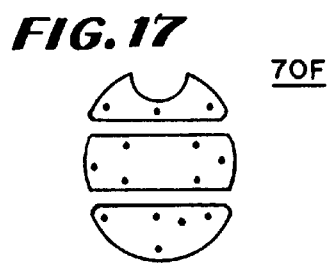
FIG.17
FIG.15
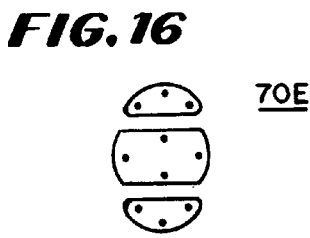
FIG.16
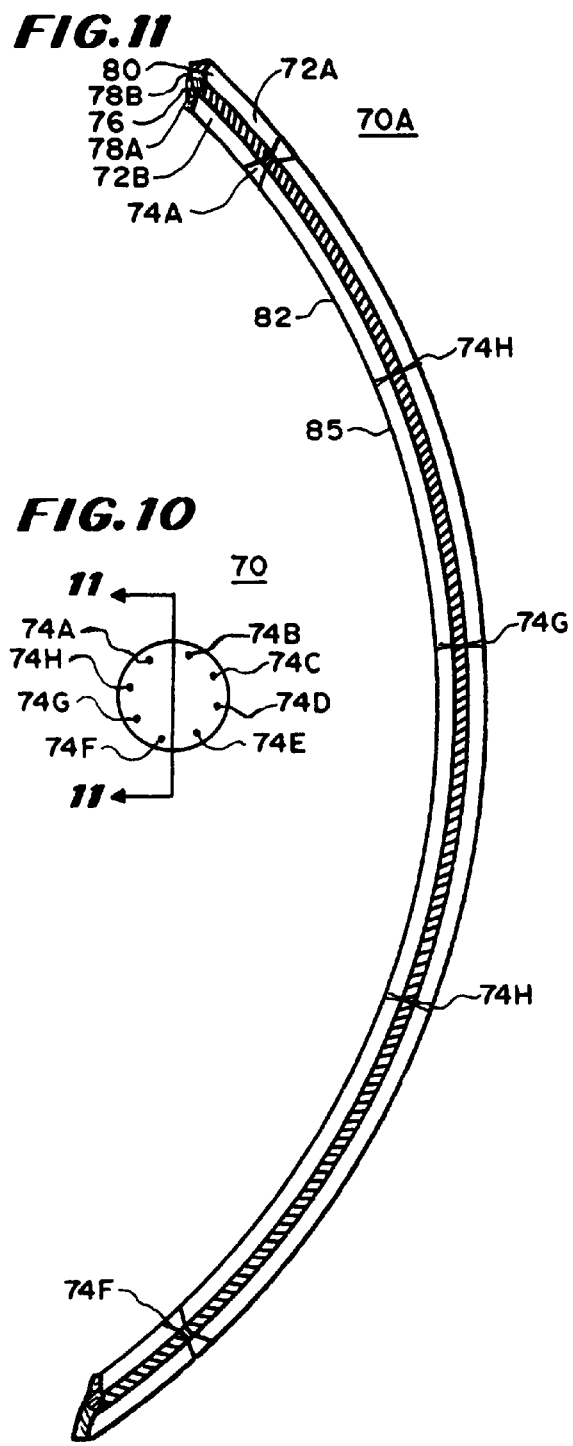
FIG.11
FIG.10

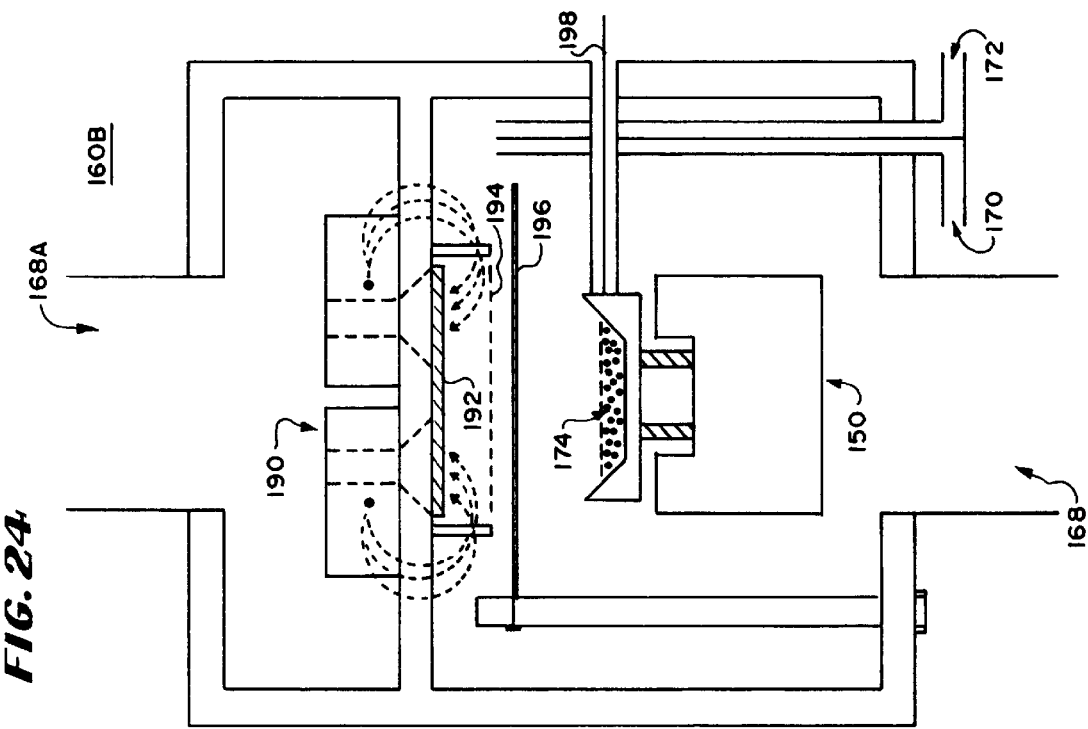
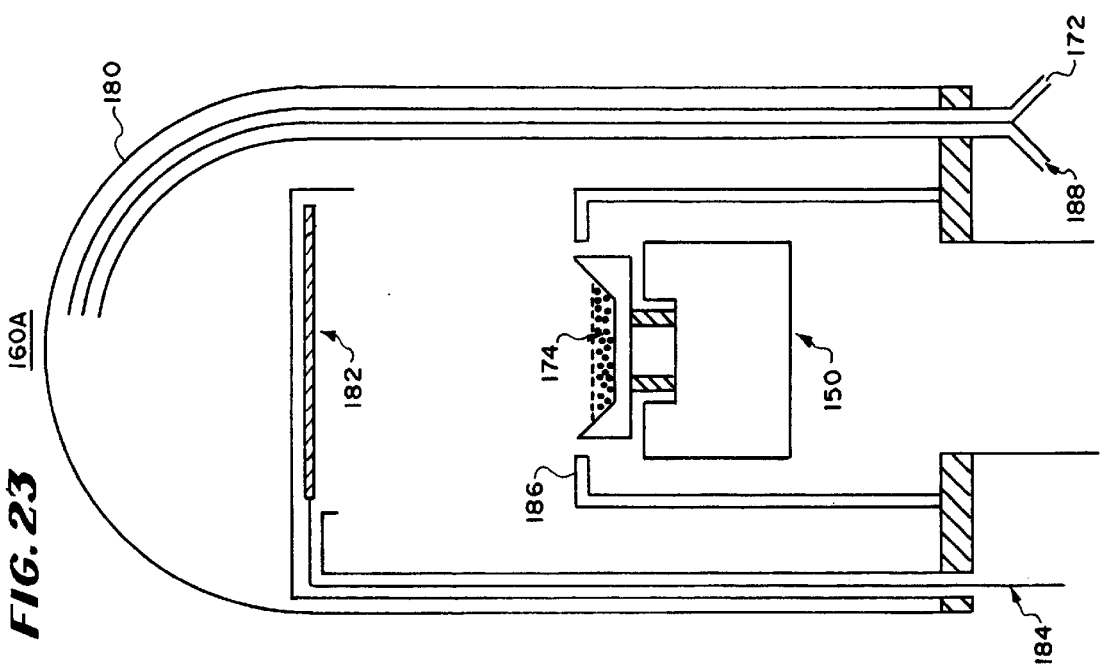

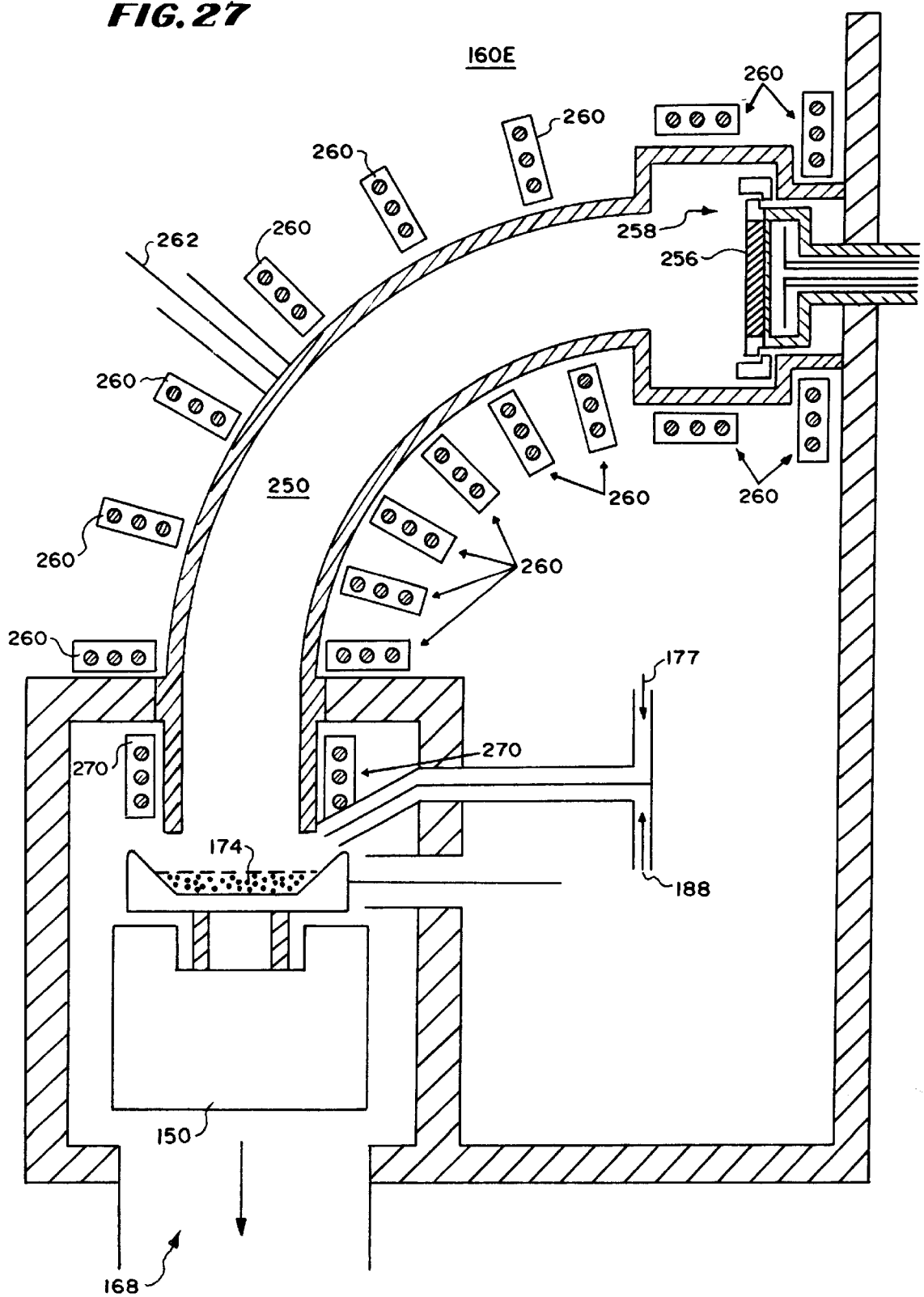

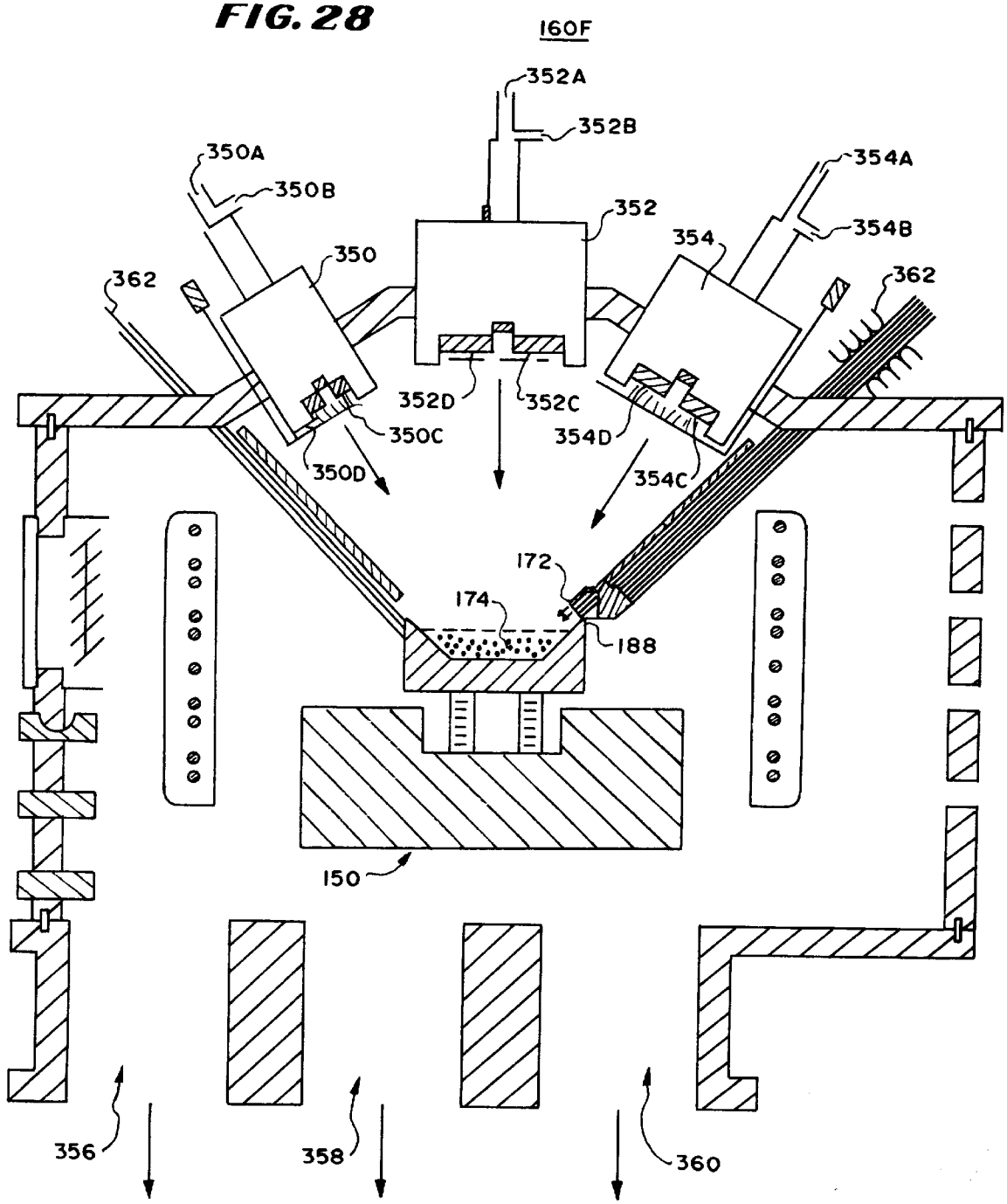

ENDOCURIETHERAPY

REFERENCE TO RELATED APPLICATIONS

This application is a continuation-in-part application of U.S. application Ser. No. 07/565,714 for ENIDOCURIETHERAPY filed by Roger P. Good on Aug. 13, 1990 now U.S. Pat. No. 5,342,283.

BACKGROUND OF THE INVENTION

This invention relates to radioactive implants, methods of making them and methods of using them.

It is known to use external beam supervoltage or megavoltage conventional fractionated radiation therapy to treat subclinical microscopic metastases in surgically undisturbed lymph node chains and to sterilize the postoperative tumor bed after the tumor is grossly excised. The uses of external beam radiation techniques have a disadvantage that they are not able to safely treat solid tumors because the solid tumors require an intensity of radiation that is harmful to the surrounding normal tissue.

It is also known to implant radioactive sources directly into solid tumors for the destruction of the tumors in a therapy referred to as brachytherapy (short-range therapy). This therapy permits the application of larger does of radiation.

In the prior art brachytherapy, the sources are generally implanted for short periods of time and generally are sources of high radiation intensity. For example, radium needles and iridium-192 ribbons have been implanted into tumors (interstitial brachytherapy) or radium-226 capsules and cesium-1.37 capsules have been placed into body cavities such as the uterus (intracavitary brachytherapy).

The prior art interstitial brachytherapy treatment using radium needles has several disadvantages, such as for example: (1) dosimetry is difficult and imprecise; (2) local failures are caused, mainly by the large size of the radium needles (approximately the size of a lumber nail); (3) it is difficult to implant an adequate number of the needles uniformly throughout a tumor to produce homogeneous irradiation because they are large sources; and (4) the needles can only be left in place temporarily, and must be surgically removed.

It is known to implant iodine seeds temporarily or permanently. The prior art iodine seed consists of the radionuclide adsorbed onto a carrier which is placed into a metal tube that is welded shut. It has the disadvantages of: (1) being relatively large to be safely implanted in large numbers in the human body; and (2) due to its construction, producing inhomogeneous radiation.

The prior art iridium seeds in ribbon consist of solid iridium wire cut into pieces and placed in plastic tubing, which is then implanted into accessible tissues temporarily for several days. These seeds work well, but because they must be removed, their application is limited to a few accessible body sites. Also, they only come in one energy.

The prior art radium-226 intracavitary sources and cesium sources consist of metal cylinders containing radium salts or cesium. The have several disadvantages, such as for example: (1) dosimetry is difficult and imprecise; (2) they are bulky and difficult to use; (3) it is difficult to implant or otherwise insert an adequate number of the cylinders in the proper locations to produce homogeneous irradiation because they are large sources; (4) the cylinders can only he left in place temporarily, and under some circumstances, must to be surgically removed; and (5) general anesthesia is required to dilate the cervix sufficiently to place a source in the uterus.

The applications of brachytherapy are still severely limited by the unavailability of a wide range of implantable radioactive sources that have a wide range of gamma energies (radiation energy is related to the volume irradiated) and varying half-lives (radionuclide half-life affects tumor dose rate, radiobiology, and normal tissue effects). Also the limited number of sources currently available are still physically unsatisfactory in their construction. There are few low energy limited lifetime radioactive seeds such as gold-198 and iodine-125 seeds that may be permanently implanted into solid cancers.

It is also known to apply heat to tumors by implanting metals that may be heated by radio frequency radiation and to move heatable or radioactive members about magnetically for positioning them without excessive surgery. This is especially significant in the treatment of highly vascular tumors. The existing hyperthermia radio frequency treatment is not well adapted for easy combination with endocurietherapy.

SUMMARY OF THE INVENTION

Accordingly, it is an object of the invention to provide novel radioactive implants.

It is a still further object of the invention to provide a novel electron-producing beta-seed.

It is a still further object of the invention to provide a perfectly spherical tantalum, tungsten, gold, platinum casing or compound tungsten carbide, tantalum carbide casing over a radioactive microspherical substrate when the radioactive material produces high energy gamma rays.

It is a still further object of the invention to provide a perfectly spherical titanium, hafnium or zirconium metal casing or a compound casing of titanium carbide, titanium nitride, titanium conbonitride, hafnium nitride or zirconium nitride over a radioactive microspherical substrate when the radioactive material produces low energy gamma rays.

It is a still further object of the invention to provide a perfectly spherical diamond casing over a radioactive microsphere when the radioactive material produces beta rays.

It is still further object of the invention to produce a novel low-energy permanent multilayered radioactive microsphere.

It is a still further object of the invention to provide a novel tissue-compatible (absorbable and non-absorbable) surgical fabric that contains multiple radioactive seeds to facilitate rapid implantation of a large number of radioactive seeds.

It is a still further object of the invention to provide a novel ribbon containing multiple low energy permanent multilayered radioactive microspheres.

It is a still further object of the invention to provide a novel multilayered low energy permanent or temporary radioactive wire that may be permanently or temporarily implanted into human tissues and that safely delivers low energy.

It is a still further object of the invention to provide a novel implant that safely delivers energy at levels less than or equal to 100 KeV average gamma energy to tumors at a low rate in less than 130 days to produce tumoricidal radiation doses that are 2.3 to 5.7 times higher than the maximum doses permissible with reasonable safety by modern megavoltage external beam radiation therapy techniques.

It is a still further object of this invention to produce a radioactive seed which has the clinical result of reducing the complication rate of treatment while increasing the local cure rate by allowing safe delivery of very high radiation doses to solid human tumors.

It is still further object of the invention to produce an improved radioactive seed, ribbon containing multiple seeds, or radioactive wire which may be permanently implanted into human tissues and safely deliver high energy (greater than 100 KeV average gamma energy) tumor irradiation at an average dose rate less than 1.50 Gy/hour (Gray/hour-one Gray is equal to 100 rad) in less than 15 to 20 days.

It is a still further object of the invention to provide a novel technique for making an improved radioactive seed, seed ribbon, or radioactive wire which may be temporarily implanted into human tissues by after-loading tubes or by implanting interstial needles.

It is a still further object of the invention to produce a novel multilayered radioactive microsphere, ribbon microsphere, or multilayered radioactive wire, which emits electrons or beta particles and have casings which are substantially transparent to electrons.

It is a still further object of the invention to provide a radioactive seed having a shape that is spherical rather than cylindrical to make it less likely to jam in an auto-feeding tissue implantation gun.

It is a still further object of the invention to increase the clinical utility and safety of the radioactive seed by making it significantly smaller in diameter to permit tissue implantation with thinner gauge needles.

It is a still further object of the invention to improve upon the uniformity of the radioactive coat used in radioactive seed production.

It is a still further object of the invention to produce a radioactive seed which contains multiple coats which have specialized purposes.

It is a still further object of the invention to produce a radioactive seed which contains a diffusion barrier coat over the radionuclide layer.

It is a still further object of the invention to produce a radioactive seed which contains a coat that enables visualization of the seed in tissue such as by magnetic resonance imaging (NMR, MR) or X-ray or single positron resonance (SPFCT) or positron emitting tomography (PET) or the like.

It is a still further object of the invention to produce radioactive seeds that contain different magnetic resonance imaging marker coat to enable separate individual identification of one type of seed from another type of seed when seeds containing different radionuclides are implanted into the same tumor.

It is a still further object of the invention to produce an outermost seed coat which reduces friction, adds coloring for seed type identification, increases hardness and durability, and increases tissue compatibility and corrosion resistance.

It is a still further object of the invention to produce a more miniaturized intracavitary source that may be placed into the uterus without endocervical dilation or into the bladder with minimal trauma to the urethra and is available in a wide range of energies and isotopes.

It is a still further object of the invention to provide a radioactive seed that can be raised to a selected temperature by remotely radiated energy for hyperthermia.

It is a still further object of the invention to provide a radioactive seed that can be moved by remotely originated radiant energy.

It is a further object of the invention to provide novel techniques for manufacturing radioactive implants.

It is a still further object of the invention to provide techniques for manufacture of radioactive seeds containing a wide variety of radionuclides with different energies and half-lives.

It is a still further object of the invention to provide techniques for manufacturing a wide variety of radionuclides including those useful for permanent implantation into human tissues, those useful for temporary removable interstitial needle or ribbon implantation into human tissues, and those useful for temporary intracavitary irradiation.

It is a still further object of the invention to mass manufacture microspherical seeds less than 0.40 millimeter in diameter that may contain a therapeutic amount of radioactivity, a hard tissue-compatible protective coat, and several special purpose coats.

It is a still further object of the invention to provide a novel technique for manufacture of multiple radioactive seeds connected by a ribbon or wire to facilitate rapid implantation of multiple seeds.

It is still further object of the invention to provide a novel technique for manufacture of multilayered radioactive wires that contain a wide variety of different radionuclides for use in temporary removable tumor implants.

It is a still further object of the invention to manufacture a novel small-diameter (less than one millimeter) high-activity intracavitary source using any of a variety of different radionuclides.

It is a still further object of the invention to present a novel method for incorporation of a radionuclide into a seed during manufacture of the seed.

It is a still further object of the invention to provide a novel method for incorporation of a nonradioactive elemental isotope into a seed during manufacture of a seed that will later form the desired radioactive isotope when the finished seed is bombarded with neutrons.

It is a still further object of the invention to provide a method for making a perfectly spherical titanium casing over a radioactive microspherical substrate when the radioactive material produces low energy gamma rays.

It is a still further object of the invention to provide a less expensive seed by eliminating the need for human or mechanical assembly of separate parts and welding of individual seeds.

It is a still further object of the invention to provide an effective low cost method for large-scale mass-manufacture of high quality radioactive seeds for use in implantation of human tissues and to make the seeds readily available for use in large numbers of patients on a daily basis.

It is still further object of the invention to provide means of modified manufacturing processes which allows great versatility in manufacturing seeds of a variety of designs containing different combinations of types of radionuclides, metal and alloy coats, and elemental nonmetallic as well as compound hard coats.

It is a still further object of the invention to introduce a versatility of manufacturing process that permit manufacture of improved seeds which have varied physical characteristics including different average gamma radiation energies and different average lifetimes.

It is a still further object of the invention to provide a combination of manufacturing techniques that permit optimally matched seeds for the physical location and radiobiology of the tumor type or cancerous tissue they are designed to destroy.

It is a still further object of the invention to provide novel method for production of radioactive microspheres, ribbon microspheres or wires in which the radioactive component is incorporated into the microsphere by the reaction of an excited radionuclide gas with a target material produced by reactive coating techniques.

It is a still further object of the invention to provide a novel method for production of radioactive microspheres, ribbon microspheres, or wires in which the radioactive component is incorporated into the microsphere by sputtering, laser ablation, cathodic arc plasma deposition or curvilinear cathodic arc plasma deposition from a target material consisting of a radioactive dielectric compound material or a radioactive metal.

It is a still further object of the invention to provide novel techniques for using radioactive implants.

It is a still further object of the invention to provide a novel technique for eliminating the radiation dose anisotropy problems characteristic of the tungsten end-welded cylindrical radioactive seeds.

It is a still further object of the invention to reduce the danger of radioactive contamination of the hospital environment.

It is a still further object of the invention to reduce the danger of case rupture of the radioactive seed by eliminating the free space between the radioactive component and the casing.

It is a still further object of the invention to reduce the danger of radiation exposure to personnel involved in seed assembly.

A still further object of the invention is to produce a radioactive seed which has the clinical result of reducing the complication rate of treatment while increasing the local cure rate by allowing safe delivery of very high radiation doses to solid human tumors.

It is a still further object of the invention to provide a novel therapy for necrosis of tumors.

It is a still further object of the invention to provide a novel therapy which combines low dose continuous radiation with higher dosage radiation for the destruction of tumors.

It is a still further object of the invention to provide a novel therapy for the incorporation of low energy implants into a tumor with externally applied high energy treatment to destroy a tumor.

It is a still further object of the invention to provide a novel therapy in which cancer cells are biased toward a sensitive state and then irradiated for a short period of time while in the sensitive state.

It is a still further object of the invention to produce a radioactive seed which has the clinical result of serving as a radiation sensitizer when implanted prior to administration of conventional external-beam radiation therapy and which delivers continuous low dose rate radiation to block tumor cells in the most radiation sensitive portions of their cell cycle.

According to the above and further objects of the invention, a one-piece solid spherical seamless multilayered radioactive seed, herein sometimes referred to as a multilayered radioactive microsphere includes a spherical radioactive thin layer with a therapeutic amount of activity. The spherical seed has several desirable characteristics such as for example: (1) its contents may provide up to 1000 millicuries of activity and a completely spherical photon fluence without significant anisotropy; and (2) there is no free space between the radioactive component and the casing. in a preferred embodiment, it includes a microspherical central marker, a spherical radioactive thin coat containing a therapeutic amount of activity, a spherical diffusion barrier coat, an optional special purpose spherical coating designed to enhance diagnositc imaging, a thick spherical (up to 0.10 mm) protective coating containing the inner coats, and an optional thin outermost special-purpose coat in the order listed. The multilayered radioactive microsphere contains: (1) no free spaces or cavities; and (2) no end-welds. The central marker or special coat for imaging may be selected for X-ray, PET, SPECT or MR or any other type of imaging.

The multilayer radioactive micropsphere radionuclide is selected for the desired purpose. For example, for a first group of purposes, the radionuclide has a weighted average gamma energy of less than 100 KeV, with a half-life of less than 130 days. This multilayer radioactive micropsphere is referred to as a low energy permanent multilayered radioactive microsphere for permanent interstitial implantation into human tumor tissues. The corresponding multilayer radioactive microsphere with a gamma energy greater than 100 KeV is referred to as a high energy permanent multilayered radioactive microsphere for permanent interstitial implantation into human tumor tissues. Preferably, its half life is less than 15 to 20 days.

For a second group of purposes, the radionuclide has a weighted average gamma energy greater than or equal to 100 KeV, with a half-life of greater than 15 to 20 days, or an average energy less than 100 KeV and a half-life of greater than 130 days. This multilayered radioactive microsphere is referred to as a temporary removable multilayered radioactive microsphere for temporary removable interstitial implantation into human tumor tissues.

For a third group of purposes, the radionuclide emits a high energy electron particle without significant high-energy gamma-ray component. This multilayer radioactive microsphere is referred to as an electron-producing or beta multilayered radioactive microsphere for permanent or temporary removable interstitial implantation into human tumor tissues.

The shape, size and packaging of the multilayered radioactive seeds are appropriate for their purposes, such as being a microsphere having a diameter of 0.40 millimeters or less for use in injection equipment or in the case of wire or ribbon, having a similar diameter to permit interstitial tissue implanation through a regular 21 gauge needle or through a thin-walled 22 gauge needle.

The radioactive coat of the multilayered radioactive microsphere comprises one or more of: (1) a metal such as palladium-103, gold-198, thulium-170, or chromium-56, a mixture of metals, a mixture of compounds including radioactive metals or radionuclides, or a radionuclide bound to a metal; or (2) a dielectric radioactive element such as arsenic-73, yttrium-90, or iodine-125 or compound dielectric materials containing one non-radioactive and one radioactive component such as zirconium iodide Zr (I-125)$_4$, hafnium iodide Hf (I-125)$_4$, titanium iodide Ti(I-125)$_2$, silver iodide-125, thulium bromide-170, magnesium arsenide-73, potassium iodide-125, rubidium silver iodine-125, or copper iodide-125; or (3) any combination of radioactive dielectric compounds; or (4) two or more radioactive components, such as for example arsenic-73 and di-iodide-125, arsenic-73, selenide-75, or palladium-103 and iodide-125.

The radioactive coat may also be formed in different configurations such as by being laminated together with a nonradioactive high boiling point or hard metal by sputtering, laser ablation ion plating, ion beam sputtering, or cathodic arc deposition; (2) by being uniformly covered by a spherical diffusion barrier that may consist of a coat of single metals such as gold, tantalum, palladium, and titanium or several layers of metals or compounds such as titanium-palladium-gold, gold-titanium, titanium nitride (TiN), zirconium nitride (ZrN), titanium carbide (TiC), titanium (T) tungsten/titanium (W/T), tungsten carbide (WC) tungsten nitride (WN), tungsten/titanium nitride (WTN), hafnium nitride (HfN), Hafnium carbide (HfC), zirconium carbide (ZRC), Vanadium carbide (VC) boron carbide (BC), tungsten boride (WB) or diamond. The diffusion barrier may be covered by a uniform spherical thick (up to 0.10 millimeter) protective coat.

Either inside the radioactive layer or over the diffusion barrier inside the protective coat, there may be an inner spherical uniform special purpose coat. This special purpose coat may he used to enhance imaging of the multilayer radioactive microsphere by means of conventional radiographs or MR, CT, SPEC or PET imaging. For example, the special spherical inner coat may consist of gadolinium for magnetic resonance imaging of the multilayer radioactive microsphere.

The spherical thick outside protective coat may be composed of: (1) a resistant human tissue-compatible metal which also has low atomic weight to minimize X-ray shielding such as titanium or other corrosion-resistant metal alloy such as stainless steel; or (2) a resistant human tissue-compatible metal compound (using reactive nitrogen, oxygen, methane, or carbon monoxide gases during coating to form carbides, nitrides, or carbonitrides of transition metals or other metals) such as titanium carbide, titanium nitride, titanium carbonitride, titanium aluminum nitride, zirconium nitride and hafnium nitride; or (3) a resistant human tissue-compatible metal coating less than 0.1 millimeters thick which has a high atomic weight such as tantalum, platinum or gold or the corresponding compounds of tungsten carbide, tantalum carbide, or platinum oxide; or (4) a human tissue-incompatible metal coating which is covered by a tissue-compatible thin coating.

If a tissue-compatible outermost thin coat is included it may be sputtered diamond, tantalum, tungsten or titanium and should overlay the thick protective metal casing. In this case, the more toxic but low atomic weight metals such as beryllium, vanadium, nickel and boron nitride may be used as the thick protective casing. The thin outer coats may consist of a special-purpose coats designed to enhance physical properties of the seed such as diamond or diamond-like carbon, platinum, or tantalum. These coats individually enhance the multilayer radioactive microsphere by adding hardness, and corrosion resistance.

The outermost thin coat may also be used to produce different seed identification colors. For example, the outermost thin coat may consist of titanium nitride (TiN) to produce a golden color, titanium carbonitride (TiCN) to produce a brown color, titanium aluminum nitride (TiAlN) to produce a black color, titanium carbide (TiC) to produce a gray color, zirconium nitride (ZrN) to produce a silver-yellow color, and hafnium nitride (HfN) to produce a yellow-green color.

The central sphere or other coats may be formed of a material that is heatable by remotely radiated energy for hyperthermia and/or a material that enables force to be applied to the seed to move it around using externally radiated energy to avoid damage to tissue. For example, ferrogmagnetic materials may be used that heat by induced radio frequency energy to the Curie temperature and have a Curie temperature appropriate for hyperthermia, such as for example, 50 degrees Centigrade. Moreover, a ferromagnetic material may cause movement of the seed by externally applied magnetic fields.

In one form of therapy using the multilayer radioactive microsphere, multiple low activity multilayer radioactive microsphere's (between 30 and 300) are permanently implanted into a human tumor at approximately 1 cm (centimeter) intervals throughout the volume, thus producing continuous low-dose-rate low energy irradiation at less than 1.0 Gy/hour and preferably less than 0.20 Gy/hour and delivering minimum doses of 80 to 400 Gy to the tumor volume over the average lifetime of the multilayer radioactive microsphere.

In another form of therapy using the multilayer radioactive microsphere (MRM), several (1 to 10) high activity multilayer radioactive microsphere's are permanently implanted into a human tumor producing continuous low-dose-rate low energy irradiation at less than 1.0 Gy/hour and preferably less than 0.20 Gy/hour and delivering minimum doses of 80 to 400 Gy to the tumor volume over the average lifetime of the multilayer radioactive microsphere.

In still another form of therapy, a long term low energy radiation is applied to a tumor followed by a short term high energy radiation. In one embodiment, the low energy radiation serves as a radioactive sensitizer which blocks tumor cells in the most radioactive sensitive portions of their cell cycles and the high energy beam is applied when the tumor cells are sensitive.

In one embodiment, a low intensity radioactive seed is implanted to provide the long term low intensity radioactivity and external radiation beam is used for the high intensity. In this embodiment, the relatively low radiation dose of between 40 to 80 Gray is delivered substantially continuously at a low dose rate over a time period of 30 to 200 days and preferably approximately 30 days. Either temporary or permanent implantation of one or several seeds may be used to accomplish this purpose. This low dose-rate radiation blocks the tumor cells in their most radioactive sensitive parts of their cell cycles. These are optimally killed at the time of delivery of a conventional daily fractionated radiation given over two minutes each 24-hour period for five days a week.

To avoid leakage of radioactive material, a layer of metal that chemically reacts with the material in the radioactive layer may be sputtered or otherwise coated over the radioactive material and before the defusion layer. For example, silver may be sputtered as an even coat over radioactive iodide layers to reduce leakage. The density and uniformity of the barrier layer is maximized by coating under the lowest pressure possible and by introducing maximum energy while avoiding welding of the microspheres together.

To make multilayer coatings of a microsphere for mass-production of the multilayer radioactive microsphere, a microspherical substrate is coated with multiple uniformly-spherical coats which consist of a radioactive coat, a thick protective coat (up to 0.1 millimeter), and in some embodiments, a diffusion barrier coat, an optional special-purpose imaging-enhancement coat and an optional special purpose outer thin coat.

The microsphere is adapted to be made in a manufacturing process that eliminates the need for assembly of separate seed parts and welding of titanium tubing containing the radioactive material because the multilayer radioactive microsphere is constructed by electronic means. In the processes used: (1) one-hundred to one-thousand multilayer radioactive microsphere's can be produced in a single batch or run of the coating equipment; and (2) the design of the multilayer radioactive microsphere can be easily modified or its components or type of radionuclide easily changed by changing either the target materials, coating atmosphere or operational parameters of the coating process.

In manufacturing the coats, existing coating techniques are used. In one embodiment, one or more radioactive dielectric or metal materials are used as a target in a sputter-deposition, laser ablation, or cathodic arc plasma-deposition system to produce a stable radioactive radionuclide-metal coat upon microspherical substrates, ribbon-mircospheres, or wire substrates. Moreover, combinations of radioactive and nonradioactive materials may be used.

The deposition of the radionuclide coat or laminate of a radionuclide and high-boiling point metal must be uniform. The peak-to-valley height variation in this coating should not exceed plus or minus 400 Angstroms. It should have high quality in terms of uniformity, spherosity and not have macroparticles, holes or other defects.

Other thin layers should be uniform but are not as sensitive to the lack of uniformity. Those layers are the diffusion barrier coat and in some embodiments, imaging coats. A relatively thick protective coat such as one of 0.05 millimeters is less critical as to uniformity.

All of these substrates are applied by processes which bond so there are substantially no voids in the member. Generally, sputtering is preferred with the thicker layers utilizing higher power and larger targets and the thinner layers smaller targets and lower power so that the same apparatus may be used for the different coats and all be applied with reasonable speed in spite of the difference of thicknesses by energizing different targets at different times. Thicker coats might also be applied by cathodic arc plasma-deposition techniques although these techniques do not usually apply with the same uniformity. In a few embodiments, electrolysis is suitable although electrolysis in most applications does not provide as uniform a surface area as sputtering and in the case of microspheres, it is difficult to obtain uniformity on all sides.

Generally, fabrics, wires and ribbons may he plated while they are suspended in a vacuum but the microspheres require a levitating device such as a vibrator that bounces them so that they will he coated on all sides. The most uniform coats are applied by vacuum methods but there are other methods which can create the uniformity and intimate contact of the coats desired in these products. Because some of the radionuclide coats are soft, low boiling point metals, special precautions can be taken to prevent the microspheres from being welded together. One such precaution is to combine the low boiling point radionuclide with a higher boiling point metal in interleaved areas or concomitantly. Injection of 1% to 5% of an electronegative gas such as oxygen gas will present microsphere vacuum welding. Tn another embodiment, gaseous radionuclides are bound by combining them with a metal during the coating process such as by sputtering the radioactive nuclide gas together with a metal in an argon atmosphere to form a coat of a compound combining the radionuclide and the metal.

The multilayer radioactive microsphere radioactive microspherical substrate coat may be produced by one of several processes, such as: (1) from a radioactive metal target by dc sputtering; or (2) by radio frequency or mag- netron sputtering using a radioactive dielectric target; or (3) by reactive sputter-deposition in an excited radioactive gas producing a coat which is a radioactive compound of the radioactive gas and the sputtered target material; or (4) by reactive cathodic arc plasma deposition in an excited radioactive gas producing a coat which is a radioactive compound of the radioactive gas and the sputtered target material; or (5) by reactive ion beam sputtering using a cathodic arc ion source in an excited radioactive gas producing a coat which is a radioactive compound of the radioactive gas and the sputtered target material; or (6) by reactive ion-plating using an electron-beam source in an excited radioactive gas producing a coat which is a radioactive compound of the radioactive gas and the sputtered target material; or (7) by cathodic arc plasma deposition using a radioactive dielectric target; or by (8) laser ablation of the target metal in the presence of a radioactive gas forming a radioactive metal compound on the substrate.

A radioactive dielectric coated planar metal target for use in cathodic arc plasma deposition or for use in rf or magnetron sputtering may be made by coating a metal planar substrate with a radio-active dielectric compound using reactive dc, rf, or magnetron sputtering, reactive cathodic arc plasma deposition, reactive ion-beam sputtering, or reactive ion plating wherein the radioactive compound coat is produced from an excited radionuclide gas and a non-radioactive metal target.

To optimize mass-production manufacture of the multilayer radioactive microsphere a two step process is used employing sputter deposition with a radioactive dielectric or metal target, or reactive sputter deposition in a radionuclide gas to produce a uniform radioactive coat over a microspherical substrate followed by ion-plating, or ion-beam self-sputtering using a cathodic arc ion source, or cathodic arc plasma deposition or high-energy high deposition rate sputtering using a large sputter gun, to produce the remaining coatings and spherical thick protective metal coatings over the radioactive microspheres.

In another method for mass-production manufacture of the multilayer radioactive microsphere consisting of a one-step process employing reactive cathodic arc plasma deposition, reactive laser ablation deposition, or reactive ion beam sputtering using a cathodic arc ion source, or reactive ion plating all carried out in an excited radionuclide reactive gas/inert gas mixture to form a smooth spherical stable compound radioactive coating over a microspherical substrate, followed by use of either ion plating, ion beam sputtering, cathodic arc deposition or laser ablation to produce the remaining coatings and spherical thick protective metal coatings over the radioactive microspheres.

In still another optimized method for mass-production manufacture of the multilayer radioactive microsphere consisting of a one-step process employing cathodic arc plasma deposition using a radioactive dielectric or metal target to produce a radioactive coat over a microspherical substrate, followed by use of cathodic arc plasma deposition to produce the remaining coats and spherical thick protective metal coats over the radioactive microspheres.

To eliminate vacuum welding between levitated microspheres, soft low boiling point elements (that are likely to vacuum weld) are laminated with hard, high boiling point elements (that are unlikely to vacuum weld). The microspherical substrates may be biased to improve reactive deposition efficiency using a reactive gas in a sputtering, ion plating, ion beam sputtering, or cathodic arc deposition. Moveover, levitation is improved to further reduce welding by creating a capacitive bias effect with the bouncing pan being electrically isolated from the rest of the sputtering apparatus. To create the capacitive bias effect, the bouncing pan may be an insulating ceramic with a conductive liner or may be a conductor coated with an insulating material. The material is connected by a conductor to a source of potential to create the bias. The bouncing pan is driven at high power by an ultrasonic transducer that is tuned to a frequency slightly different than the resonant frequency of the system.

Several embodiments of therapeutic devices can be formed. In one embodiment a ribbon-multilayer radioactive microsphere substrate has microspheres attached to the ribbon prior to coating. Coats are then applied to form a ribbon surface for rapid implanting of seeds. The coats may vary at different locations to enable in some embodiments, a contoured radiation pattern. In another embodiment, a multilayered radioactive wire design has a coat applied to a wire substrate by means of sputtering, laser ablation ion plating, ion beam sputtering, or cathodic arc deposition. The radioactive material is differentially deposited onto a substrate wire in such a manner that variable activities are deposited per unit length in a controlled fashion to match a computerized treatment plan.

In other embodiments, absorbable or non-absorbable surgical fabrics containing multiple multilayer radioactive microspheres spaced apart on the fabric or miniturized intracavitary sources of radioactivity composed of multiple multilayer radioactive microsphere's are fabricated. Coats are applied in successive layers on the fabric and microsphere substrate or only on the microsphere substrate using masking in forming a fabric. Also, finished microspheres can be embedded during manufacture of a cellulose fabric. To form small intracavity sources, microspheres are first formed by sputtering or other such manufacturing technique and then afterloaded into containers that are welded shut. In still another embodiment, an ocular applicator is constructed in which radioactive multilayers are deposited on the active surface by means of sputtering, ion plating, ion beam sputtering, cathodic arc deposition, or laser ablation.

Some of the embodiments that are fabricated enable improvement in other known techniques. For example, a modified multilayer radioactive microsphere that contains a ferromagnetic alloy that may be inductively heated in situ by applied radio frequency radiation may be formed. The coat passes through a Curie transition at temperatures useful for clinical hyperthermia and stops receiving inductive heating, thus maintiaining the proper temperature. Also, a solid multilayered radioactive needle for temporary removable implants incorporates a wide variety of radionuclides and is thinner than a conventional radium-containing needle, thus enabling its use without major tissue trauma and improving the implant geometry.

The radioactive single seed design of this invention has several advantages such as: (1) it is smaller than prior art radioactive seeds and is spherical thus permitting a wider range of uses and easier use with less traumatic insertion into human tissues; (2) it is stronger and has high structural integrity and is thus safer; (3) it is symmetrical and uniform and thus produces a symmetrical radiation field as shown by symmetrical dosimetry; (4) it may be constructed using a wide variety of isotopes of differing energies and half-lives selected for specific applications, thus permitting optimization of the radiobiology of the type of cancer being treated; (5) it is inexpensive; and (6) in clinical practice, it permits safe delivery of radiation tumor doses that are two to five times higher than that achieved with external beam irradiation; and (7) the different multilayered. radioactive microspheres can be identified by their different imaging contrast agent coats or center substrate.

In use, the microspheres have several advantages such as: (1) an effective modality for treatment is provided by combining a relatively low continuous dose of radiation by multilayer radioactive microspheres implanted in a tumor at any anatomic location and which serve as radiosensitizers so that a short conventional course of external-beam radiation therapy is much more effective; (2) radiation dose localization is improved beyond that achievable with the low energy permanent gamma-ray seeds by use of an electron-producing seed because electron dosimetry is more localized than X-ray dosimetry; (3) different types of multilayered radioactive microspheres with different half-lives and photon or electron energies can be implanted into a tumor in the same operation to optimize tumor therapy; and (4) the use of permanent implantation of short-lived seeds rather than temporary-removable implants eliminate exposed tubes which penetrate the skin surface and serve as a route for infection over many days.

There are also advantages from the composite designs that can be produced using the spheres, such as for example: (1) ribbons and a tissue-compatible fabric containing seeds useful for rapid surgical implantation may be produced; (2) the thin ribbon design containing multiple seeds allows rapid implantation of multiple seeds using a hollow interstitial needle; (3) a tissue-compatible surgical fabric containing multiple radioactive seeds allows rapid intraoperative implantation of a sheet of evently spaced radioactive seeds; and (4) the various surgical procedures and devices used for implantation of radioactive seeds provide better adaptability to a patient's needs.

There are also advantages from a wire multilayered radioactive design such as: (1) it may be cut up into pieces and placed into afterloading catheters or into nylon or polyethylene ribbons for temporary removable implants or placed inside appropriate containers to construct various intracavitary sources; (2) it has the advantages of being flexible or remain as a long needle, with or without an added sleeve for temporary implanting.

When encapsulated: (1) the multilayered radioactive microspheres simplify intracavitary therapy because smaller intracavitary capsules can be construed using multiple small-diameter seeds of the present invention; (2) a wide variety of radionuclides with energies varying from very low to very high can be incorporated into composite intracivitary sources by sealing multiple multilayered radioactive microspheres of one or several types into an appropriate container; (3) use of low energy intracavitary sources composed of low energy multilayered radioactive microspheres allow selective shielding of adjacent vital structures such as rectum and bladder using relatively thin high atomic weight foils placed over the intracavitary sources or source holders.

There are also several advantages related to manufacturing the radioactive implants such as: (1) it permits mass production of a variety of designs without need of assembly of separate (radioactive) parts; (2) changes in seed composition may be made easily; (3) it permits customized manufacture of multilayered radioactive microspheres, multilayered radioactive wires, ribbon-multilayered radioactive microspheres or optical plaques optimized for individual tumor types; (4) manufacture of new models of multilayered radioactive microspheres, multilayered radioactive wires and ribbon-multilayered radioactive microspheres can be accomplished as needed by simply changing deposition parameters, or by changing the type, thickness, and layering of deposited elements using the same deposition equipment; (5) it permits construction of seeds containing many optional different types of laminated materials such as imaging contrast agents, colored seed identification markers, or supplemental protective outer layers; (6) use of the high energy processes of sputtering, laser ablation ion-beam sputtering, cathodic arc or curvilinear cathodic arc plasma deposition, reactive deposition, and ion plating increase the hardness of metals coated in this manner compared to the bulk materials; and (7) the controlled variable deposition of radioactive material per unit length or per unit surface area permits customized manufacture of brachytherapy sources to exactly match the requirements of 3-dimensional computerized brachytherapy treatment plan.

The ability to provide a variety of half-lives and intensities of implants has several advantages, such as for example: (1) the smaller permanent seeds permit implantation of a greater number of seeds in more body sites using thinner needles with less risk of complication; (2) a combination of short-acting high-energy and long-acting low energy seeds can be implanted in the same procedure; (3) under some circumstances repeated implantation of seeds with short half-lives may be used instead of repeated temporary removable implant procedures thus reducing the risk of infection associated with temporary removable implants; (4) high energy short-lived seeds provide results equivalent to a temporary removable implant, but they may be applied to sites not accessible to temporary removable implantation; (5) short-lived seeds may be implanted as a "tumor-boost", replacing and improving upon a "tumor-boost" delivered by means of external-beam radiation therapy; (6) with a wide variety of seeds available, many cancers can be more effectivley managed by brachytherapy alone; (7) a wide variety of radionuclides with energies varying from very low to very high can be incorporated into composite intracavitary sources by sealing multiple multilayered radioactive microspheres of one or several types into an appropriate container; (8) use of low energy intracavitary sources composed of low energy multilayered radioactive microspheres allow selective shielding of adjacent vital structures such as rectum and bladder using relatively thin high atomic weight foils placed over the intracavitary sources or source holders.

The ribbons, wire, plaques and fabric of this invention have the advantages of: (1) multiple multilayered radioactive microspheres provided on a single ribbon allow multiple multilayered radioactive microspheres to be implanted at once by a thin gauge hollow needle by pushing the multilayer radioactive microsphere ribbon out of the tissue-embedded needle with a stylet while withdrawing the needle; (2) the ribbon-multilayered radioactive microspheres of the present invention may be implanted by a very thin 21 or 22-gauge needle; (3) the fabric of this invention self-adheres to the tissues over which it is placed and may he either tissue-absorbable or non-tissue absorbable; (4) the use of a fabric containing multiple multilayered radioactive microspheres allows rapid surgical implantation of multiple seeds without need of interstitial needles or a seed gun; and (5) very thin plaques such as optical plaques can be contoured have the appropriate strength and appropriate intensity for effective treatment.

SUMMARY OF THE DRAWINGS

The above noted and other features of the invention will be better understood from the following detailed description when considered with reference to the accompanying drawings in which:

FIG. 8 is a sectional elevational view of a ribbon-like embodiment;

FIG. 9 is a top sectional view of the embodiment of FIG. 8;

FIG. 10 is a plan view of an optical plaque in accordance with an embodiment of the invention;

FIG. 11 is a sectional view of the embodiment of FIG. 10 taken through lines 11—11;

FIG. 12 is a plan view of another embodiment of optical plaque in accordance with the invention;

FIG. 13 is a plan view of still another embodiment of optical plaque;

Figure 19:
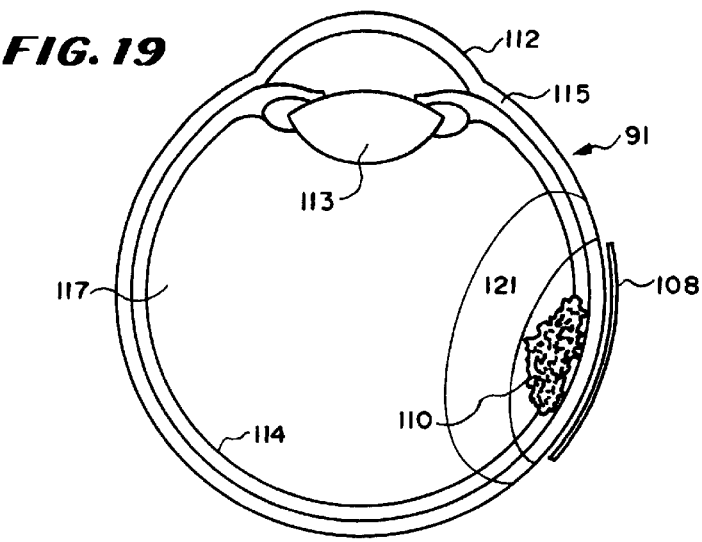
Figure 18:
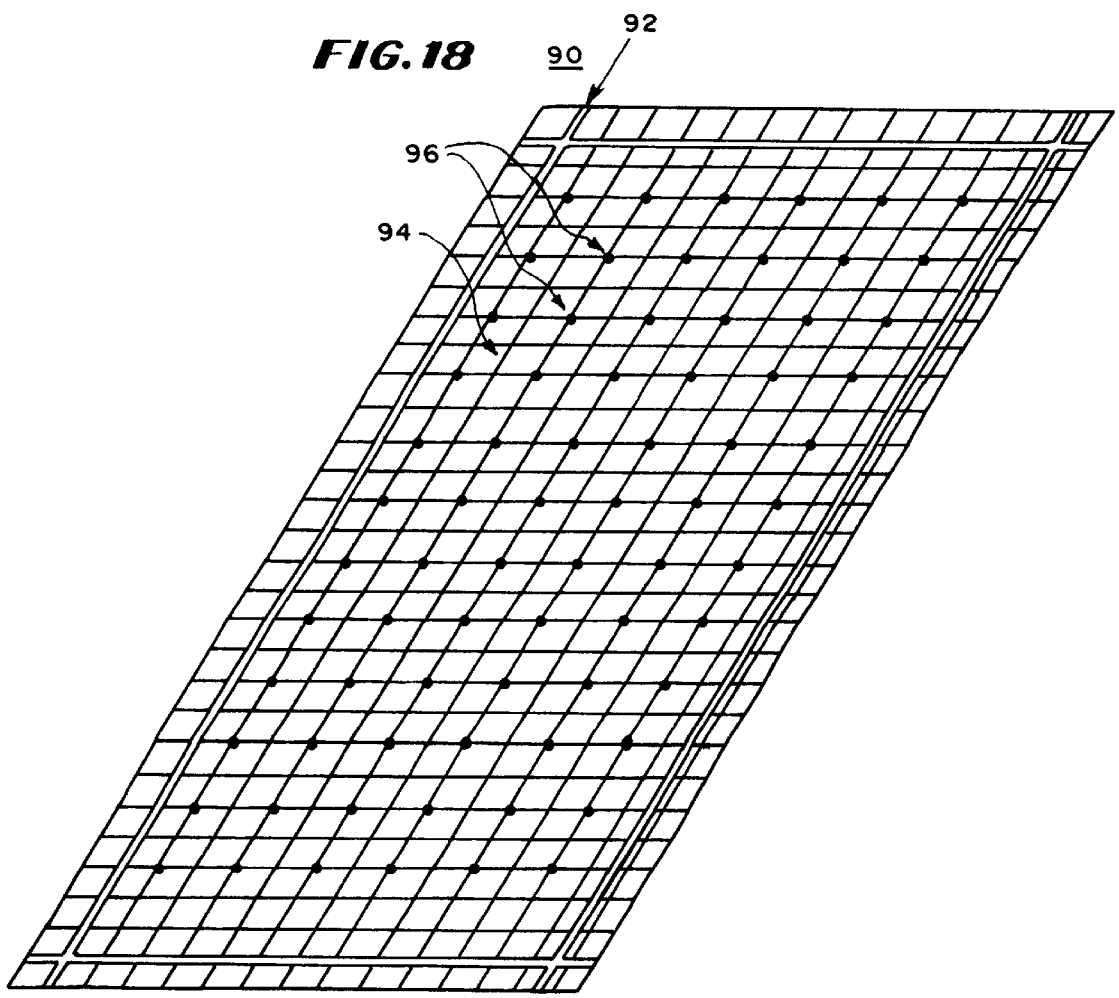
Figure 20:
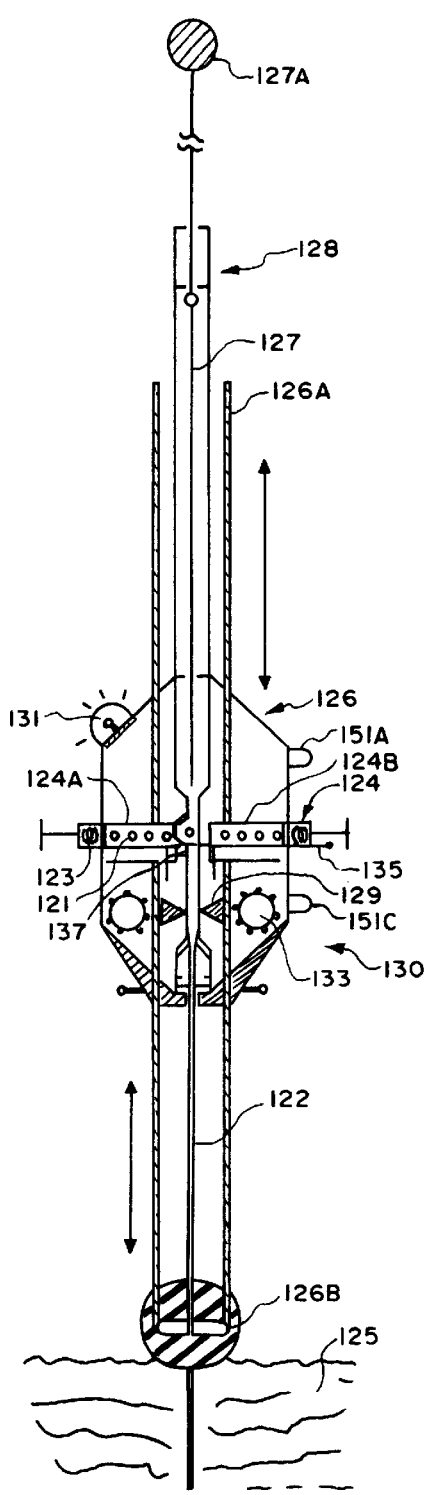
Figure 21:
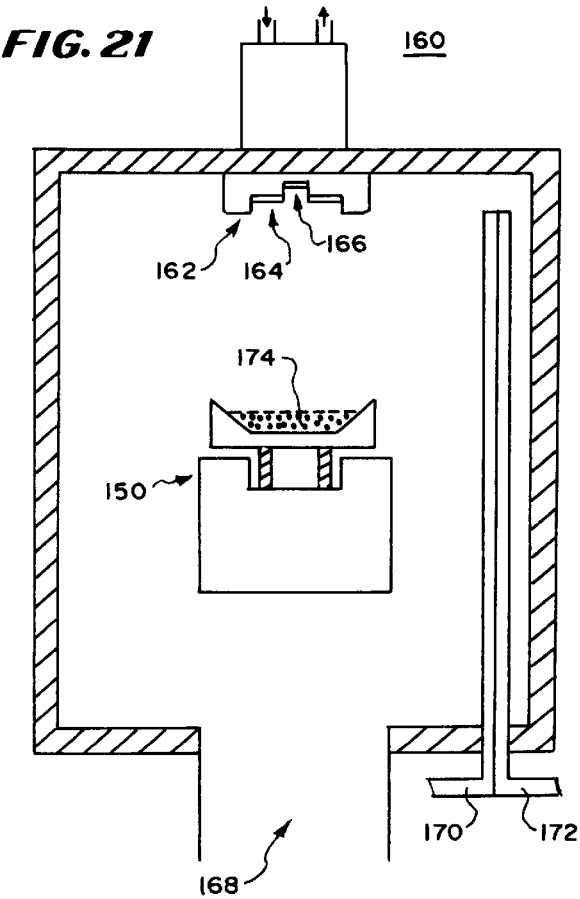
Figure 22:
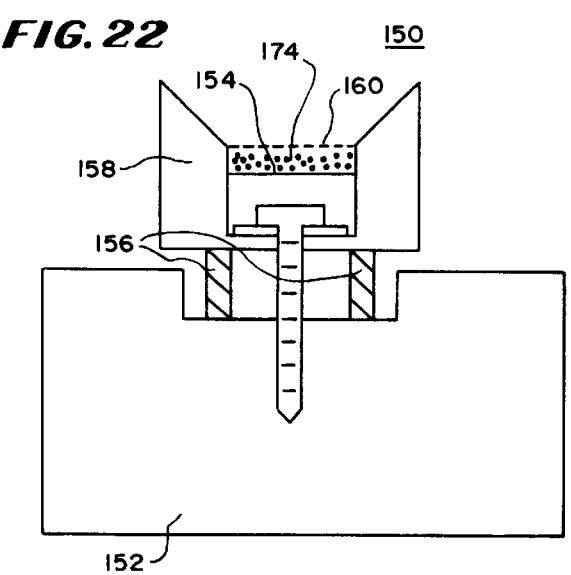
Figure 26:
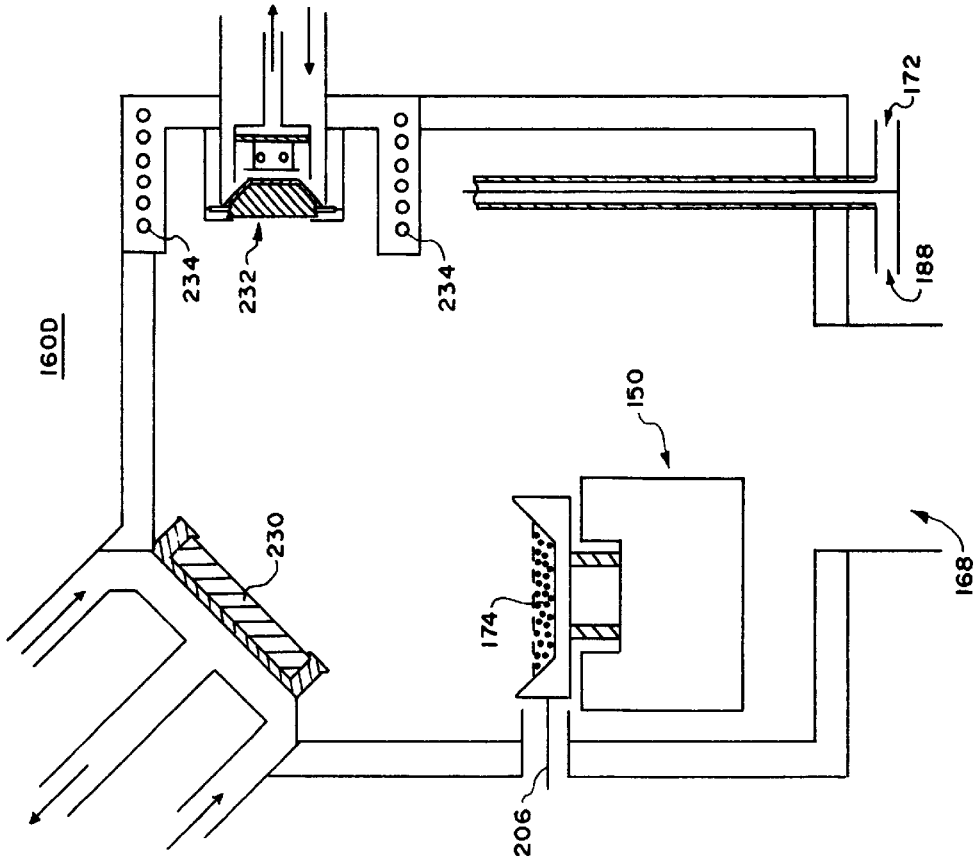
Figure 25:
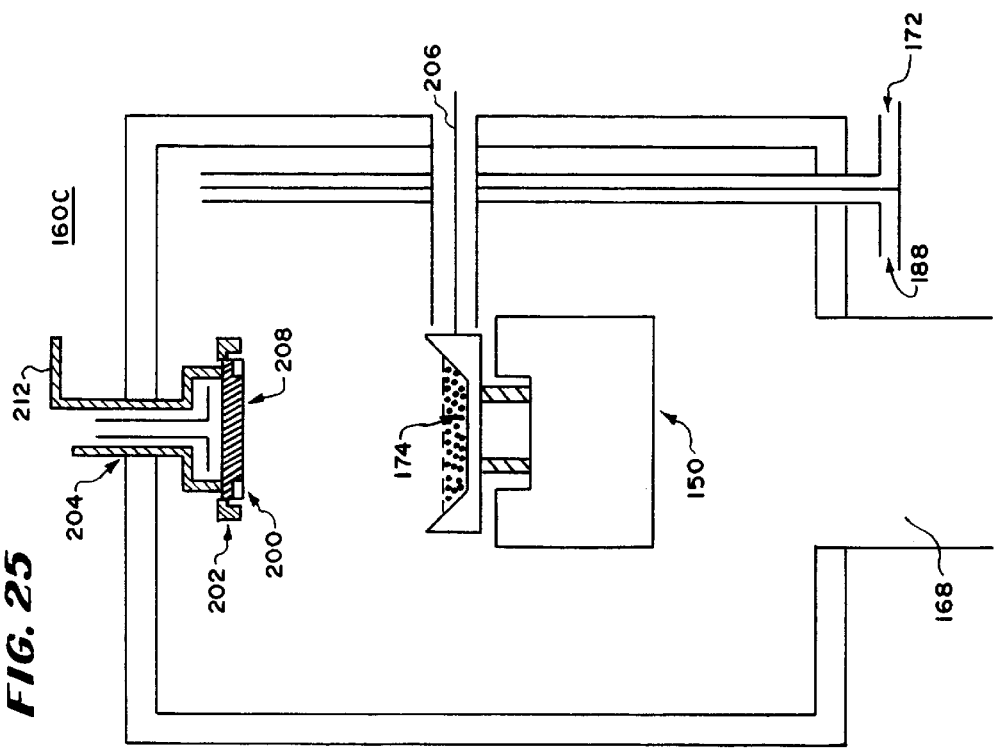
Figure 29:
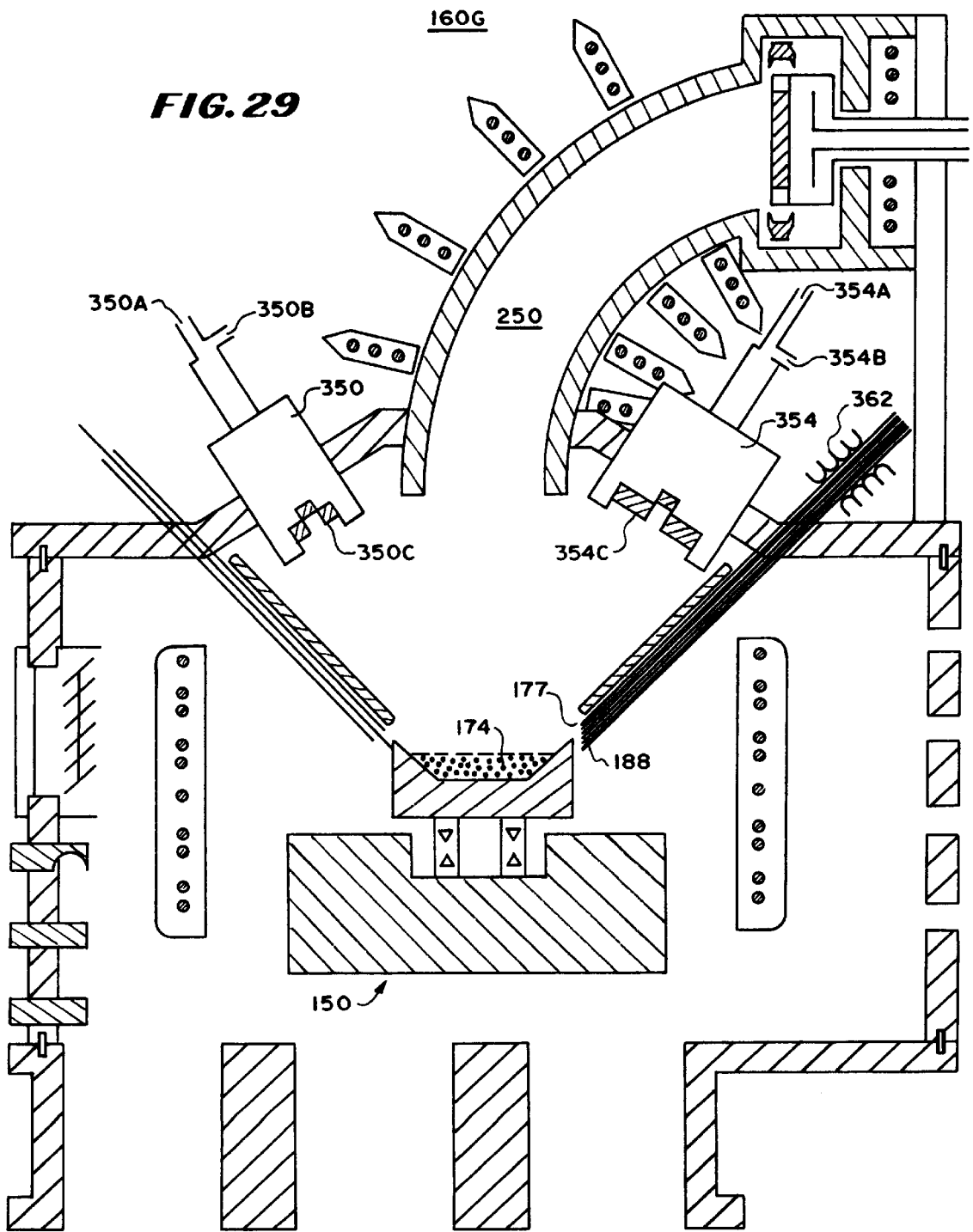
Figure 30:
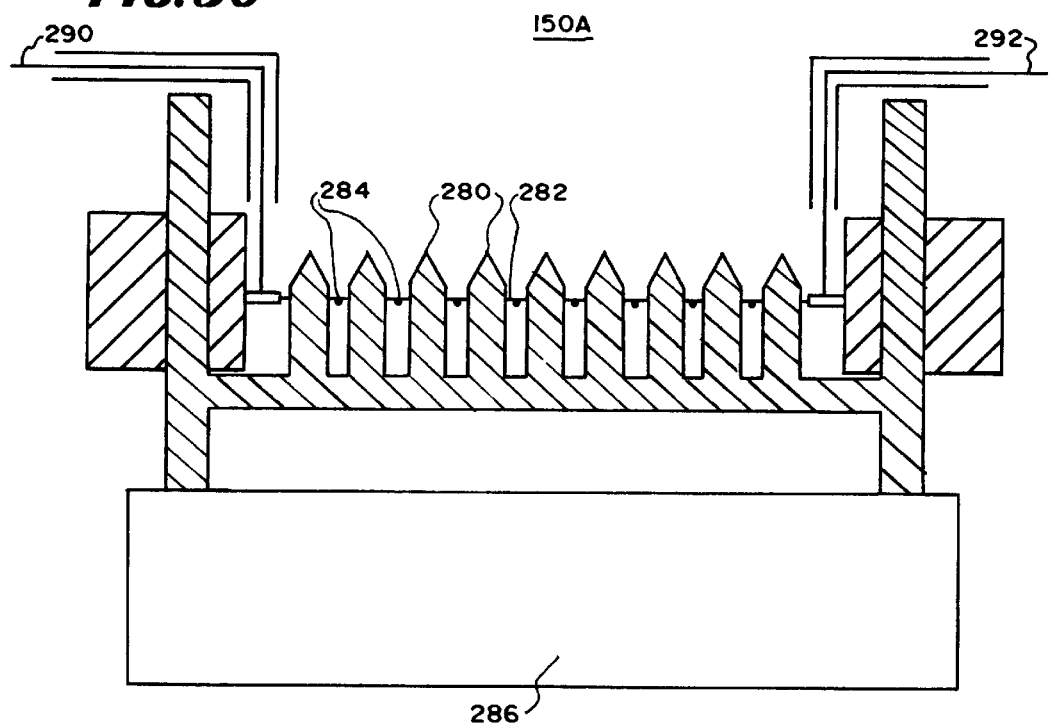
Figure 31:
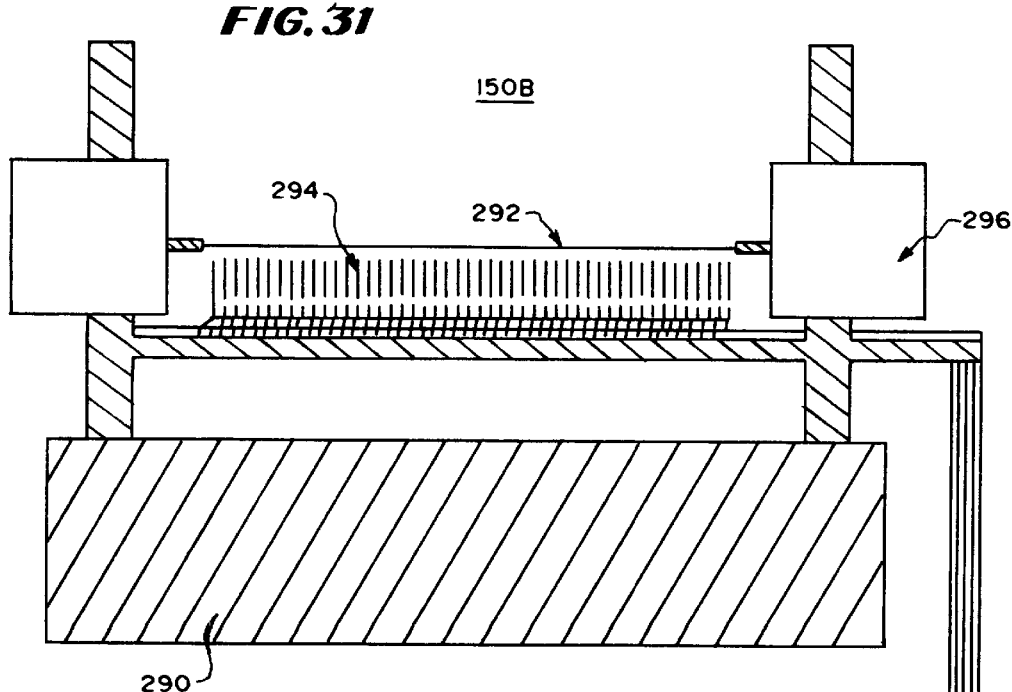
Figure 32:
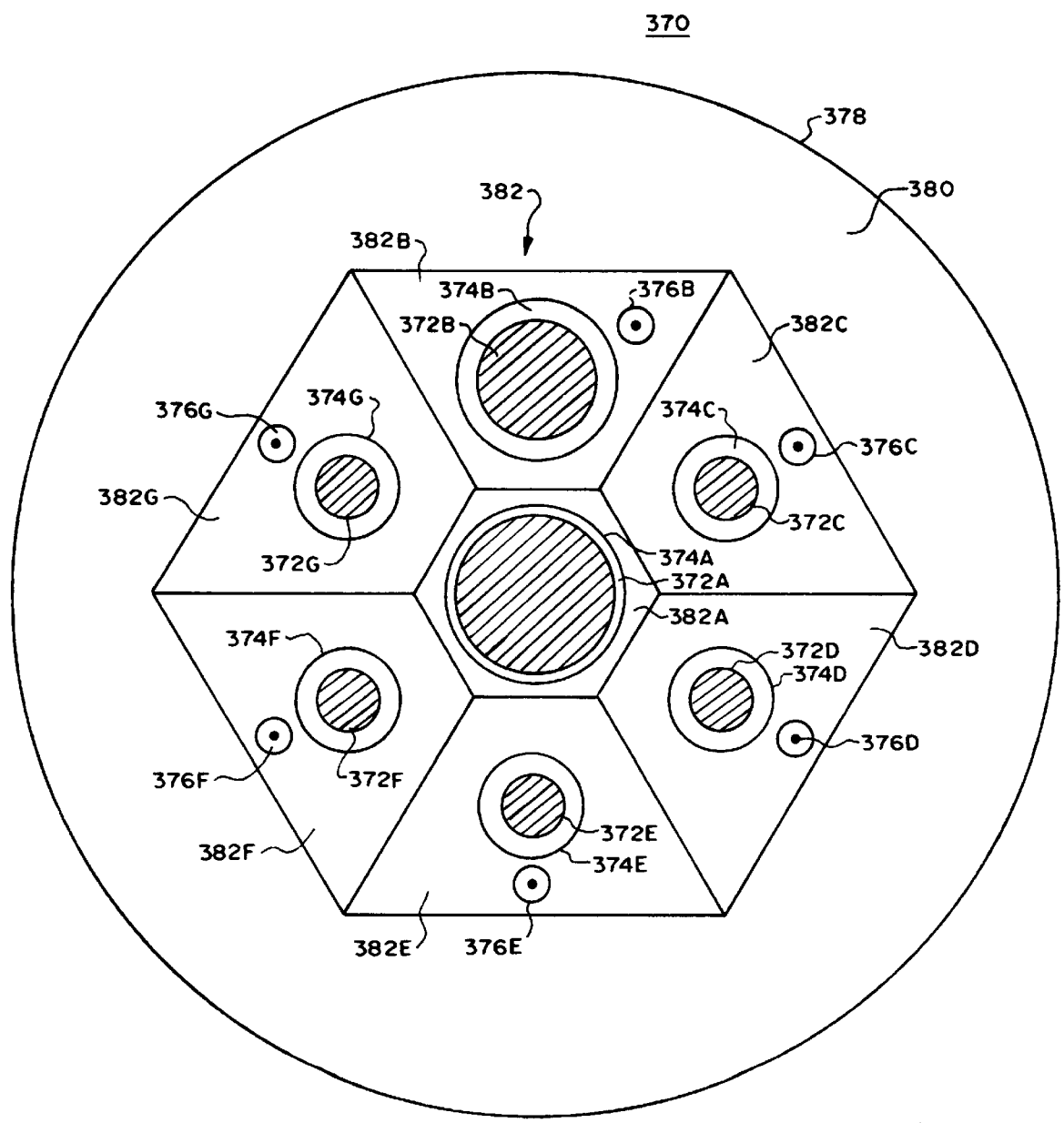
Figure 33:
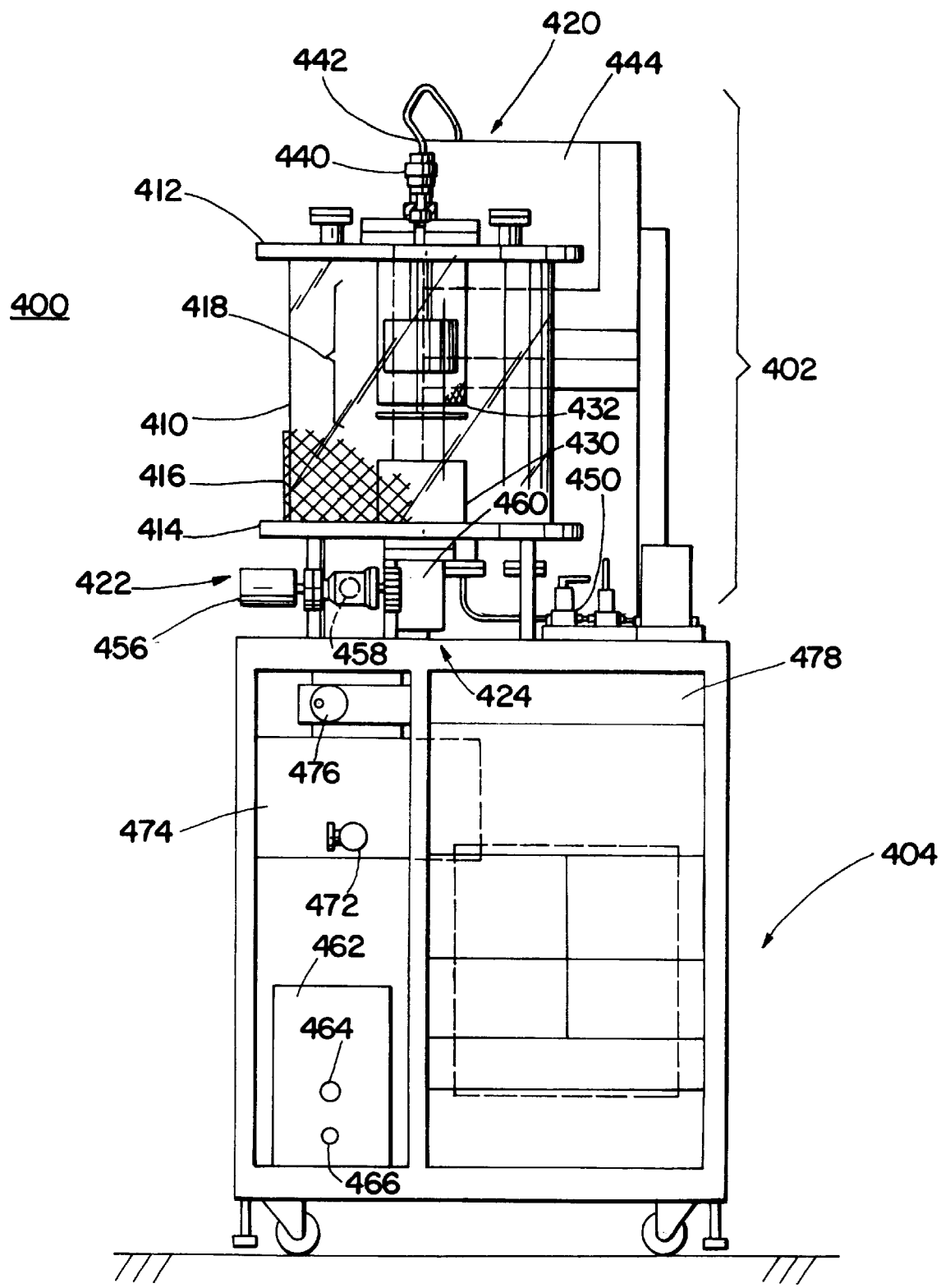
Figure 34:
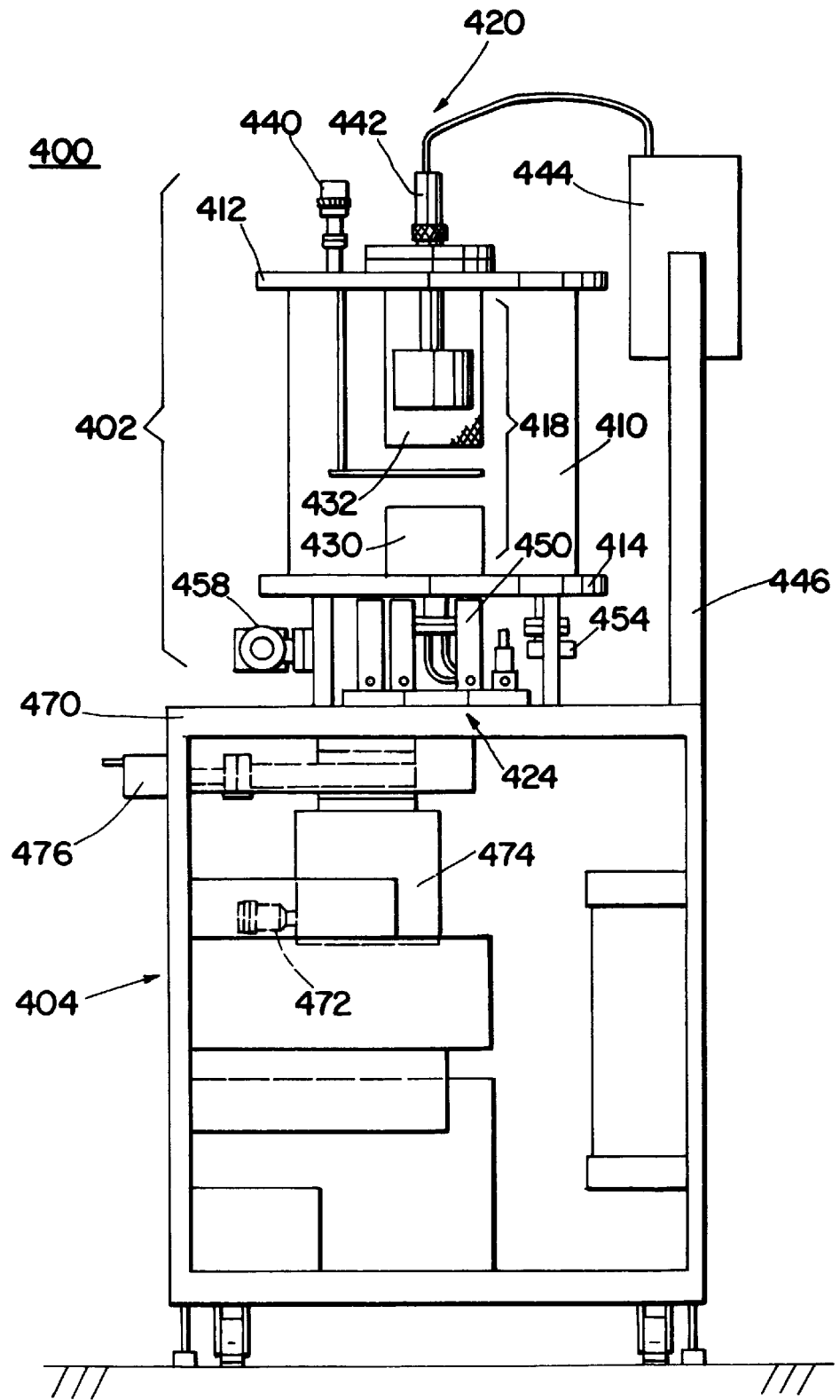
Figure 35:
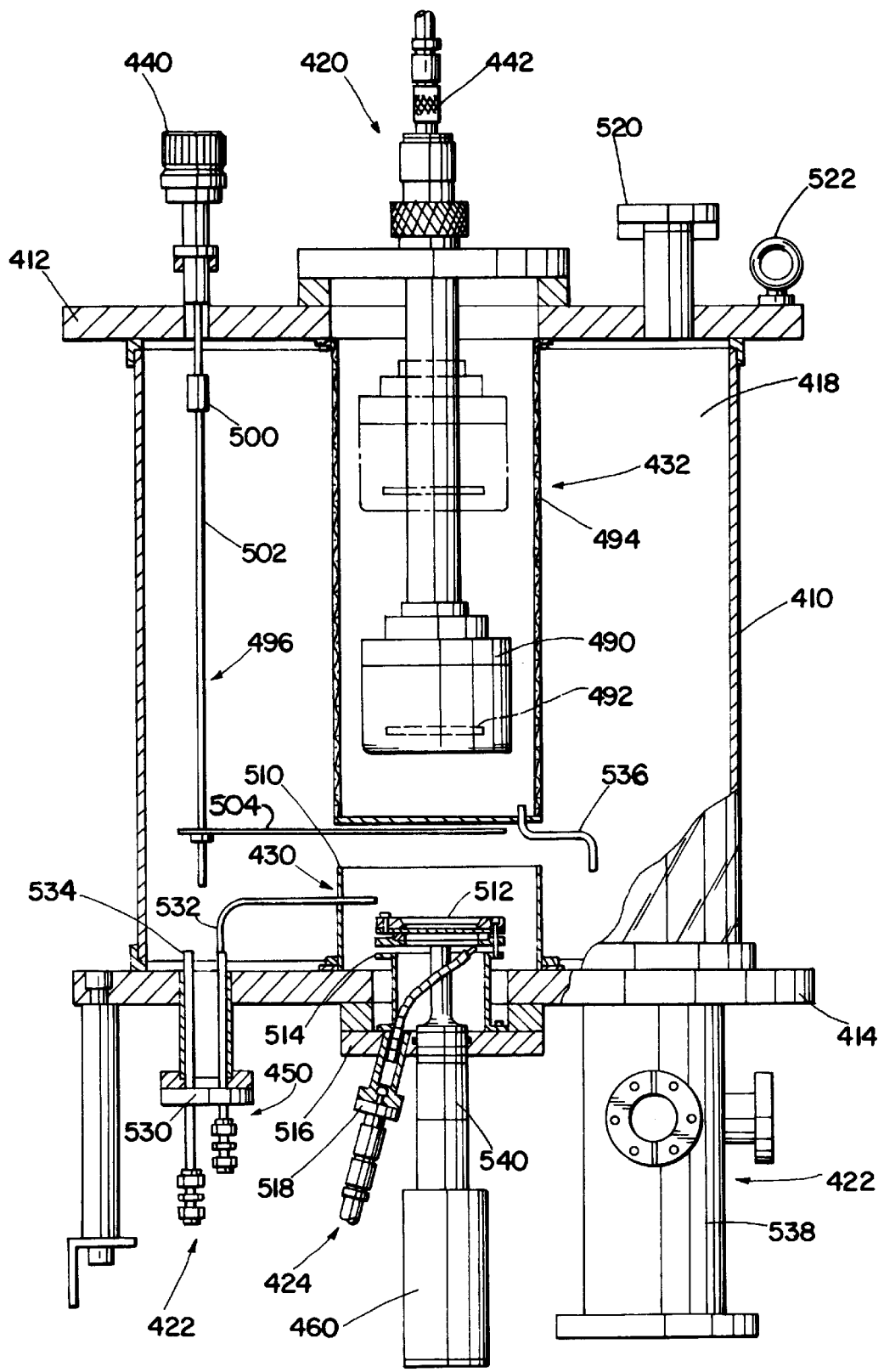

FIC. 14 is a plan view of still another embodiment of optical plaque;

FIG. 15 is a plan view of still another embodiment of optical plaque;

FIG. 16 is a plan view of still another embodiment of optical plaque;

FIG. 17 is a plan view of still another embodiment of optical plaque;

FIG. 18 is a plan view of a fabric-type embodiment of the invention;

FIG. 19 is a diagrammatic view of an eye showing a manner in which an embodiment of the invention is applied;

FIG. 20 is a diagrammatic view of an implant gun;

FIG. 21 is a schematic diagram of one embodiment of equipment for making microspheres;

FIG. 22 is a schematic diagram of another embodiment of apparatus for making microspheres;

FIG. 23 is a schematic diagram of still another embodiment of apparatus for making microspheres;

FIG. 24 is a schematic diagram of still another embodiment for making microspheres;

FIG. 25 is still another embodiment of apparatus for making microspheres;

FIG. 26 is still another embodiment of apparatus for making microspheres;

FIG. 27 is still another embodiment of apparatus for making microspheres;

FIG. 28 is still another embodiment of apparatus for making microspheres;

FIG. 29 is still another embodiment of apparatus for making microspheres;

FIG. 30 is a schematic diagram of an apparatus for preparing radiation-emitting ribbon;

FIG. 31 is a schematic diagram of another embodiment for producing variable deposition of radionuclide per unit length along elongated radiation-emitting members;

FIG. 32 is a schematic diagram of an embodiment of target assembly for use in an apparatus for making microspheres;

FIG. 33 is a front elevational view of a preferred embodiment for deposition of coats on microspheres;

FIG. 34 is a fragmentary side elevational view of the embodiment of FIG. 33;

FIG. 35 is a simplified enlarged elevational view of a chamber portion of the apparatus of FIG.

Figure 36:
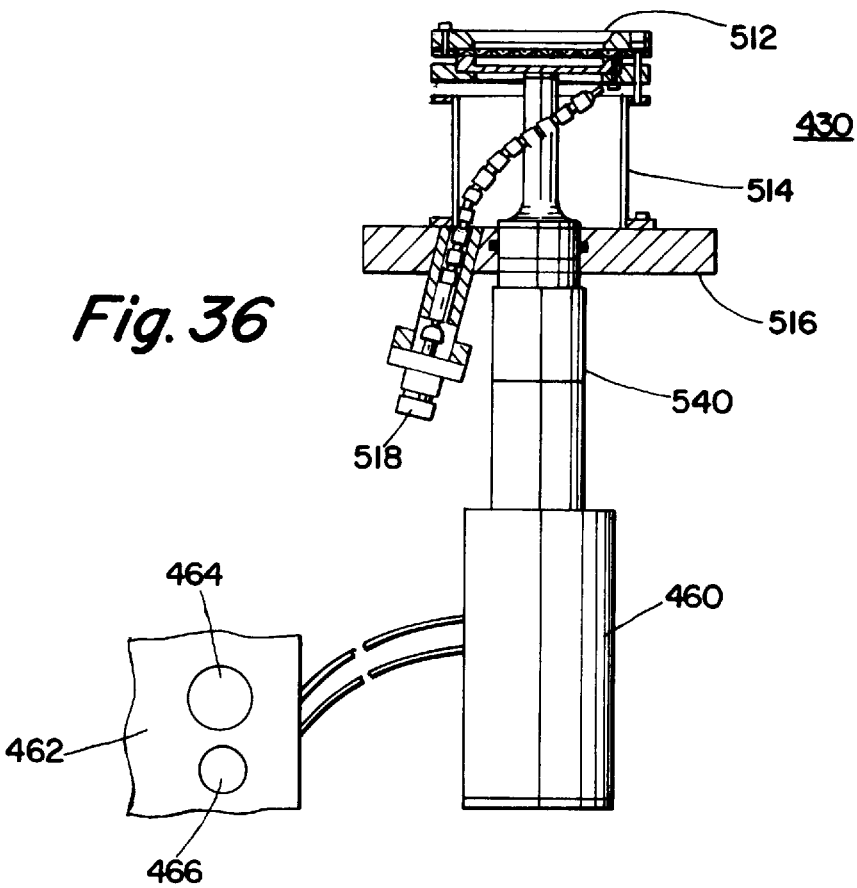
Figure 37:
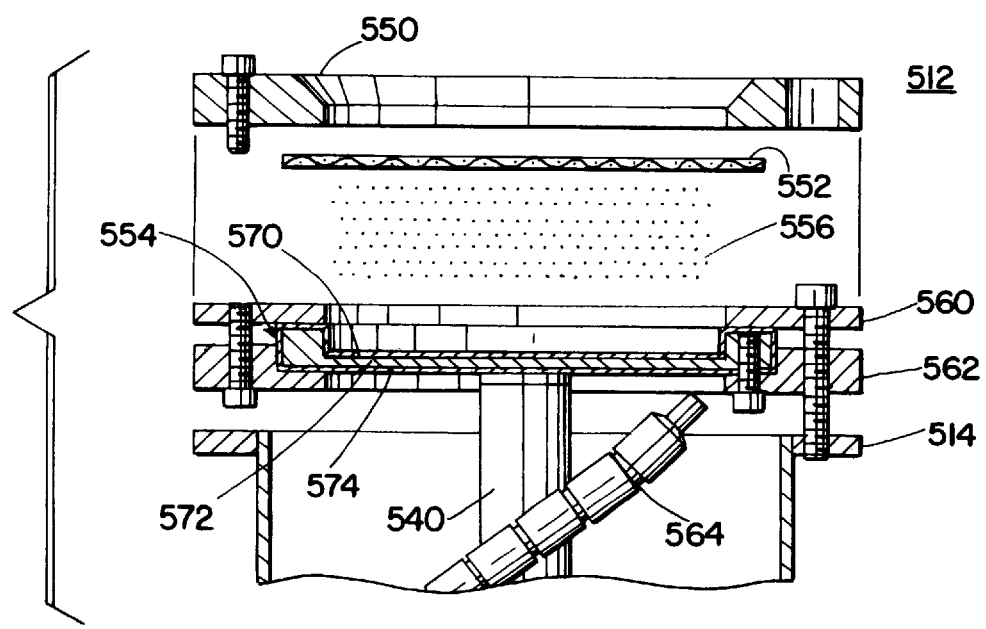

FIG. 36 is a partly schematic, partly sectioned, fragmentary elevational view of a bouncing pan and driver therefor used in the embodiments of FIGS. 33–35; and FIG. 37 is an exploded, partly sectioned, fragmentary elevational view of a bouncing pan structure used in the embodiments of FIGS. 33–36.

DETAILED DESCRIPTION

Figure 1:
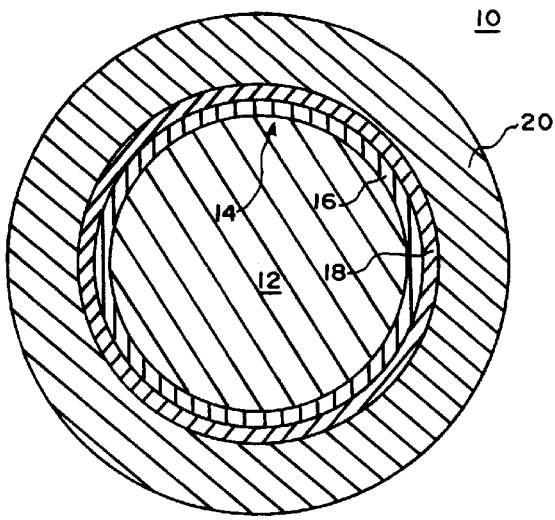
FIG. 1 is a hemispherical sectional view of a multilayer radioactive microsphere in accordance with an embodiment of the invention.
Figure 2:
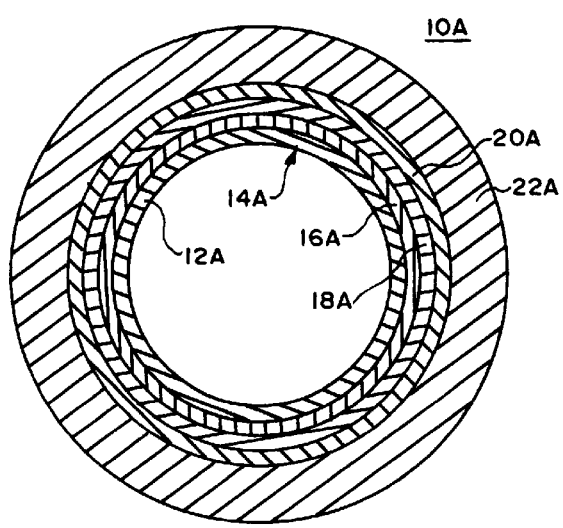
FIG. 2 is a sectional view of another embodiment of a multilayer radioactive microsphere.
Figure 3:
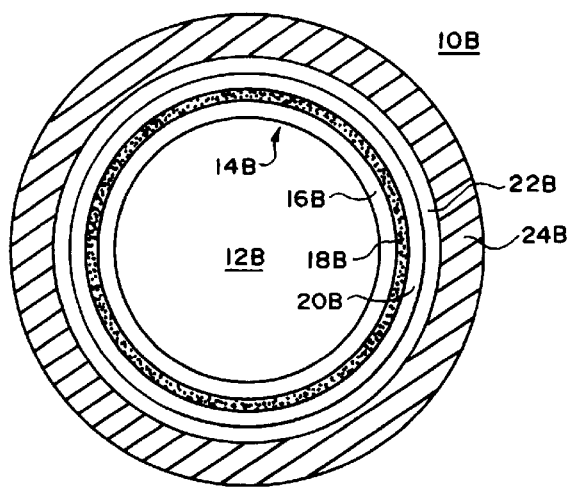
FIG. 3 is a sectional view of still another embodiment of multilayer radioactive microsphere.

In FIG. 1, there is shown a sectional view of a radiation-emitting or radioactive microsphere 10 having a central sphere 12, and a layered section 14, with no space or voids between layers or between the central sphere 12 and the layered section 14 and no end-welds. It has an outside diameter less than 1 millimeter and provides a therapeutic amount of radiation selected in accordance with the desired treatment.

The central section is a microsphere and is normally solid but may be hollow. In the preferred embodiment, the material of which the central section is made is selected to serve as a substrate for other usefull coats applied over it, and under some circumstances, to serve other functions such as to identify or locate the implant. For this latter purpose, it may be selected to be opaque to radiation such as X-rays or easily detectable by other devices. If the central section 12 is itself the source of the therapeutic radiation, there may be a reduced number of layers in the layered section 14.

The center section or core 12 is less than 1 millimeter in diameter and in the preferred embodiment is generally 0.2 millimeters. However its size may be varied to accommodate different coating processes or to distinguish one radiation-emitting sphere from another by sensing the center section or the like. In the preferred embodiment the material is selected for its function.

This substrate center or core 12 may be made of a high atomic number metal or alloy such as iridium, platinum, gold, tantalum, tungsten or lead. Additionally, any lower atomic weight metal or alloy which is satisfactorily visualized on radiographs may be used including molybdenum, indium, lithium, silver, copper, and steel. Platinum, tantalum, gold, and silver are the preferred X-ray marker multilayer radiation-emitting microsphere core substrate materials in the present invention because of their high visibility on conventional radiographs.

In another seed design disclosed wherein only magnetic resonance imaging of the seed is clinically desirable and X-ray imaging is not necessary, the seed core 12 is composed of a non-metal such as carbon or diamond and an outer seed coat producing a magnetic resonance imaging signal (gadolinium) described below produces the seed image.

A multilayer radiation-emitting microsphere without a ferromagnetic core is essentially non-magnetic. This absence of ferromagnetic metal is advantageous for clinical situations where the implanted seed is implanted in close proximity to critical structures, such as near arterio-venous malformations in the brain. Here a strong magnetic field produced by magnetic resonance imaging equipment may exert enough force to dislodge or move a ferromagnetic metal-containing seed. A magnetically dislodged seed in the brain could cause immediate neurologic damage, stroke, or death of the patient. It could also be lost into the cerebrospinal fluid.

In the embodiment 10 of radiation-emitting microsphere of FIG. 1, the layered section 14 includes three layers 16, 18, and 20, in the order named, from the center section 12 outwardly. Each layer is concentric and they are selected in accordance with any of several therapeutic techniques. Other embodiments to be described hereinafter have still further coats and some embodiments may require primer coats to improve the ability to apply the layers to the central section or to each other or may require careful selection of techniques such as using mixtures of the material of the two coats at the interface between them.

Preferred primer metals include titanium, aluminum, tin, tantalum, vanadium, titanium nitride, titanium iodide, titanium oxide, titanium carbide, or metal alloys such as stainless steels or nickel alloys. If the coated material of one coat or the central section does not have good surface compatability with any primer metal, then a graded interface can be created composed of the materials of both coats or the central microsphere and its first coat as described below for a central substrate and a first coat that is a radioactive material.

The layer 16 may be an evenly distributed, highly-controlled, uniform, smooth, thin (less than 0.01 mm to 0.045 mm) spherical radiation-emitting coat that is produced by any method that results in a layer in intimate contact without void spaces. The material of the coat 16 may be any radiation-emitting material including: (1) a radionuclide with a weighted average gamma energy of less than 100 KeV, and with a half-life of less than 130 days for low energy permanent interstitial implantation; or (2) a radionuclide with a weighted average gamma energy greater than or equal to 100 KeV and with a half-life of less than 15 to 20 days for high-energy permanent interstitial implantation; or (3) a radionuclide that has a weighted average gamma energy greater than or equal to 100 KeV, with a half-life of greater than 15 to 20 days or an average energy less than 100 KeV and a half-life of greater than 130 days for temporary removable interstitial implantation; or (4) a radionuclide that emits a high energy electron particle without significant high-energy gamma-ray component for permanent or temporary removable interstitial implantation. It may be one metal, a mixture of metals, a dielectric compound, a mixture of dielectric compounds, a radionuclide that is normally a gas but is bound to a metal or other material in the radiation-emitting layer 16 or a plurality of layers of materials.

To provide the desired characteristics, the material of the layer 16 may be a metal selected from the group comprising palladium-103, gold-198, thulium-170, or chromium-56 or a combination of these or a dielectric radiation-emitting element such as arsenic-73, yttrium-90, or iodine-125 or a combination of these or a compound dielectric material containing one non-radiation-emitting and one radiation-emitting component with the radiation-emitting component such as zirconium iodide Zr(I-125)4, hafnium iodide Hf(I-125)$_4$ titanium iodide Ti(I-125)$_2$, silver $^{125}$iodide, thulium bromide-170, magnesium $^{73}$arsenide, potassium $^{125}$iodide, rubidium silver 125iodine, or copper $^{125}$iodide. It may include a radiation-emitting dielectric compound coat having two or more radiation-emitting components including any of arsenic-73 and di-iodide-125, arsenic-73, selenide-75, and palladium-103 iodide-125 or it may be laminated with a non-radiation-emitting and radiation-emitting materials. A list of such materials is provided in tables 1–19 of appropriate target materials and gases is provided in tables 20–58.

Moreover, instead of being a radiation-emitting microsphere from the start, the layer 16 may be formed of a material not in final form and altered by imparting radiation such as by nuclear or neutron bombardment or by combination with other layers of material under energy sources such as heat. For example, the microsphere in one stage of development may include a coat that is a non-radiation-emitting isotope precursor of the desired radiation-emitting isotope (such as those elements labelled with a * in tables 1–15). One such multilayer radiation-emitting microsphere may first contain a primary coat of non-radiation-emitting palladium-102 or samarium-144 but may be later irradiated with neutrons in a nuclear reactor or in a "neutron oven" to produce a finished multilayer radiation-emitting microsphere containing radiation-emitting palladium-103 or radiation-emitting samarium-145, respectively.

TABLE 1

RADIONUCLIDES FOR LOW ENERGY PERMANANENT MULTILAYERED RADIOACTIVE MICROSPHERES (Main Gamma Energies less than 100 KeV, Half-Life less than 130 days)

| RADIONUCLIDE | HALF-LIFE | MAIN GAMMA ENERGIES |
|---|---|---|
| As-73 | 80.3 days | 53.4 KeV |
| Se-72 | 8.4 days | 46.0 KeV |
| Pd-100 | 3.6 days | 75–84 KeV |
| *Pd-103 | 17.0 days | 39.7 (0.02% 357 KeV) |
| Pd-112 | 21.0 hours | 18.5 KeV |
| *Te-123m | 117.0 days | 88–159 KeV |
| Te-127m | 109.0 days | 88.3 KeV |
| Te-125m | 58.0 days | 35.5 KeV |
| I-125 | 59.9 days | 35.5 KeV |
| *Ce-141 | 33.0 days | 145 KeV |
| *Nd-147 | 10.9 days | 91.1 KeV (13% 531 KeV) |
| Tb-151 | 17.6 hours | 108–731 KeV |
| Tb-155 | 5.3 days | 86.5–105.3 KeV |

*radioisotope can be created by neutron irradiation of corresponding (naturally occurring) isotope, thus allowing manufacture of non-radioactive microsphere with subsequent activation of placing finished product in a "neutron oven".

TABLE 2

RADIONUCLIDES FOR LOW ENERGY PERMANANENT MULTILAYERED RADIOACTIVE MICROSPHERES (Main Gamma Energies less than 100 KeV, Half-Life less than 130 days)

| RADIONUCLIDE | HALF-LIFE | MAIN GAMMA ENERGIES |
|---|---|---|
| Tb-161 | 6.9 days | 25.6–74.6 KeV |
| Dy-166 | 81.6 hours | 82.5 KeV (0.5% 426 KeV) |
| Ho-166 | 1.1 days | 80.6 KeV (0.6% 1.4 MeV) |
| *Er-168 | 9.4 days | 8.42 KeV |
| *Tm-170 | 128.6 days | 84.3 KeV |
| Sb-119 | 36.1 hours | 23.9 KeV |
| Lu-176m | 3.6 hours | 88.3 KeV |
| *Os-191 | 15.0 days | 49–186 KeV |
| Hg-197 | 64.1 hours | 77.4 KeV |
| *Pt-195m | 4.0 days | 31–130 KeV |
| Th-231 | 25.2 hours | 25.6–84.2 KeV (0.2% 108 KeV) |
| Th-234 | 24.1 days | 63.3–92.7 KeV (0.3% 113 KeV) |

*radioisotope can be created by neutron irradiation of corresponding naturally-occurring isotope, thus allowing manufacture of the non-radioactive microsphere with later conversion to the radioactive product by activating the seeds in a "neutron oven".

TABLE 3

RADIONUCLIDES FOR LOW ENERGY PERMANANENT MULTILAYERED RADIOACTIVE MICROSPHERES (Main Gamma Energies less than 100 KeV, Half-Life less than 130 days)

| RADIONUCLIDE | HALF-LIFE | MAIN GAMMA ENERGIES |
|---|---|---|
| Pu-237 | 45.1 days | 59.5 KeV |
| U-231 | 4.2 days | 25.6 KeV (13%) 84.2 KeV (6%) |
| Tl-201 | 3.05 days | Hg K-X-ray |

*radioisotope can be created by neutron irradiation of corresponding naturally-occurring isotope, thus allowing manufacture of the non-radioactive microsphere with later conversion to the radioactive product by activating the seeds in a "neutron oven".

TABLE 4

RADIONUCLIDES FOR HIGH ENERGY PERMANANENT MULTILAYERED RADIOACTIVE MICROSPHERES (Main Gamma Energies greater than 100 KeV, Half-Life Less than 15 to 20 days)

| RADIONUCLIDE | HALF-LIFE | MAIN GAMMA ENERGIES |
|---|---|---|
| K-43 | 22.3 hours | 373 KeV |
| As-74 | 17.8 days | 595 KeV |
| As-77 | 38.8 hours | 239 KeV |
| Sc-47 | 3.4 days | 159 KeV |
| Zr-86 | 16.5 hours | 243 KeV |
| In-111 | 2.8 days | 170–245 KeV |
| Sm-153 | 46.7 hours | 103 KeV |
| Sm-156 | 9.4 hours | 87–204 KeV |
| Eu-157 | 15.2 hours | 64–413 KeV |
| Gd-159 | 18.6 hours | 364 KeV |
| Pb-203 | 2.2 days | 279 KeV |
| V-48 | 15.9 days | 984 KeV |
| Cr-48 | 21.6 hours | 116–305 KeV |
| *Fe-52 | 8.2 hours | 168–377 KeV |

TABLE 5

RADIONUCLIDES FOR HIGH ENERGY PERMANANENT MULTILAYERED RADIOACTIVE MICROSPHERES (Main Gamma Energies greater than 100 KeV, Half-Life Less than 15 to 20 days)

| RADIONUCLIDE | HALF-LIFE | MAIN GAMMA ENERGIES |
|---|---|---|
| Cu-67 | 61.9 hours | 91.2–184 KeV |
| Zn-62 | 9.3 hours | 41.0–596 KeV |
| Ga-67 | 78.3 hours | 93.0–394 KeV |
| Ga-73 | 4.9 hours | 297 KeV |
| Se-73 | 7.1 hours | 67.0–361 KeV |
| Br-77 | 57.0 hours | 87.0–818 KeV |
| *As-76 | 26.5 hours | 559 - KeV |
| Kr-76 | 14.8 hours | 45.5–452 KeV |
| Rb-81 | 4.6 hours | 190–446 KeV |
| Sr-83 | 32.4 hours | 763 KeV |
| Y-87 | 80.3 hours | 388 KeV |
| Mo-99 | 65.9 hours | 144–739 KeV |
| Ru-97 | 2.9 days | 216–461 KeV |
| Rh-105 | 35.4 hours | 306–319 KeV |
| Cd-107 | 6.5 hours | 93–829 KeV |
| Cd-115 | 53.5 hours | 336–528 KeV |
| Sn-110 | 4.0 hours | 283 KeV |
| *Sn-117m | 14.0 days | 159 KeV |

TABLE 6

RADIONUCLIDES FOR HIGH ENERGY PERMANANENT MULTILAYERED RADIOACTIVE MICROSPHERES (Main Gamma Energies greater than 100 KeV, Half-Life Less than 15 to 20 days)

| RADIONUCLIDE | HALF-LIFE | MAIN GAMMA ENERGIES |
|---|---|---|
| Te-119 | 16.0 hours | 644 KeV |
| Te-132 | 78.2 hours | 49.7–228 KeV |
| Cs-127 | 6.2 hours | 412 KeV |
| Cs-129 | 32.3 hours | 371–412 KeV |
| Ag-111 | 7.5 days | 250–340 KeV |
| Te-121 | 16.8 days | 573 KeV |
| I-131 | 8.0 days | 364 KeV |
| Ba-128 | 2.4 days | 273 KeV |
| Ba-131 | 11.8 days | 496 KeV |
| Ba-140 | 12.8 days | 162–537 KeV |
| *Ce-141 | 33.0 days | 145 KeV |
| Ce-134 | 76.0 hours | 605 KeV |
| Ce-137 | 9.0 hours | 447 KeV |
| Nd-138 | 5.1 hours | 199–326 KeV |
| Pm-151 | 28.4 hours | 340 KeV |
| Tb-155 | 5.3 days | 86.5–105.3 KeV |

TABLE 7

RADIONUCLIDES FOR HIGH ENERGY PERMANANENT MULTILAYERED RADIOACTIVE MICROSPHERES (Main Gamma Energies greater than 100 KeV, Half-Life Less than 15 to 20 days)

| RADIONUCLIDE | HALF-LIFE | MAIN GAMMA ENERGIES |
|---|---|---|
| Dy-157 | 8.1 hours | 182–326 KeV |
| Yb-175 | 4.19 days | 114–396 KeV |
| Os-182 | 21.5 hours | 131–510 KeV |
| Os-191 | 15.4 days | 129.4 KeV |
| Pt-184 | 10.2 days | 188–423 KeV |
| Pr-143 | 13.6 days | 742 KeV |
| Eu-157 | 15.2 hours | 413 KeV |
| Gd-149 | 9.3 days | 149–346 KeV |
| Er-169 | 9.4 days | 109–118 KeV |
| Tm-167 | 9.2 days | 208 KeV |
| Tm-173 | 8.2 hours | 398–461 KeV |
| Yb-175 | 4.2 days | 114–396 KeV |

TABLE 8

RADIONUCLIDES FOR HIGH ENERGY PERMANANENT MULTILAYERED RADIOACTIVE MICROSPHERES (Main Gamma Energies greater than 100 KeV, Half-Life Less than 15 to 20 days)

| RADIONUCLIDE | HALF-LIFE | MAIN GAMMA ENERGIES |
|---|---|---|
| Hf-170 | 16.0 hours | 593–621 KeV |
| Hf-171 | 12.1 hours | 122–1,071 KeV |
| Hf-173 | 23.6 hours | 123.6–311.2 KeV |
| Hf-184 | 4.1 hours | 139–345 KeV |
| Re-181 | 20.0 hours | 177–365 KeV |
| Re-188 | 16.9 hours | 155 KeV |
| Re-189 | 24.0 hours | 148–563 KeV |
| Lu-177 | 6.7 days | 113–332 KeV |
| Lu-179 | 4.6 hours | 214 KeV |
| Ta-177 | 2.4 days | 113 KeV |
| Ta-180m | 8.2 hours | 93.3–103 KeV |
| Ta-183 | 5.1 days | 246–354 KeV |
| W-187 | 23.9 hours | 479–685 KeV |
| Ir-189 | 13.2 days | 245 KeV |
| Pt-191 | 2.9 days | 82.4–539 KeV |
| Pt-197 | 18.3 hours | 191.4 KeV |
| Pt-200 | 12.5 hours | 135–330 KeV |

TABLE 9

RADIONUCLIDES FOR HIGH ENERGY PERMANANENT MULTILAYERED RADIOACTIVE MICROSPHERES (Main Gamma Energies greater than 100 KeV, Half-Life Less than 15 to 20 days)

| RADIONUCLIDE | HALF-LIFE | MAIN GAMMA ENERGIES |
|---|---|---|
| Au-193 | 17.6 hours | 112–439 KeV |
| *Au-198 | 2.7 days | 412 KeV |
| Au-199 | 3.1 days | 158–208 KeV |
| Hg-192 | 4.9 hours | 275 KeV |
| Hg-195m | 40.0 hours | 262 KeV |
| Hg-197m | 23.8 hours | 134 KeV |
| Tl-201 | 3.0 days | 135–165 KeV |
| Tl-202 | 12.2 days | 439 KeV |
| Pb-100 | 21.5 hours | 148 KeV |
| Nb-90 | 14.6 hours | 141–2,319 KeV |
| Nb-92m | 10.1 days | 934 KeV |
| Nb-96 | 23.4 hours | 460–1,202 KeV |
| Bk-245 | 4.9 days | 253 KeV |
| Bk-246 | 1.8 days | 799 KeV |
| Es-254m | 1.64 days | 648–693 KeV |
| U-237 | 6.75 days | 59.0 KeV (33%) 208.0 KeV (22%) |

TABLE 10

RADIONUCLIDES FOR TEMPORARY REMOVABLE MULTILAYERED RADIOACTIVE MICROSPHERES (Energy greater than 100 KeV and Half-Life greater than 15 days, or Energy less than 100 KeV and Half-Life greater than 130 days)

| RADIONUCLIDE | HALF-LIFE | MAIN GAMMA ENERGIES |
|---|---|---|
| Be-7 | 53.3 days | 477 KeV |
| Sc-46 | 83.3 days | 159 KeV |
| As-74 | 17.8 days | 595 KeV |
| *Se-75 | 120.4 days | 135–264 KeV |
| Co-57 | 271.0 days | 122 KeV |
| Rb-83 | 86.2 days | 521–529 KeV |
| Sr-85 | 64.8 days | 514 KeV |
| Ti-44 | 47.0 years | 67.8–78.4 KeV |
| Se-75 | 118.5 days | 136–264 KeV |
| Zr-88 | 83.4 days | 393 KeV |
| Zr-93 | $1.5 \times 10^6$ years | 30.4 KeV |
| *Zr-95 | 64.0 days | 724–756 KeV |
| La-138 | $1.06 \times 10^{11}$ years | 788–1,436 KeV |
| Gd-146 | 48.3 days | 115–155 KeV |
| Nb-92 | $3 \times 10^7$ years | 61–935 KeV |
| Nb-93m | 13.6 years | 30.4 KeV |
| Nb-94 | $2.4 \times 10^4$ years | 703–871 KeV |
| Nb-95 | 34.9 days | 766 KeV |
| *Mo-93 | $3.5 \times 10^3$ years | 30.4 KeV |

TABLE 11

RADIONUCLIDES FOR TEMPORARY REMOVABLE MULTILAYERED RADIOACTIVE MICROSPHERES (Energy greater than 100 KeV and Half-Life greater than 15 days, or Energy less than 100 KeV and Half-Life greater than 130 days)

| RADIONUCLIDE | HALF-LIFE | MAIN GAMMA ENERGIES |
|---|---|---|
| Cr-51 | 27 days | 320 KeV |
| *Cd-109 | 450 days | 88 KeV |
| *Cd-115m | 43 days | 935 KeV |
| *In-114m | 50 days | 191–724 KeV |
| *Sn-119m | 250 days | 23–65 KeV |
| *Sn-121m | 76 years | 37 KeV |
| *Sb-124 | 60 days | 443 KeV |
| *Te-129m | 34 days | 487–696 KeV |

TABLE 12

RADIONUCLIDES FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUCLIDE | HALF-LIFE | MAIN GAMMA ENERGIES |
|---|---|---|
| *Ru-103 | 39.3 days | 497 KeV |
| *Ag-107 | 5.0 years | 30–722 KeV |
| Sb-125 | 2.8 years | 427–636 KeV |
| I-129 | $1.6 \times 10^7$ years | 39.6 KeV |
| *Cs-134 | 2.0 years | 604–795 KeV |
| Cs-137 | 30.2 years | 662 KeV |
| Ce-144 | 284.4 days | 134 KeV |
| Pm-143 | 265.0 days | 742 KeV |
| Pm-145 | 17.7 years | 67.2 KeV |
| *Sm-145 | 340.0 days | 61.3 KeV |
| *Sm-151 | 93.0 years | 298 KeV |
| Eu-155 | 4.7 years | 105 KeV |
| Gd-153 | 241.6 days | 69–103 KeV |
| Dy-159 | 144.0 days | 326 KeV |
| *Tb-160 | 73.0 days | 298 KeV |
| *Tm-171 | 1.9 years | 66.7 KeV |
| Lu-173 | 1.4 years | 78–271 KeV |
| Lu-174 | 3.3 years | 76.6 KeV |
| Hf-172 | 1.87 years | 23.9–125 KeV |

TABLE 13

RADIONUCLIDES FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUCLIDE | HALF-LIFE | MAIN GAMMA ENERGIES |
|---|---|---|
| Hf-175 | 70.0 days | 343 KeV |
| *Hf-178m2 | 31.0 years | 88.8–426 KeV |

TABLE 14

RADIONUCLIDES FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUCLIDE | HALF-LIFE | MAIN GAMMA ENERGIES |
|---|---|---|
| Hf-179m2 | 25.1 days | 123–453 KeV |
| *Hf-181 | 42.4 days | 133–482 KeV |
| *Hf-182 | $9 \times 10^6$ years | 114–270 KeV |
| *W-185 | 74.8 days | 125 KeV |
| W-188 | 69.4 days | 63.6–291 KeV |
| Yb-169 | 32.0 days | 63.0–307 KeV |
| Re-183 | 70.0 days | 163 KeV |
| Os-194 | 6.0 years | 42.9 KeV |
| *Ir-192 | 73.8 days | 205–604 KeV |
| Ir-194m | 171.0 days | 328–688 KeV |
| *Hg-203 | 46.6 days | 279 KeV |
| Am-241 | 432.2 years | 59.5 KeV |
| *Bi-210M | 1000.0 years | 300 KeV |
| Am-242m | 141.0 years | 86.5 KeV |
| *Am-243 | $7.4 \times 10^3$ years | 74.7 KeV |
| Cm-241 | 32.8 days | 472 KeV |
| Cm-243 | 28.5 years | 228 KeV |
| Cm-245 | $8.5 \times 10^3$ years | 174 KeV |

TABLE 15

RADIONUCLIDES FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUCLIDE | HALF-LIFE | MAIN GAMMA ENERGIES |
|---|---|---|
| Bk-247 | $1.4 \times 10^3$ years | 83.9–268 KeV |
| Cf-249 | 351 years | 388 KeV |

TABLE 16

RADIONUCLIDES FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUCLIDE | HALF-LIFE | MAIN GAMMA ENERGIES |
|---|---|---|
| U-233 | $1.59 \times 105$ years | 42–97 KeV |
| U-234 | $2.45 \times 105$ years | 53 KeV (0.04% 121 KeV) |
| U-235 | $7.04 \times 108$ years | 185.7 KeV |
| U-236 | $2.34 \times 107$ years | 49.4–112.7 KeV |
| *U-238 | $4.46 \times 109$ years | 49.5 KeV |

TABLE 17

RADIONUCLIDES FOR ELECTRON-PRODUCING
MULTILAYERED RADIOACTIVE MICROSPHERES
High Energy Electron Particle Radiation
without Major Gamma-ray Component

| RADIO-NUCLIDE | HALF-LIFE | PARTICLE | ENERGY | GAMMA COMPONENT |
|---|---|---|---|---|
| Si-32 | 100.0 years | beta – | 213 KeV | — |
| P-32 | 14.3 days | beta – | 1.71 MeV | — |
| P-33 | 25.3 days | beta – | 249 KeV | — |
| Cl-36 | $3.0 \times 105$ years | beta – | 0.71 MeV | — |
| K-40 | $1.3 \times 109$ years | beta – | 1.31 MeV | annihilation rad 1.4 MeV 10% |
| K-42 | 12.4 hours | beta – | 3.52 MeV | 1.5 MeV 18.9% |
| Ca-45 | 163.8 days | beta – | 257 KeV | — |
| Ti-45 | 3.1 hours | beta + | 1.04 MeV | annihilation rad |
| Cu-64 | 12.7 hours | beta – | 578 KeV | annihilation rad |
| | | beta + | 650 KeV | 1.3 MeV 0.6% |
| Bi-210 | 5.0 days | beta – | 1.16 MeV | — |
| Sr-89 | 50.5 days | beta – | 1.49 MeV | 0.9 MeV 0.0009% |
| Sr-90 | 29.0 years | beta – | 546 KeV | — |
| S-35 | 87.2 days | beta = | 167 KeV | — |

TABLE 18

RADIONUCLIDES FOR ELECTRON-PRODUCING
MULTILAYERED RADIOACTIVE MICROSPHERES
High Energy Electron Particle Radiation
without Major Gamma-ray Component

| RADIO-NUCLIDE | HALF-LIFE | PARTICLE | ENERGY | GAMMA COMPONENT |
|---|---|---|---|---|
| Y-90 | 64.0 hours | beta – | 2.28 MeV | — |
| Zr-89 | 78.4 hours | beta + | 0.90 MeV | annihilation rad 1.7 MeV 0.7% |
| Pd-112 | 21.0 hours | beta – | 280 KeV | 18.5 KeV 27% |
| Ag-111 | 7.47 days | beta – | 1.0 MeV | 0.34 MeV 6.7% |
| Cd-113m | 13.7 years | beta – | 590 KeV | 264 KeV 0.02% |
| Cd-115m | 44.6 days | beta – | 1.62 MeV | 1.2 MeV 0.9% |
| In-115 | $4.4 \times 10^{14}$ years | beta – | 348 KeV | — |

TABLE 18-continued

RADIONUCLIDES FOR ELECTRON-PRODUCING MULTILAYERED RADIOACTIVE MICROSPHERES
High Energy Electron Particle Radiation
without Major Gamma-ray Component

| RADIO-NUCLIDE | HALF-LIFE | PAR-TICLE | ENERGY | GAMMA COMPONENT |
|---|---|---|---|---|
| Sn-123 | 129.2 days | beta − | 1.42 MeV | 1.08 MeV 0.6% |
| Cs-135 | 3.0 × 10$^6$ years | beta − | 205 KeV | — |
| Pr-139 | 4.4 hours | beta + | 1.1 MeV | annihilation rad 1.6 MeV 0.3% |
| Pr-143 | 13.6 days | beta − | 935 KeV | 742 KeV 0.00001% |
| Er-169 | 9.6 days | beta = | 340 KeV | — |

TABLE 19

RADIONUCLIDES FOR ELECTRON-PRODUCING MULTILAYERED RADIOACTIVE MICROSPHERES
High Energy Electron Particle Radiation
without Major Gamma-ray Component

| RADIONUCLIDE | HALF-LIFE | PARTICLE | ENERGY | GAMMA COMPONENT |
|---|---|---|---|---|
| Ho-166 | 1.1 days | beta − | 1.8 MeV | 80.5 KeV 6.0% 1.3 MeV 0.90% |
| Tm-170 | 128.6 days | beta − | 883 KeV | 84.3 KeV 3.3% |
| Yb-175 | 4.2 days | beta − | 467 KeV | 396 KeV 6.5% |
| Lu-177 | 6.7 days | beta − | 497 KeV | 208 KeV 11% |
| W-185 | 74.8 days | beta − | 433 KeV | 125 KeV 0.019% |
| W-188 | 69.4 days | beta − | 349 KeV | 291 KeV 0.40% |
| *Tl-204 | 3.8 years | beta − | 763 KeV | — |
| *Bi-210 | 5.0 days | beta − | 1.2 MeV | — |
| Th-231 | 25.2 hours | beta − | 305 KeV | 25.6 KeV 15% 84.2 KeV 6.6% |
| Th-234 | 24.1 days | beta − | 198 KeV | 63.3 KeV 3.8% 92.4 KeV 2.7% |
| Re-186 | 3.7 days | beta = | 1.07 MeV | — |

TABLE 20

MANUFACTURING PARAMETERS FOR LOW ENERGY PERMANANENT MULTILAYERED RADIOACTIVE MICROSPHERES (Main Gamma Energies less than 100 KeV, Half-Life less than 130 days)

| RADIO-NUC | TARGET MATERIAL | ATMOSPHERE GAS | COAT |
|---|---|---|---|
| As-73 | As-73 | Ar | As-73 |
| | As-73 Tribromide | Ar | As-73 Tribromide |
| | As-73 | Ar/Oxygen | As-73 Trioxide |
| | As-73 | Ar/Hydrogen Sulfide | As-73 Trisulfide |
| | Gallium | Ar/As-73H$_3$ | GaAs-73 |
| | Cobalt | Ar/As-73H$_3$ | Co$_2$As-73 |
| | Nickel | Ar/As-73H$_3$ | NiAs-73 |
| | Indium | Ar/As-73H$_3$ | InAs-73 |
| | Iron | Ar/As-73H$_3$ | FeAs-73 |
| | Tungsten | Ar/As-73H$_3$ | W(As-73)$_2$ |
| Se-72 | Se-72 | Ar | Se-72 |
| | Se-72 | Ar/Acetylene | Se-72 Carbide |
| | Se-72 | Ar/Nitrogen | Se-72 Nitride |
| | Se-72 | Ar/Oxygen | Se-72 Oxide |
| | Se-72 | Ar/Hydrogen Sulfide | Se-72 Sulfide |
| | Iridium | Ar/H$_2$Se-72 | Ir(Se-72)$_2$ |
| | Indium | Ar/H$_2$Se-72 | In$_2$(Se-72)$_3$ |
| | Thallium | Ar/H$_2$Se-72 | Tl$_2$Se-72 |

TABLE 21

MANUFACTURING PARAMETERS FOR LOW ENERGY PERMANANENT MULTILAYERED RADIOACTIVE MICROSPHERES (Main Gamma Energies less than 100 KeV, Half-Life less than 130 days)

| RADIO-NUC | TARGET MATERIAL | ATMOSPHERE GAS | COAT |
|---|---|---|---|
| Pd-100 | Pd-100 | Ar | Pd-100 |
| *Pd-103 | Pd-103 | same as Pd-100 | |
| Pd-112 | Pd-112 | same as Pd-100 | |
| Te-123m | Te-123m | same as Te-125m | |
| Te-125m | Te-125m | Ar | Te-125m |
| Te-125m | | Ar/Oxygen | Te-125O$_3$ |
| Gallium | | Ar/H$_2$Te-125 | GaTe-125 |
| Lead | | Ar/H$_2$Te-125 | PbTe-125 |
| Indium | | Ar/H$_2$Te-125 | InTe-125 |
| Platinum | | Ar/H$_2$Te-125 | Pt(Te-125)$_2$ |
| Te-127m | Te-127m | same as Te-125m | |
| I-125 | CuI-125 | Ar | Copper iodide-125 |
| | AgI-125 | Ar | Silver iodide-125 |
| | KI-125 | Ar | Potassium iodide-125 |
| | Ti(I-125)$_2$ | Ar | Titanium di-iodide-125 |
| | Zr(I-125)$_4$ | Ar | Zirconium iodide-125 |
| | Hf(I-125)$_4$ | Ar | Hafnium iodide-125 |
| | Cr(I-125)$_2$ | Ar | Chromium iodide-125 |
| | Dy(I-125)$_3$ | Ar | Dysprosium iodide-125 |
| | Er(I-125)$_3$ | Ar | Erbium iodide-125 |

TABLE 22

MANUFACTURING PARAMETERS FOR LOW ENERGY PERMANANENT MULTILAYERED RADIOACTIVE MICROSPHERES (Main Gamma Energies less than 100 KeV, Half-Life less than 130 days)

| RADIONUC | TARGET MATERIAL | ATMOSPHERE GAS | COAT |
|---|---|---|---|
| I-125 (continued) | Eu(I-125)$_2$ | Ar | Europium iodide-125 |
| | Ho(I-125)$_3$ | Ar | Holmium iodide-125 |
| | Li(I-125) | Ar | Lithium iodide-125 |
| | Lu(I-125)$_3$ | Ar | Lutetium iodide-125 |
| | Nd(I-125)$_3$ | Ar | Neodymium iodide-125 |
| | Rb(I-125) | Ar | Rubidium iodide-125 |
| | Sm(I-125)$_2$ | Ar | Samarium iodide-125 |
| | Tb(I-125)$_3$ | Ar | Terbium iodide-125 |
| | Titanium | Ar/(I-125)$_2$ Ar/HI-125 | Titanium di-iodide-125 |
| | Zirconium | Ar/(I-125)$_2$ Ar/HI-125 | Zirconium iodide-125 |
| | Hafnium | Ar/(I-125)$_2$ Ar/HI-125 | Hafnium iodide-125 |
| | Chromium | Ar/(I-125)$_2$ Ar/Hi-125 | Chromium iodide-125 |
| | Dysprosium | Ar/(I-125)$_2$ Ar/HI-125 | Dysprosium iodide-125 |
| | Erbium | Ar/(I-125)$_2$ Ar/HI-125 | Erbium iodide-125 |
| | Europium | Ar/(I-125)$_2$ Ar/HI-125 | Europium iodide-125 |

TABLE 23

MANUFACTURING PARAMETERS FOR LOW ENERGY PERMANANENT MULTILAYERED RADIOACTIVE MICROSPHERES (Main Gamma Energies less than 100 KeV, Half-Life less than 130 days)

| RADIO-NUC | TARGET MATERIAL | ATMOSPHERE GAS | COAT |
|---|---|---|---|
| | Holmium | Ar/(I-125)$_2$ Ar/HI-125 | Holmium iodide-125 |

TABLE 23-continued

MANUFACTURING PARAMETERS FOR LOW ENERGY PERMANANENT MULTILAYERED RADIOACTIVE MICROSPHERES (Main Gamma Energies less than 100 KeV, Half-Life less than 130 days)

| RADIO-NUC | TARGET MATERIAL | ATMOSPHERE GAS | COAT |
|---|---|---|---|
|  | Lithium | Ar/(I-125)$_2$<br>Ar/HI-125 | Lithium iodide-125 |
|  | Lutetium | Ar/(I-125)$_2$<br>Ar/HI-125 | Lutetium iodide-125 |
|  | Neodymium | Ar/(I-125)$_2$<br>Ar/HI-125 | Neodymium iodide-125 |
|  | Rubidium | Ar/(I-125)$_2$<br>Ar/HI-125 | Rubidium iodine-125 |
|  | Samarium | Ar/(I-125)$_2$<br>Ar/HI-125 | Samarium iodine-125 |
|  | Terbium | Ar/(I-125)$_2$<br>Ar/HI-125 | Terbium iodine-125 |
| *Ce-141 | Ce-141<br>Ce-141 fluoride | same as Ce-134 |  |
| *Nd-147 | Nd-147 | Ar | Nd-147 |
|  | Nd-147 | Ar | Nd-147 bromide |
|  | Nd-147 bromide |  |  |
|  | Nd-147 fluoride | Ar | Nd-147 fluoride |
|  | Nd-147 | Ar/Acetylene | Nd-147 carbide |
|  | Nd-147 | Ar/Nitrogen | Nd-147 nitride |
|  | Nd-147 | Ar/Oxygen | Nd-147 oxide |
|  | Nd-147 | Ar/Hydrogen Sulfide | Nd-147 sulfide |

TABLE 24

MANUFACTURING PARAMETERS FOR LOW ENERGY PERMANANENT MULTILAYERED RADIOACTIVE MICROSPHERES (Main Gamma Energies less than 100 KeV, Half-Life less than 130 days)

| RADIO-NUC | TARGET MATERIAL | ATMOSPHERE GAS | COAT |
|---|---|---|---|
| Tb-155 | Tb-155 | Ar | Tb-155 |
|  | Tb-155 bromide | Ar | Tb-155 bromide |
|  | Tb-155 fluoride | Ar | Tb-155 fluoride |
|  | Tb-155 | Ar/Oxygen | Tb-155 oxide |
| Tb-161 | Tb-161<br>Tb-161 bromide<br>Tb-161 fluoride<br>Tb-161 | same as Tb-155 |  |
| Dy-166 | Dy-166 | Ar | Dy-166 |
|  | Dy-166 bromide | Ar | Dy-166 bromide |
|  | Dy-166 chloride | Ar | Dy-166 chloride |
|  | Dy-166 fluoride | Ar | Dy-166 fluoride |
|  | Dy-166 | Ar/Oxygen | Dy-166 oxide |
| Ho-166 | Ho-166 | Ar | Ho-166 |
|  | Ho-166 bromide | Ar | Ho-166 bromide |
|  | Ho-166 chloride | Ar | Ho-166 chloride |
|  | Ho-166 | Ar/Oxygen | Ho-166 oxide |
| *Er-168 | Er-168<br>Er-168 fluoride | same as Er-169 |  |
| *Tm-170 | Tm-170 | Ar | Tm-170 |
|  | Tm-170 bromide | Ar | Tm-170 bromide |
|  | Tm-170 fluoride | Ar | Tm-170 fluoride |
|  | Tm-170 | Ar/Oxygen | Tm-170 oxide |
| Lu-176m | Lu-176m<br>Lu-176m fluoride | same as Lu-177 |  |

TABLE 25

MANUFACTURING PARAMETERS OF LOW ENERGY PERMANANENT MULTILAYERED RADIOACTIVE MICROSPHERES (Main Gamma Energies less than 100 KeV, Half-Life less than 130 days)

| RADIO-NUC | TARGET MATERIAL | ATMOSPHERE GAS | COAT |
|---|---|---|---|
| Sb-119 | Sb-119 | Ar | Sb-119 |
|  | Tellurium | Ar/Sb-119H$_3$ | (Sb-119)$_2$Te$_3$ |
|  | Indium | Ar/Sb-119H$_3$ | InSb-119 |
| *Pt-195m | Pt-195m<br>Pt-195M phosphide | same as Pt-184 |  |
| Hg-197 | Hg-197 fluoride | Ar | Hg-197 fluoride |
|  | Hg-197 | Ar/Oxygen | Hg-197 oxide |
| Tl-201 | Tl-201 | Ar | Tl-201 |
| Th-231 | Th-231 | Ar | Th-231 |
|  | Th-231 hexaboride | Ar | Th-231 hexaboride |
|  | Th-231 | Ar/Acetylene | Th-231 carbide |
|  | Th-231 | Ar/Oxygen | Th-231 oxide |
|  | Th-231 | Ar/Hydrogen Sulfide | Th-231 sulfide |
|  | Th-231 | Ar/B$_2$H$_6$ |  |
| Th-234 | Th-234<br>Th-234 hexaboride<br>Th-234<br>Th-234<br>Th-234<br>Th-234 | same as Th-231 |  |

TABLE 26

MANUFACTURING PARAMETERS FOR LOW ENERGY PERMANANENT MULTILAYERED RADIOACTIVE MICROSPHERES (Main Gamma Energies less than 100 KeV, Half-Life less than 130 days)

| RADIONUC | TARGET MATERIAL | ATMOSPHERE GAS | COAT |
|---|---|---|---|
| Pu-237 | Pu-237 | Ar | Pu-237 |
| U-231 | U-231 | Ar | U-231 |
|  | U-231 | Ar/B$_2$H$_6$ | U-231B$_2$ |
|  | Boron | Ar/U-231F$_6$ | U-231B$_2$ |

TABLE 27

PARAMETERS FOR HIGH ENERGY PERMANANENT MULTILAYERED RADIOACTIVE MICROSPHERES (Main Gamma Energies greater than 100 KeV, Half-Life Less than 15 to 20 days)

| RADIONUC | TARGET MATERIAL | ATMOSPHERE GAS |
|---|---|---|
| As-74 | As-74 | same as As-73 |
|  | As-74 Tribromide |  |
|  | As-74 |  |
|  | As-74 |  |
|  | Gallium |  |
|  | Cobalt |  |
|  | Nickel |  |
|  | Indium |  |
|  | Iron |  |
|  | Tungsten |  |
| As-77 | As-77 | same as As-73 |
|  | As-77 Tribromide |  |
|  | As-77 |  |
|  | As-77 |  |
|  | Gallium |  |
|  | Cobalt |  |
|  | Nickel |  |
|  | Indium |  |

TABLE 27-continued

PARAMETERS FOR HIGH ENERGY PERMANANENT MULTILAYERED RADIOACTIVE MICROSPHERES (Main Gamma Energies greater than 100 KeV, Half-Life Less than 15 to 20 days)

| RADIONUC | TARGET MATERIAL | ATMOSPHERE GAS |
|---|---|---|
|  | Iron |  |
|  | Tungsten |  |
| Sc-47 | Sc-47 | Ar |

TABLE 28

MANUFACTURING PARAMETERS FOR HIGH ENERGY PERMANANENT MULTILAYERED RADIOACTIVE MICROSPHERES (Main Gamma Energies greater than 100 KeV, Half-Life Less than 15 to 20 days)

| RADIO-NUC | TARGET MATERIAL | ATMOSPHERE GAS | COAT |
|---|---|---|---|
| Zr-86 | Zr-86 | Ar | Zr-86 |
|  | Zr-86 diboride | Ar | Zr-86 diboride |
|  | Zr-86 | Ar/Acetylene | Zr-86 carbide |
|  | Zr-86 | Ar/Nitrogen | Zr-86 nitride |
|  | Zr-86 | Ar/Oxygen | Zr-86 oxide |
|  | Zr-86 | Ar/Hydrogen Sulfide | Zr-86 sulfide |
|  | Zr-86 | Ar/$B_2H_6$ | Zr-86 diboride |
|  | Graphite | Ar/Zr-86$Cl_4$ | Zr-86 carbide |
|  | Boron | AR/Zr-86$Cl_4$ | Zr-86 diboride |
| Sm-153 | Sm-153 | Ar | Sm-153 |
|  | Sm-153 bromide | Ar | Sm-153 bromide |
|  | Sm-153 fluoride | Ar | Sm-153 fluoride |
| Pb-203 | Pb-203 | Ar | Pb-203 |
|  | Pb-203 fluoride | Ar | Pb-203 fluoride |
| V-48 | V-48 | Ar | V-48 |
|  | V-48 | Ar/Acetylene | V-48 carbide |
|  | V-48 | Ar/Nitrogen | V-48 nitride |
|  | V-48 | Ar/Oxygen | V-48 oxide |
|  | V-48 | Ar/Hydrogen Sulfide | V-48 sulfide |
|  | V-48 | Ar/$B_2H_6$ | V-48$B_2$ |
|  | Graphite | Ar/V-48$F_5$ | V-48 carbide |
|  | Boron | Ar/V-48$Cl_4$ | V-48$B_2$ |

TABLE 29

MANUFACTURING PARAMETERS FOR HIGH ENERGY PERMANANENT MULTILAYERED RADIOACTIVE MICROSPHERES (Main Gamma Energies greater than 100 KeV, Half-Life Less than 15 to 20 days)

| RADIO-NUC | TARGET MATERIAL | ATMOSPHERE GAS | COAT |
|---|---|---|---|
| Cu-67 | Cu-67 | Ar | Cu-67 |
|  | Cu-67 fluoride | Ar | Cu-67 fluoride |
|  | Cu-67 | Ar/Oxygen | Cu-67 oxide |
| Ga-67 | Ga-67 | Ar | Ga-67 |
|  | Tellurium | Ar/Ga-67Cl3 | Ga-67 telluride |
| Br-77 | Samarium (Br-77)$_2$ | Ar | Samarium (Br-77)2 |
|  | Neodymium (Br-77)3 | Ar | Neodymium (Br-77)3 |
| Sr-83 | Sr-83 | Ar | Sr-83 |
|  | Sr-83 | Ar/Oxygen | Sr-83 oxide |
|  | Sr-83 | Ar/Acetylene | Sr-83 carbide |
| Y-87 | Y-87 | Ar | Y-87 |
|  | Y-87 chloride | Ar | Y-87 chloride |

TABLE 30

MANUFACTURING PARAMETERS FOR HIGH ENERGY PERMANANENT MULTILAYERED RADIOACTIVE MICROSPHERES (Main Gamma Energies greater than 100 KeV, Half-Life Less than 15 to 20 days)

| RADIO-NUC | TARGET MATERIAL | ATMOSPHERE GAS | COAT |
|---|---|---|---|
| Mo-99 | Mo-99 | Ar | Mo-99 |
|  | Mo-99 | Ar/Acetylene | Mo-99 carbide |
|  | Graphite | Ar/Mo-99$Cl_5$ | Mo-99 carbide |
|  | Graphite | Ar/Mo-99$F_6$ | Mo-99 carbide |
| Ru-97 | Ru-97 | Ar | Ru-97 |
| Rh-105 | Rh-105 | Ar | Rh-105 |
| Cd-115 | Cd-115 fluoride | Ar | Cd-115 fluoride |
|  | Cd-115 | Ar/Oxygen | Cd-115 oxide |
|  | Cd-115 | Ar/Hydrogen Sulfide | Cd-115 sulfide |
| *Sn-117m | Sn-117m | same as Sn-123 |  |
|  | Tellurium |  |  |
| Te-132 | Te-132 | Ar | Te-132 |
|  | Te-132 | Ar/Oxygen | Te-132 oxide |
|  | Gallium | Ar/Te-132$H_2$ | GaTe-132 |
|  | lead | Ar/Te-132$H_2$ | PbTe-132 |
|  | Indium | Ar/Te-132$H_2$ | InTe-132 |
|  | Platinum | Ar/Te-132$H_2$ | Pt(Te-132)$_2$ |
| Cs-129 | Cs-129 bromide | Ar | Cs-129 bromide |
|  | Cs-129 chloride | Ar | Cs-129 chloride |
|  | Cs-129 fluoride | Ar | Cs-129 fluoride |
|  | Cs-129 iodide | Ar | Cs-129 iodide |

TABLE 31

MANUFACTURING PARAMETERS FOR HIGH ENERGY PERMANANENT MULTILAYERED RADIOACTIVE MICROSPHERES (Main Gamma Energies greater than 100 KeV, Half-Life Less than 15 to 20 days)

| RADIONUC | TARGET MATERIAL | ATMOSPHERE GAS | COAT |
|---|---|---|---|
| Ag-111 | Ag-111 | Ar | Ag-111 |
|  | Ag-111 chloride | Ar | Ag-111 chloride |
|  | Ag-111 iodide | Ar | Ag-111 iodide |
|  | Tellurium | Ar/Ag-111$N_3$ | (Ag-111)2Te |
|  | Hg$I_2$ | Ar/Ag-111$N_3$ | (Ag-111)2HgI4 |
| Te-121 | Te-121 | same as Te-132 |  |
|  | Te-121 |  |  |
|  | Gallium |  |  |
|  | Lead |  |  |
|  | Indium |  |  |
|  | Platinum |  |  |
| I-131 | CuI-131 | same as I-125 |  |
|  | AgI-131 |  |  |
|  | KI-131 |  |  |
|  | Ti (I-131)$_2$ |  |  |
|  | Zr (I-131)$_4$ |  |  |
|  | Hf (I-131)$_4$ |  |  |
|  | Cr (I-131)$_2$ |  |  |
|  | Dy (I-131)$_3$ |  |  |
|  | Er (I-131)$_3$ |  |  |
|  | Eu (I-131)$_2$ |  |  |
|  | Ho (I-131)$_3$ |  |  |

TABLE 32

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| I-131 | Li (I-131) | same as I-125 | |
| | Lu (I-131)$_3$ | | |
| | Nd (I-131)$_3$ | | |
| | Rb (I-131) | | |
| | Sm (I-131)$_2$ | | |
| | Tb (I-131)$_3$ | | |
| | Titanium | | |
| | Zirconium | | |
| | Hafnium | | |
| | Chromium | | |
| | Dysprosium | | |
| | Erbium | | |
| | Europium | | |
| | Holmium | | |
| | Lithium | | |
| | Lutetium | | |
| | Neodymium | | |
| | Rubidium | | |
| | Samarium | | |
| | Terbium | | |

TABLE 33

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Ba-128 | Ba-128 chloride | Ar | Ba-128 chloride |
| | Ba-128 fluoride | Ar | Ba-128 fluoride |
| | Ba-128 | Ar/Oxygen | Ba-128 oxide |
| Ba-131 | Ba-131 chloride | same as Ba-128 | |
| | Ba-131 fluoride | | |
| | Ba-128 | | |
| Ba-140 | Ba-140 chloride | same as Ba-128 | |
| | Ba-140 fluoride | | |
| | Ba-140 | | |
| Ce-134 | Ce-134 | Ar | Ce-134 |
| | Ce-134 fluoride | Ar | Ce-134 fluoride |
| | Ce-134 | Ar/Oxygen | Ce-134 oxide |
| Nd-138 | Nd-138 | same as Nd-147 | |
| | Nd-138 bromide | | |
| | Nd-138 fluoride | | |
| | Nd-138 | | |
| | Nd-138 | | |
| | Nd-138 | | |
| *Ce-141 | Ce-141 | same as Ce-134 | |
| | Ce-141 fluoride | | |

TABLE 34

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Pm-151 | Pm-151 | Ar | Pm-151 |
| Tb-155 | see previous Tb-155 entry | | |
| Dy-157 | Dy-157 | same as Dy-166 | |
| | Dy-157 bromide | | |
| | Dy-157 chloride | | |
| | Dy-157 fluoride | | |
| | Dy-166 | | |
| Yb-175 | Yb-175 | Ar | Yb-175 |
| | Yb-175 bromide | Ar | Yb-175 bromide |
| | Yb-175 fluoride | Ar | Yb-175 fluoride |
| *Os-191 | Os-191 | Ar | Os-191 |
| Pt-184 | Pt-184 | Ar | Pt-184 |
| | Pt-184 phosphide | Ar | Pt-184 phosphide |
| Pr-143 | Pr-143 | Ar | Pr-143 |
| | Pr-143 fluoride | Ar | Pr-143 fluoride |
| | Pr-143 | Ar/Oxygen | Pr-143 oxide |

TABLE 35

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Gd-149 | Gd-149 | Ar | Gd-149 |
| | Gd-149 iodide | Ar | Gd-149 iodide |
| Er-169 | Er-169 | Ar | Er-169 |
| | Er-169 fluoride | Ar | Er-169 fluoride |
| Tm-167 | Tm-167 | same as Tm-170 | |
| | Tm-167 bromide | | |
| | Tm-167 fluoride | | |
| | Tm-167 | | |
| Hf-170 | Hf-170 | Ar | Hf-170 |
| | Hf-170 | Ar/Acetylene | Hf-170 carbide |
| | Hf-170 | Ar/Nitrogen | Hf-170 nitride |
| | Hf-170 | Ar/Oxygen | Hg-170 oxide |
| Hf-171 | Hf-171 | same as Hf-170 | |
| | Hf-171 | | |
| | Hf-171 | | |
| | Hf-171 | | |
| Hf-173 | Hf-173 | same as Hf-170 | |
| | Hf-173 | | |
| | Hf-173 | | |
| | Hf-173 | | |

TABLE 36

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Hf-184 | Hf-184 | same as Hf-170 | |
| | Hf-184 | | |
| | Hf-184 | | |
| | Hf-184 | | |

TABLE 36-continued

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Re-181 | Re-181 | Ar | Re-181 |
| Re-188 | Re-188 | same as Re-181 | |
| Re-189 | Re-189 | same as Re-181 | |
| Lu-177 | Lu-177 | Ar | Lu-177 |
| | Lu-177 fluoride | Ar | Lu-177 fluoride |
| Ta-177 | Ta-177 | Ar | Ta-177 |
| | Ta-177 | Ar/Acetylene | Ta-177 carbide |
| | Ta-177 | Ar/$B_2H_6$ | Ta-177 boride |
| | Boron | Ar/Ta-177$F_8$ | Ta-177 boride |
| | Graphite | Ar/Ta-177$F_8$ | Ta-177 carbide |
| Ta-180m | Ta-180m | same as Ta-177 | |
| | Ta-180m | | |
| | Ta-180m | | |
| | Boron | | |
| | Graphite | | |

TABLE 37

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Ta-183 | Ta-183 | same as Ta-177 | |
| | Ta-183 | | |
| | Ta-177 | | |
| | Boron | | |
| | Graphite | | |
| W-187 | W-187 | Ar | W-187 |
| | W-187 | Ar/Acetylene | W-187 carbide |
| | W-187 | Ar/$B_2H_6$ | W-187 Boride |
| | Boron | Ar/W-187$Cl_5$ | W-187 Boride |
| | Graphite | Ar/W-187$F_6$ | W-187 carbide |
| Ir-189 | Ir-189 | Ar | Ir-189 |
| Pt-191 | Pt-191 | same as Pt-184 | |
| | Pt-191 phosphide | | |
| Au-193 | Au-193 | Ar | Au-193 |
| | Tellurium | Ar/Au-193$Cl_2$ | Au-193$Te_2$ |
| *Au-198 | Au-198 | same as Au-193 | |
| | Tellurium | | |

TABLE 38

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Au-199 | Au-199 | same as Au-193 | |
| | Tellurium | | |
| Hg-195m | Hg-195m fluoride | same as Hg-197 | |
| | Hg-195m | | |
| Hg-197m | Hg-197m fluoride | same as Hg-197 | |
| | Hg-197m | | |
| Tl-201 | Tl-201 | Ar | Tl-201 |
| | Vanadium | Ar/$O_2$/Tl-201$NO_3$ | Tl201$VO_3$ |

TABLE 38-continued

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Tl-202 | Tl-202 | same as Tl-201 | |
| | Vanadium | | |
| Pb-100 | Pb-100 | same as Pb-203 | |
| | Pb-100 fluoride | | |
| Nb-90 | Nb-90 | Ar | Nb-90 |
| | Nb-90 | Ar/Acetylene | Nb-90 carbide |
| | Nb-90 | Ar/$B_2H_6$ | Nb-90 boride |
| | Boron | Ar/Nb-90$Cl_5$ | Nb-90 boride |
| | Graphite | Ar/Nb-90$F_5$ | Nb-90 carbide |

TABLE 39

MANUFACTURING PARAMETERS FOR HIGH ENERGY PERMANANENT MULTILAYERED RADIOACTIVE MICROSPHERES
(Main Gamma Energies greater than 100 KeV, Half-Life Less than 15 to 20 days)

| RADIONUC | TARGET MATERIAL | ATMOSPHERE GAS | COAT |
|---|---|---|---|
| Nb-92m | Nb-92 | same as Nb-90 | |
| | Nb-92 | | |
| | Nb-92 | | |
| | Boron | | |
| | Graphite | | |
| Nb-96 | Nb-96 | same as Nb-90 | |
| | Nb-96 | | |
| | Nb-96 | | |
| | Boron | | |
| | Graphite | | |
| Bk-245 | Bk-245 | Ar | Bk-245 |
| Bk-246 | Bk-246 | same as Bk-245 | |
| Bk-247 | Bk-247 | same as Bk-245 | |
| Cf-249 | Cf-249 | Ar | Cf-249 |
| Es-254m | Es-245m | Ar | Es-254m |
| U-237 | U-237 | same as U-231 | |
| | U-237 | | |
| | Boron | | |

TABLE 40

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| Be-7 | Be-7 | Ar | Be-7 |
| | Be-7 | Ar/Nitrogen | Be-7 nitride |
| | Be-7 | Ar/Oxygen | Be-7 oxide |
| | Be-7 | Ar/Acetylene | Be-7 oxide |
| Sc-46 | Sc-46 | same as Sc-47 | |
| Co-57 | Co-57 | Ar | Co-57 |
| | Co-57 fluoride | Ar | Co-57 fluoride |
| | Co-57 | Ar/oxygen | Co-57 oxide |
| Rb-83 | Rb-83 bromide | Ar | Rb-83 bromide |
| | Rb-83 chloride | Ar | Rb-83 chloride |
| | Rb-83 iodide | Ar | Rb-83 iodide |

TABLE 40-continued

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| Sr-85 | Sr-85 | same as Sr-83 | |
| | Sr-85 | | |
| | Sr-85 | | |
| Ti-44 | Ti-44 | Ar | Ti-44 |
| | Ti-44 | Ar/Acetylene | Ti-44 carbide |
| | Ti-44 | Ar/Nitrogen | Ti-44 nitride |
| | Ti-44 | Ar/$B_2H_6$ | Ti-44 boride |
| Cr-51 | Cr-51 | Ar | Cr-51 |
| | Cr-51 | Ar/Acetylene | Cr-51 carbide |
| | Cr-51 | Ar/$H_2S$ | Cr-51 sulfide |

TABLE 41

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Se-75 | Se-72 | same as Se-72 | |
| | Se-72 | | |
| | Se-72 | | |
| | Se-72 | | |
| | Se-72 | | |
| | Iridium | | |
| | Indium | | |
| | Thallium | | |
| Zr-88 | Zr-88 | same as Zr-86 | |
| | Zr-88 diboride | | |
| | Zr-88 | | |
| | Zr-88 | | |
| | Zr-88 | | |
| | Zr-88 | | |
| | Zr-88 | | |
| | Graphite | | |
| | Boron | | |
| Zr-93 | Zr-93 | same as Zr-86 | |
| | Zr-93 diboride | | |
| | Zr-93 | | |
| | Zr-93 | | |
| | Zr-93 | | |
| | Zr-93 | | |
| | Zr-93 | | |
| | Graphite | | |
| | Boron | | |

TABLE 42

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Zr-95 | Zr-95 | same as Zr-86 | |
| | Zr-95 diboride | | |
| | Zr-95 | | |
| | Zr-95 | | |
| | Zr-95 | | |
| | Zr-95 | | |
| | Zr-95 | | |
| | Graphite | | |
| | Boron | | |
| La-138 | La-138 | Ar | La-138 |
| | La-138 | Ar/Oxygen | La-138 oxide |
| | La-138 | Ar/$B_2H_6$ | La-138 boride |
| | Boron | Ar/La-138$Cl_3$ | La-138$B_6$ |
| Gd-146 | Gd-146 | same as Gd-149 | |
| | Gd-146 iodide | | |
| Nb-92 | Nb-92 | same as Nb-90 | |
| | Nb-92 | | |
| | Nb-92 | | |
| | Boron | | |
| | Graphite | | |
| *Cd-109 | Cd-109 fluoride | same as Cd-115 | |
| | Cd-109 | | |
| | Cd-109 | | |
| *Cd-115m | Cd-115m | same as Cd-115 | |
| *In-114m | In-114m | same as In-115 | |

TABLE 43

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Sn-119m | Sn-119m | same as Sn-123 | |
| | Sn-119m | | |
| | Sn-119m | | |
| | Tellurium | | |
| *Sn-121m | Sn-121m | same as Sn-123 | |
| | Sn-121m | | |
| | Sn-121m | | |
| | Tellurium | | |

TABLE 44

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| Nb-93m | Nb-93m | same as Nb-90 | |
| | Nb-93 | | |
| | Nb-93 | | |
| | Boron | | |
| | Graphite | | |

TABLE 44-continued

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| Nb-94 | Nb-94 | same as Nb-90 | |
|  | Nb-94 | | |
|  | Nb-94 | | |
|  | Boron | | |
|  | Graphite | | |
| Nb-95 | Nb-95 | same as Nb-90 | |
|  | Nb-95 | | |
|  | Nb-95 | | |
|  | Boron | | |
|  | Graphite | | |
| *Mo-93 | Mo-93 | same as Mo-99 | |
|  | Mo-93 | | |
|  | Graphite | | |
|  | Graphite | | |
| Sb-125 | Sb-125 | same as Sb-119 | |
|  | Tellurium | | |
|  | Indium | | |
| *Sb-124 | Sb-124 | same as Sb-119 | |
|  | Tellurium | | |
|  | Indium | | |

TABLE 45

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| *Te-129m | Te-129m | same as Te-132 | |
|  | Te-129m | | |
|  | Gallium | | |
|  | Lead | | |
|  | Indium | | |
| *Ru-103 | Ru-103 | same as Ru-97 | |

TABLE 46

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| I-129 | CuI-129 | same as I-125 | |
|  | AgI-129 | | |
|  | KI-129 | | |
|  | Ti (I-129)$_2$ | | |
|  | Zr (I-129)$_4$ | | |
|  | Hf (I-129)$_4$ | | |
|  | Cr (I-129)$_2$ | | |
|  | Dy (I-129)$_3$ | | |
|  | Er (I-129)$_3$ | | |
|  | Eu (I-129)$_2$ | | |
|  | Ho (I-129)$_3$ | | |
|  | Li (I-129) | | |
|  | Lu (I-129)$_3$ | | |
|  | Nd (I-129)$_3$ | | |
|  | Rb (I-129) | | |
|  | Sm (I-129)$_2$ | | |
|  | Tb (I-129)$_3$ | | |
|  | Titanium | | |
|  | Zirconium | | |
|  | Hafnium | | |
|  | Chromium | | |
|  | Dysprosium | | |

TABLE 47

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| I-129 | Erbium | same as I-125 | |
|  | Europium | | |
|  | Holmium | | |
|  | Lithium | | |
|  | Lutetium | | |
|  | Neodymium | | |
|  | Rubidium | | |
|  | Samarium | | |
|  | Terbium | | |
| Cs-137 | Cs-137 bromide | same as Cs-129 | |
|  | Cs-137 chloride | | |
|  | Cs-137 fluoride | | |
|  | Cs-137 iodide | | |

TABLE 48

MANUFACTURING PARAMETERS FOR TEMPORARY REMOVABLE MULTILAYERED RADIOACTIVE MICROSPHERES
(Energy greater than 100 KeV and Half-Life greater than 15 days, or Energy less than 100 KeV and Half-Life greater than 130 days)

| RADIONUC | TARGET MATERIAL | ATMOSPHERE GAS | COAT |
|---|---|---|---|
| Ce-144 | Ce-144 | same as Ce-134 | |
|  | ce-144 fluoride | | |
|  | Ce-144 | | |
| Pm-143 | Pm-143 | Ar | Pm-143 |
| Pm-145 | Pm-145 | same as Pm-143 | |
| *Sm-145 | Sm-145 | same as Sm-153 | |
|  | Sm-145 bromide | | |
|  | Sm-145 fluoride | | |
| Eu-155 | Eu-155 | Ar | Eu-155 |
|  | Eu-155 fluoride | Ar | Eu-155 fluoride |
| Gd-153 | Gd-153 | same as Gd-149 | |
|  | Gd-153 iodide | | |
| Dy-159 | Dy-159 | same as Dy-166 | |
|  | Dy-159 bromide | | |
|  | Dy-159 chloride | | |
|  | Dy-159 fluoride | | |

TABLE 48-continued

MANUFACTURING PARAMETERS FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUC | TARGET MATERIAL | ATMOSPHERE GAS | COAT |
|---|---|---|---|
| *Tm-171 | Tm-171 | same as Tm-170 | |
| | Tm-171 bromide | | |
| | Tm-171 fluoride | | |
| | Tm-171 | | |
| *Sm-151 | Sm-151 | same as Sm-153 | |
| | Sm-151 bromide | | |
| | Sm-151 fluoride | | |

TABLE 49

MANUFACTURING PARAMETERS FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUC | TARGET MATERIAL | ATMOSPHERE GAS | COAT |
|---|---|---|---|
| *Tb-160 | Tb-160 | same as Tb-155 | |
| | Tb-160 bromide | | |
| | Tb-160 fluoride | | |
| | Tb-160 | | |

TABLE 50

MANUFACTURING PARAMETERS FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUC | TARGET MATERIAL | ATMOSPHERE GAS | COAT |
|---|---|---|---|
| Lu-173 | Lu-173 | Ar | Lu-173 |
| | LU-173 fluoride | Ar | Lu-173 fluoride |
| Lu-174 | Lu-174 | same as Lu-173 | |
| | Lu-174 fluoride | | |
| Hf-172 | Hf-172 | same as Hf-170 | |
| | Hf-172 | | |
| | Hf-172 | | |
| | Hf-172 | | |
| Hf-175 | Hf-175 | same as Hf-170 | |
| | Hf-175 | | |
| | Hf-175 | | |
| | Hf-175 | | |

TABLE 50-continued

MANUFACTURING PARAMETERS FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUC | TARGET MATERIAL | ATMOSPHERE GAS | COAT |
|---|---|---|---|
| *Hf-178m2 | Hf-178m2 | same as Hf-170 | |
| | Hf-178m2 | | |
| | Hf-178m2 | | |
| | Hf-178m2 | | |

TABLE 51

MANUFACTURING PARAMETERS FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUC | TARGET MATERIAL | ATMOSPHERE GAS | COAT |
|---|---|---|---|
| Hf-179m2 | Hf-179m2 | same as Hf-170 | |
| | Hf-179m2 | | |
| | Hf-179m2 | | |
| | Hf-179m2 | | |
| *Hf-181 | Hf-181 | same as Hf-170 | |
| | Hf-181 | | |
| | Hf-181 | | |
| | Hf-181 | | |
| *Hf-182 | Hf-182 | same as Hf-170 | |
| | Hf-182 | | |
| | Hf-182 | | |
| | Hf-182 | | |
| *W-185 | Hf-185 | same as W-187 | |
| | Hf-185 | | |
| | Hf-185 | | |
| | Hf-185 | | |
| W-188 | W-188 | same as W-187 | |
| | W-188 | | |
| Re-183 | Re-183 | same as Re-181 | |
| Os-194 | Os-194 | same as Os-191 | |

TABLE 52

MANUFACTURING PARAMETERS FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUC | TARGET MATERIAL | ATMOSPHERE GAS | COAT |
|---|---|---|---|
| *Ir-192 | Ir-192 | same as Ir-189 | |
| Ir-194m | Ir-194m | same as Ir-189 | |
| *Hg-203 | Hg-203 fluoride | same as Hg-197 | |
| | Hg-203 | | |
| *Bi-210m | Bi-210m | same as Bi-210 | |
| | Bi-210m | | |
| | Tellurium | | |
| Am-241 | Am-241 | Ar | Am-241 |
| Am-242m | Am-242m | same as Am-241 | |
| *Am-243 | Am-243 | same as Am-241 | |
| Cm-243 | Cm-243 | Ar | Cm-243 |
| Cm-245 | Cm-245 | same as Cm-243 | |
| U-233 | U-233 | same as U-231 | |
| | U-233 | | |
| | Boron | | |

TABLE 52-continued

MANUFACTURING PARAMETERS FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUC | TARGET MATERIAL | ATMOSPHERE GAS | COAT |
|---|---|---|---|
| U-234 | U-234 | same as U-231 | |
| | U-234 | | |
| | Boron | | |

TABLE 53

MANUFACTURING PARAMETERS FOR TEMPORARY
REMOVABLE MULTILAYERED RADIOACTIVE MICROSPHERES
(Energy greater than 100 KeV and Half-Life
greater than 15 days, or Energy less than 100 KeV
and Half-Life greater than 130 days)

| RADIONUC | TARGET MATERIAL | ATMOSPHERE GAS | COAT |
|---|---|---|---|
| U-235 | U-235 | same as U-231 | |
| | U-235 | | |
| | Boron | | |
| U-236 | U-236 | same as U-231 | |
| | U-236 | | |
| | Boron | | |
| *U-238 | U-238 | same as U-231 | |
| | U-238 | | |
| | Boron | | |

TABLE 54

MANUFACTURE FOR ELECTRON-PRODUCING
MULTILAYERED RADIOACTIVE MICROSPHERES
High Energy Electron Particle Radiation without
Major Gamma-ray Component

| RADIONUC | TARGET MATERIAL | ATMOSPHERE GAS | COAT |
|---|---|---|---|
| Si-32 | Si-32 | Ar | Si-32 |
| | Si-32 | Ar/Acetylene | Si-32 carbide |
| | Si-32 | Ar/Oxygen | Si-32 oxide |
| | Graphite | Ar/Si-32H$^4$ | NiSi-32 |
| P-32 | Platinum (P-32)2 | Ar | Platinum phosphide-32 |
| | Platinum | Ar/H$_{3P-32}$ | Platinum (P-32)$_2$ |
| P-33 | Platinum(P-33)2 | same as P-32 | |
| | Platinum | | |
| Cl-36 | Neodymium (Cl-36)$_3$ | Ar | Neodymium chloride-36 |
| | Holmium (Cl-36)3 | Ar | Holmium chloride-36 |
| K-40 | K-40 chloride | Ar | K-40 chloride |
| | K-40 iodide | Ar | K-40 iodide |
| K-42 | K-42 chloride | same as K-40 | |
| | K-42 iodide | | |
| Ca-45 | Ca-45 | Ar | Ca-45 |
| | Ca-45 fluoride | Ar | Ca-45 fluoride |
| | Ca-45 | Ar/Acetylene | Ca-45 carbide |
| S-35 | Vanadium | Ar/H2$^{S-35}$ | VS-35 |
| | Tungsten | Ar/H2$^{S-35}$ | W(S-35)z |

TABLE 55

MANUFACTURE FOR ELECTRON-PRODUCING
MULTILAYERED RADIOACTIVE MICROSPHERES
High Energy Electron Particle Radiation without
Major Gamma-ray Component

| RADIONUC | TARGET MATERIAL | ATMOSPHERE GAS | COAT |
|---|---|---|---|
| Ti-45 | Ti-45 | same as Ti-44 | |
| | Ti-45 | | |
| | Ti-45 | | |
| | Ti-45 | | |
| Bi-210 | Bi-210 | Ar | Bi-210 |
| | Bi-210 | Ar/Oxygen | Bi-210 oxide |
| | Tellurium | H$_{3Bi}$ | (BI-210) 2Te3 |
| Sr-89 | Sr-89 | same as Sr-83 | |
| | Sr-89 | | |
| | Sr-89 | | |
| Sr-90 | Sr-90 | same as Sr-83 | |
| | Sr-90 | | |
| | Sr-90 | | |
| Y-90 | Y-90 | same as Y-87 | |
| | Y-90 chloride | | |
| Zr-89 | Zr-89 | same as Zr-86 | |
| | Zr-89 diboride | | |
| | Zr-89 | | |
| | Zr-89 | | |
| | Zr-89 | | |
| | Zr-89 | | |
| | Zr-89 | | |
| | Graphite | | |
| | Boron | | |

TABLE 56

MANUFACTURE FOR ELECTRON-PRODUCING
MULTILAYERED RADIOACTIVE MICROSPHERES
High Energy Electron Particle Radiation without
Major Gamma-ray Component

| RADIONUC | TARGET MATERIAL | ATMOSPHERE GAS | COAT |
|---|---|---|---|
| Pd-112 | Pd-112 | same as Pd-100 | |
| Ag-111 | see Ag-111 previous entry | | |
| Cd-113m | Cd-113m fluoride | same as Cd-115 | |
| | Cd-113m | | |
| | Cd-113m | | |
| Cd-115m | Cd-115m fluoride | same as Cd-115 | |
| | Cd-115m | | |
| | Cd-115m | | |
| In-115 | In-115 | Ar | In-115 |
| Sn-123 | Sn-123 | Ar | Sn-123 |
| | Sn-123 | Ar/Oxygen | Sn-123 oxide |
| | Sn-123 | Ar/Hydrogen sulfide | Sn-123 sulfide |
| | Tellurium | Ar/Sn-123H$_4$ | |
| Cs-135 | Cs-135 bromide | same as Cs-129 | |
| | Cs-135 chloride | | |
| | Cs-135 fluoride | | |
| | Cs-135 iodide | | |
| Pr-143 | see previous Pr-143 entry | | |
| Ho-166 | see previous Ho-166 entry | | |

TABLE 57

MANUFACTURE FOR ELECTRON-PRODUCING
MULTILAYERED RADIOACTIVE MICROSPHERES
High Energy Electron Particle Radiation without
Major Gamma-ray Component

| RADIONUC | TARGET MATERIAL | ATMOSPHERE GAS | COAT |
|---|---|---|---|
| Tm-170 | see previous Tm-170 entry | | |
| Yb-175 | see previous Yb-175 entry | | |
| Lu-177 | Lu-177 | | same as Lu-173 |
| | Lu-177 fluoride | | |
| W-185 | W-185 | | same as W-187 |
| | W-185 | | |
| | W-187 | | |
| | Boron | | |
| | Graphite | | |
| W-188 | W-188 | | same as W-187 |
| | W-188 | | |
| | W-188 | | |
| | Boron | | |
| | Graphite | | |
| *Ti-204 | Ti-204 | | same as Ti-201 |
| | Vanadium | | |
| Th-231 | Th-231 | | same as Th-231 |
| | Th-231 hexaboride | | |
| | Th-231 | | |
| | Th-231 | | |
| | Th-231 | | |
| | Th-231 | | |

TABLE 58

MANUFACTURE FOR ELECTRON-PRODUCING
MULTILAYERED RADIOACTIVE MICROSPHERES
High Energy Electron Particle Radiation without
Major Gamma-ray Component

| RADIONUC | TARGET MATERIAL | ATMOSPHERE GAS | COAT |
|---|---|---|---|
| Th-234 | Th-234 | | same as Th-231 |
| | Th-234 hexaboride | | |
| | Th-234 | | |
| | Th-234 | | |
| | Th-234 | | |
| | Th-234 | | |

*footnote for tables 4–58: "Radioisotope can be created from natural element by neutron irradiation of corresponding naturally-occurring non-radioactive isotope, thus allowing manufacture of the finished non-radioactive microsphere with later conversion to the radioactive product by activating the seeds in a 'neutron oven'."

This material of layer 16 is atomically bound to the central section 12 and to the layer above it and in some cases such as sputtered metal layers and their nitrides, carbides or oxides, have hardness and durability that are several times higher than similar bulk metals. Generally, each layer is bound atomically to the material in the layers on either side of it.

The radiation emitting layer 16 may be a radiation emitting compound layer (such as thallium selenide-72, antimony telluride-119, uranium boride-231, zirconium carbide-86, copper iodide-125, mo carbide-99, tantalum carbide-177, vanadium carbide-48, gallium telluride-67, indium telluride-125m, titanium iodide-125, or copper indium selenium-75) laminated with a hard metal %tantalum, tungsten, titanium, hafnium, zirconium, diamond-like carbon, niobium, osmium), metal compound (titanium nitride, titanium carbonitride, zirconium nitride, zirconium carbide, tantalum carbide, tungsten carbide, boron carbide, chromium dicarbide, hafnium carbide, hafnium oxide, lanthanum oxide, thorium carbide, vanadium carbide, hafnium nitride), or nonmetal (diamond or carbon) diffusion barrier. This laminated radiation-emitting coat uniformly covers the solid microspherical metal or carbon core (substrate).

In one embodiment, pure metal is deposited onto microspherical substrates from plasma in an atmosphere containing only an inert gas and a radiation-emitting chemical compound is deposited onto microspherical substrates when a radiation-emitting reactive gas such as a radioactive hydride gas is introduced into the system to form a radioactive compound from the metal and gas. In another embodiment, cycles of different coating materials are alternated to produce a laminate of thin hard (high boiling point metal) and soft (radiation-emitting compound) coats such as for example of the materials described above. Using adequate biasing of the substrate, each cycle is approximately thirty seconds in duration so that one layer of radiation-emitting compound is sealed by one layer of pure (high boiling point) metal each sixty seconds.

Depending on the materials being coated and the efficiency of the deposition apparatus, each alternate layer is approximately 100 Angstroms to 1000 Angstroms thick, depending on the coating method used as well as the apparatus and atomic weights of the elements being coated. The coating of the soft radiation-emitting layer with a hard-metal layer seals the radiation-emitting layer before it begins to break or vacuum weld with other microspheres. This is continued using one of the coating methods outlined hereinafter until the desired activity or radiation-emitting compound is accumulated on the microsphere. A laminate of thin hard (metal nitride, metal oxide, metal carbide, or metal carbonitride) and soft (metal-radionuclide compound) coats are produced.

The outer layers 18 and 20 confine the radiation-emitting layer 16. In one embodiment, these layers are made of a material that permits the transmission of electrons through them such as carbon thus permitting electron seeds by the appropriate selection of the material for the layer 16 but in other embodiments are made of metals that are hard and protective but absorb or filter electron particles. These materials in layers 18 and 20 are included in embodiments with radiation-emitting materials in the layer 16 to protect, seal, identify and under some circumstances provide filtering of radiation.

In some embodiments, the layer 18 is a diffusion barrier that prevents the movement of radioactivity outwardly toward the suface of the microsphere 10. The outer layer may serve as both diffusion barrier and provide mechanical protection or color identification if desired. The material of the diffusion barrier is selected for its functions in conduction with the nature of the material that provides the radiation.

Suitable diffusion barriers include: (1) single metals such as gold, palladium, tantalum, tungsten, platinum, and titanium; or (2) multilayered combinations of metals such as gold-palladium-titanium, gold-titanium and tungsten-titanium; or (3) compounds such as titanium nitride (TiN), and titanium carbide (TiC), tungsten carbide (WC), tungsten nitride (WN), tungsten-titanium nitride (TiWN), hafnium nitride (HfN), hafnium carbide (HfC), zirconium nitride (ZrN), zirconium carbide (ZrC), vanadium carbide (VC), boron carbide (BC) and tungsten boride (WB); or (4) nonmetallic elements or compounds such as diamond or diamond-like carbon.

The preferred diffusion barrier materials of the present invention are titanium nitride, tungsten carbide, hafnium nitride and groups of layers such as a titanium layer 100 nm (nanometers) thick, a layer of palladium 100 nm thick, and a layer of gold 300 nm thick. The purpose of the diffusion barrier is to prevent difusion of the radiation-emitting component into the outer coats of the multilayer radiation-emitting microsphere. It also serves as a radiation-emitting gas barrier for radionuclides which sublimate or form gases at room temperature.

An essential criterion of thin film structures is that they maintain structural integrity. Pronounced reaction or interdiffusion of thin films is known to occur over short distances of several hundred angstroms. Thin metal layers tend to diffuse and react chemically, and this tendency is enhanced by thin film defects or grain boundaries. The diffusion barrier helps prevent this diffusion.

It is important to prevent radiation-emitting materials from diffusing through the outer metal coats of the multi-layer radiation-emitting microsphere because metals such as I-125 can sublimate into a gas upon exposure to air, or if they are implanted into a patient, the I-125 can enter the bloodstream and become concentrated in the thyroid gland. Diffusion barriers are not necessary when the radionuclide element is a chemically stable or high boiling point metal or metal compound that is relatively inert.

To further reduce leakage of radioactive material, a layer of metal that chemically reacts with the material in the radioactive layer may be sputtered or otherwise coated over the radioactive material as a chemical diffusion layer before the mechanical diffusion layer. This layer reacts with the reactive material and seals the mechanical diffusion layer. For example, silver may be sputtered as an even coat over the reactive iodide layers to reduce leakage. Moreover, the density of the diffusion layer and its uniformity is maximized, such as by coating the diffusion layer on using the lowest possible pressure and introducing as much energy as feasible while avoiding welding of microspheres, such as by the introduction of a magnetic field and heat during the coating process.

The outer coat 20 is a thick spherical (up to 0.10 mm) protective coat containing the inner coats 16 and 18. The spherical thick protective coat may be composed of: (1) a resistant human tissue-compatible metal which also has low atomic weight to minimize X-ray shielding such as titanium or other corrosion-resistant metal alloy such as stainless steel; or (2) a resistant human tissue-compatible metal compound (using reactive acetylene nitrogen, oxygen, methane, or carbon monoxide gases during coating to form carbides, nitrides, or carbonitrides of transition metals or other metals) such as titanium carbide, titanium nitride, titanium carbonitride, titanium aluminum nitride, zirconium nitride and hafnium nitride; or (3) a resistant human tissue-compatible metal coat less than 0.1 millimeters thick which has a high atomic weight such as tantalum, platinum or gold; or (4) a human tissue-incompatible metal coat which is covered by a tissue-compatible thin coat.

If a tissue-compatible outermost coat such as sputtered diamond, tantalum, or titanium is applied over the thick protective metal casing, then the more toxic but low atomic weight metals such as beryllium, vanadium, nickel and boron nitride may be used as the thick casing. Appropriate outermost coat are typically thin and consist of a special-purpose coat designed to enhance physical properties of the seed such as diamond or diamond-like carbon, platinum, or tantalum. These coats individually enhance the multilayer radiation-emitting microsphere by adding hardness, and corrosion resistance. The outermost thin coat may also be used to produce different seed identification colors.

To produce color, the outermost thin coat may include of titanium nitride (TiN) to produce a golden color, titanium carbonitride (TiCN) to produce a brown color, titanium aluminum nitride (TiAlN) to produce a black color, titanium carbide (TiC) to produce a gray color, zirconium nitride (ZrN) to produce a silver-yellow color, and hafnium nitride (HfN) to produce a yellow-green color.

Some appropriate strong hard corrosion-resistant human tissue-compatible metal include titanium, hafnium, and zirconium. Low atomic weight metal alloys such as stainless steel are also satisfactory. Other usable corrosion-resistant metals include tantalum, tungsten, gold, and platinum. Because this "thick" layer is still relatively thin (less than 0.1 mm) and because the coat is highly uniform and spherical, a high atomic weight metal such as platinum or gold may still be effectively used as the thick protective coat without causing radiation aniostropy and with minimal gamma-ray shielding and loss of radioactivty.

Because of spherical uniform construction, any self-shielding can be compensated for by increasing the seed activity. In the preferred embodiment of this invention, metals having low atomic weight with minimal shielding of low-energy gamma rays, tissue and corrosion resistance, high hardness and high boiling point are preferred for the casing of multilayer radiation-emitting microsphere's containing low energy emitting (less than 100 KeV) radionuclides. Titanium is such a metal. The preferred metal for casings of multilayer radiation-emitting microsphere's containing high energy emitting (greater than 100 KeV) radionuclides have high atomic weight with some shielding of low energy gamma rays and very little shielding of high energy gamma rays, high tissue and corrosion resistance, high hardness and very high boiling point. Two such metals are tantalum and tungsten.

The casing 20 also may include a strong hard corrosion-resistant human tissue-compatible non-metallic element. The preferred non-metallic thick protective coat is sputtered or plasma-deposited diamond or plasma-deposited diamond-like carbon. These non-metallic coats not only have the advantage of low atomic weight to minimize X-ray self-shielding of the radionuclide layer, but they also have the advantage of being completely non-ferromagnetic.

Other hard corrosion-resistant metals include carbides, metal nitrides, metal borides, metal oxides, metal sulfides, or metal carbonitrides. The preferred metallic compound thick protective coats of the present invention include titanium carbide, titanium nitride, titanium carbonitride, tantalum carbide, tungsten carbide, hafnium nitride, and zirconium nitride.

All of these thick coats may be incorporated individually into different seed designs to adequately serve as a hard crush-resistant corrosion-resistant protective outer casing of the multilayer radiation-emitting microsphere. All of these coats may be easily applied by the standard deposition or reactive deposition techniques described elsewhere.

Additionally, if a tissue-compatible outermost coat such as sputtered diamond, tantalum, or titanium is applied over the thick protective metal casing, then the thick protective layer need not be composed of a tissue-compatible material. Tn this case, more toxic but low atomic weight metals such as beryllium, vanadium, nickel and boron nitride may be used as the thick protective casing.

In FIGS. 2–5, there are shown four other embodiments of radiation-emitting microspheres 10A, 10B, 10C and 10D respectively having corresponding layer sections 14A–14D with different numbers of and/or thicknesses of its layers or coats, ranging from four coats to five coats but normally with one thick protective coat and several thin coats so as to minimize the diameter of the radiation-emitting microsphere. The microsphere 10A of FIG. 2 has a hollow substrate 12A but would include a solid spherical substrate instead. For convenience the coats are numbered from the center outwardly regardless of their specific composition or use. The extra layers are an optional special-purpose inner spherical coat designed to enhance diagnositc X-ray or magnetic resonance or PET imaging and an optional thin outermost special-purpose coat.

Figure 4:
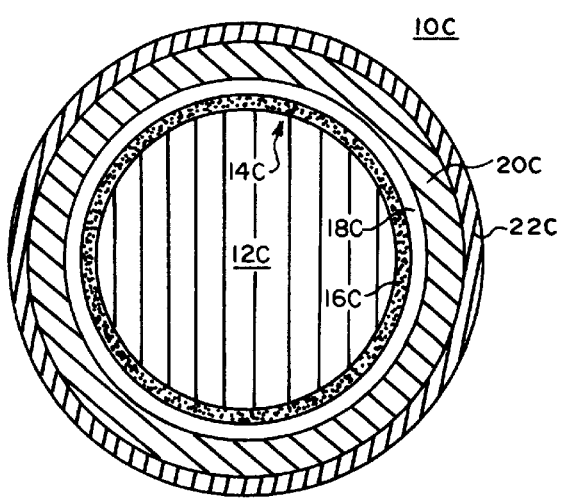
FIG. 4 is a sectional view of still another embodiment of multilayer radioactive microsphere.
Figure 5:
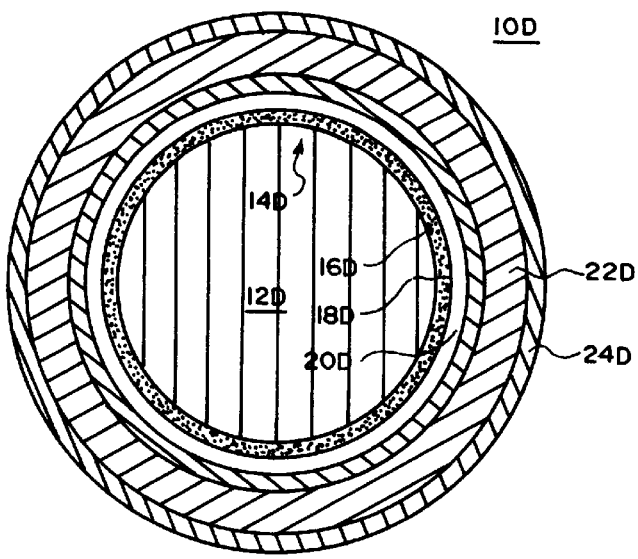
FIG. 5 is a sectional view of still another embodiment of multilayer radioactive microsphere.

The optional thin (less than 0.01 mm thick) outermost special-purpose coat is shown at 22C in FIG. 4 and at 24D in FIG. 5. This optional outer coat may be dc, rf, laser ablation or magnetron sputtered, ion-plated, ion-beam sputtered, or curvilinear or standard cathodic arc plasma deposited materials such as diamond, diamond-like carbon, titanium nitride, titanium carbonitride, titanium carbide, tantalum carbide, hafnium nitride, zirconium nitride, platinum, or tantalum. These coats individually produce additional desirable multilayer radiation-emitting microsphere physical characteristics such as increased hardness, scratch resistance, colors used for identification, reduced friction, increased tissue comparability, and increased corrosion resistance that enhance the basic spherical sputtered laminated multilayer radiation-emitting microsphere design of the present invention.

Optional thin outer multilayer radiation-emitting microsphere coats may be used to produce different seed identification colors to clearly label seeds of differing compositions or to differentiate seeds with low versus high activities, long versus short half-lives, or low versus high gamma energies. These layers must not only produce colors but they must also be tissue compatible and corrosion resistant, because they are the outermost layer of the multilayer radiation-emitting microsphere.

Diamond coated multilayer radiation-emitting microsphere's are less likely to be damaged by surgical instrumentation. Also, reduced friction of this surface coat makes the multilayer radiation-emitting microsphere of the present invention less likely to jam in an autofeeding tissue implantation gun. A thin layer of diamond (less than 0.001 mm) thick produced by reactive cathodic arc deposition from a carbon-containing gas is a preferred optional thin outer multilayer radiation-emitting microsphere coat of the present invention.

If necessary, to reduce porosity or remove crystallization of the coats of the finished product, or to improve adhesion between layers, after completion of coat, the multilayer radiation-emitting microsphere's may be annealed in a separate apparatus. In some embodiments, this may be done by heating close to the bulk metal melting temperature in a microsphere bouncing pan and thus result in a fine crystal structure typical of annealed materials.

The optional inner spherical uniform special purpose coats may he used to enhance imaging of the multilayer radiation-emitting microsphere by conventional radiographs, computed tomography or magnetic resonance imaging or other remote imaging arrangements. It may be a relatively thin (less than 0.01 mm thick) rf, magnetron, laser ablation or dc sputter-deposited, or ion-plated, or ion-beam self-sputtered, curvilinear cathodic arc plasma deposited or standard cathodic arc plasma deposited layer for diagnostic X-ray imaging enhancement or magnetic resonance imaging enhancement or positron emission imaging enhancement (PET) or single position emission computed topography (SPECT) for seed identification.

A coat such as gadolinium, erbium, terbium, thulium, cerium, cobalt fluoride, dysprosium oxide, dysprosium sulfide, neodymium fluoride, terbium oxide, samarium bromide, thulium oxide, etc. is chosen for the purpose of magnetic resonance imaging because of their properties of paramagnetism and high magnetic susceptibility as well as high-boiling point that reduces vacuum welding during coat deposition.

Elements or compounds that are suitable for the magnetic resonance imaging layer of the present invention include cerium (B.P. 3,468 C, magnetic susceptibility (ms) in $10^{-6}$ cgs ms +5,160.0), cobalt fluoride (B.P. 1,400 C, ms +9 , 490.0), dysprosium oxide (M.P. 2,340 C, ms +89,600.0), dysprosium sulfide (M.P. - - - , ms +95,200.0), erbium (B.P. 2,900 C, ms +44,300.0) gadolinium (B.P. 3,000 C, ms +75,000.0), manganese dichloride (B.P. 1,900 C, ms +14, 300.0), neodymium fluoride (B.P. 2,300, ms +4,980.0), samarium bromide (B.P. 1,880, +5,337.0), terbium (B.P. 2,800 C, ms +146,000.0), terbium oxide (B.P. - - - , ms +78,340.0), thulium (B.P. 1,727 C, ms +25,000.0), thulium oxide (B.P. - - - ms +51,444.0).

Because these elements have sufficiently high boiling points to be effectively coated onto the multilayer radiation-emitting microsphere of the present invention, and because they have significantly different magnetic susceptibilities, it is possible to separately identify different multilayer radiation-emitting microsphere's coated with different magnetic resonance imaging imaging agents within the same tumor for purposes of tumor dose calculations. This is significant because, to take full advantage of the wide variety of multilayer radiation-emitting microsphere's of the present invention, it is advantageous to implant more than one type of multilayer radiation-emitting microsphere in one procedure into the same tumor.

To be discharged from a hospital, a patient with permanently-implanted radiation-emitting seeds must wait until the total activity of the seeds falls below a permissible level specified for that particular radionuclide. Using short-lived radionuclides, these radiation-emitting activity levels can be obtained within a reasonable number of days, thus avoiding excessively long hospitalization, while still delivering adequate tumor dose.

The central sphere or other coats may be formed of a material that is heatable by remotely radiated energy for hyperthermia and/or a magnetic material that enables force to be applied to the seed to move it around using externally radiated energy to avoid damage to tissue. For example, ferromagnetic materials may be used that are heated by induced radio frequency energy to the Curie temperature and have a Curie temperature appropriate for hyperthermia such as, for example, 50 degrees Centigrade. Moreover, a strongly magnetic material may cause movement of the seed by externally applied electromagnetic fields.

Substrate cores composed of a suitable ferromagnetic alloy or paramagnetic or ferroelectric compounds in the form of microspheres that have a sharp Curie transition in the range of 40 to 50 degrees Centigrade may be manufactured in situ by coating a starting seed with a ferromagnetic compound such as by sputtering, laser ablation or cathodic arc deposition using the appropriate target materials and/or reactive gases or by making the entire seed of the appropriate material. Elements suitable for Curie-transition-point substrate microspheres for use in the present invention include iron, cobalt, nickel, dysprosium and gadolinium. Other alloys can be formed to have the proper Curie point.

Elements and compounds are combined in optimal proportions to produce a final seed that has a sharp Curie transition point in the range of 42 degrees Centigrade to 50 degrees Centigrade. The compounds and elements may be alloyed in situ by sputtering from the appropriate shuttered targets. Differential shuttering of the targets permits control of the sputtering rate of each target, and permits precise control of the percentages and proportions of target materials alloyed onto the substrate microspheres. Similarly, the proportions can be easily controlled using laser ablation techinques, wherein a laser is used to vaporize one or several sputtered targets.

For example, the nickel series of alloys can be used to produce microspherical substrates with Curie transition points in the range of 42 to 50 degrees Centigrade. These include: Vanadium 4%+Nickel 96%; Molybdenum 6%+Nickel 94%; Chromium 8%+Nickel 92%; Titanium 9%+Nickel 91%; Sb 7%+Nickel 93%; Silicon 8%+Nickel 92%; Aluminum 12%+Nickel 88%; Platinum 28%+Nickel 72%; Manganese 17%+Nickel 83%; Copper 29%+Nickel 71%.

Although the embodiments of FIGS. 1–5 show from three to five coats, a seed may be formed of a 0.20 mm diameter tantalum center, a 0.01 mm to 0.045 thick Ti (I-125)2/TiN inner coat and a 0.05 mm thick titanium nitride outer coat. This structure is possible because the TiN serves as both a diffusion barrier and as a protective coat, thus removing the need for another diffusion barrier coat.

Instead of a radioactive layer, radiation hazards can be reduced by utilizing a coat of non-radioactive material, either naturally occurring or isotopically enhanced material that is one neutron away from being a stable radioactive isotope. This material may then be activated by neutron eradiation just before being used to avoid forming seeds with higher radioactivity than needed and permitting them to decay until used or using radioactive seeds that may not be at their optimum radioactivity because of the lapse of time since formation. The material should have a thickness range of 25 microns to 50 microns (0.025 mm to 0.050 mm) when the starting material is a non-enriched natural element that is converted to the corresponding radioactive isotopes by thermal neutron bombardment. The amount of material is related to the amount of radioactivity that can be produced by neutron eradiation of the element.

In use, the multilayer radioactive microspheres are surgically implanted, either permanently by placing them directly into the tissue, or temporarily by placing them in catheters, or removable tubes, etc. One surgical technique for implantation of multilayer radioactive microspheres includes selecting the half-life, energy, activity and field strength of the implant in accordance with the time of implantation, implanting the high energy microspheres and removing high energy microspheres after a time period long enough to destroy only neoplastic tissue and not long enough for the destruction of differentiated healthy cells in accordance with the intensity of the radiation. However, if the high energy microsphere has a relatively short half-life, it need not be removed and may be permanently implanted. Also, low-energy miscrospheres are not hazardous to others because the energy is almost completely absorbed within the patient. Thus, low-energy microspheres are usually permanently implanted, unless a high dose rate is desired. Even for temporary implants, low-energy implants are less hazardous to hospital personnel.

A plurality of low energy microspheres may be implanted at distances from each other in accordance with the intensity wherein only neoplastic tissue is destroyed by physically confining the major radiation dose to the neoplastic tissue by virtue of the physical characteristics of the microspheres. An auto-feeding implantation gun may be used.

In one form of treatment, between 30 and 300 low activity multilayer radioactive microspheres are implanted permanently into a human tumor at approximately 1 centimeter intervals throughout the volume wherein continuous-low-dose rate low energy irradiation is produced at less than 1.5 Gray per hour. In conjunction with the implant, minimum doses of 80 to 3,000 Gray to the tumor volume over the average lifetime of the multilayer radioactive microsphere may be delivered.

The idea of synchronizing cells prior to radiation therapy has been tried clinically by utilizing chemotherapy agents as cell synchronizing agents. For example, hydroxyurea has been tried as a cell synchronizing chemical agent prior to external beam irradiation in the treatment of cervical cancer and malignant glioblastomas of the brain. These trials have been only moderately successful or unsuccessful.

An "inverse dose-rate effect" has been described in which decreasing the dose rate of radiation delivery results in increased cell killing. This paradoxic effect has been explained by the fact that at certain dose rates, cells tend to progress through the cell cycle and become arrested in G-2 or G-2/S, a very radiosensitive phase of the cell cycle. Further continuous low-dose rate irradiation of these "arrested and radiosensitized" cells then results in very effective cell killing, far beyond that expected from the relatively low radiation doses delivered.

The actual dose-rates that produce this effect vary widely for different cell lines. The dose-rates that effectively produce a G-2 block for a given tumor type can be determined experimentally by culturing tumor cells and analyzing the cell-cycles using standard flow-cytometry techniques. It can also be determined by trial and error with a patient. It has been determined by one investigator that the minimum dose-rate necessary to stop cell division of HeLa cells was approximately 23 rad/hour, but it was approximately 270 rad/hour for V-79 cells—a ten-fold difference.

For these "optimum" dose rates that stopped cell division, all the cells were noted to progress through G-1 and S-phase, with a small delay in S-phase, followed by complete block in G-2 phase. HeLa cells showed a dramatic effect of redistribution of cells into sensitive phases of the cell cycle during exposure, which was reflected in the survival curves at low dose rate, and more cell killing per unit dose was observed at 37 rad/hour than at 74 rad/hour. Thus, at the optimal dose rate, cells tend to progress through the cell cycle and become arrested in G-2, a known radiosensitive phase of the cell cycle. While so arrested, they may be more efficiently killed by delivery of further radiation. At higher dose rates, cells are "frozen" in the phase of the cycle they are in at the start of irradiation. At lower-than-optimal dose rates, the cells escape the G-2 block and proceed to cycle and divide as usual during irradiation.

Each tumor-type has a characteristic "optimal-dose rate" that produces prolonged cell cycle arrest in the radiosensitive G-2 phase. This "optimal-dose-rate" can be determined using standard cell culture and cell-cycle analytic techniques. Bedford and Mitchell noted that dose rates of 38 rads per hour for HeLa cells and 90 rads per hour for V-79 Chinese hamster cells essentially prevented cell division, but such continuous irradiation had no effect upon the progress of cells through G-1 or S-phase, but produced a G-2 delay and prevented cell division.

The multilayer radioactive microspheres disclosed in the present invention can be matched (by producing multilayer radioactive microspheres with specifically matched energies, half-lives, and activities) to a particular tumor to produce this "optimal-dose-rate" throughout the tumor target volume, and cause a prolonged block at G-2, and thus serve as a "radiosensitizer" if present during administration of a conventional course of external-beam irradiation. In other words, the multilayer radioactive microspheres disclosed in the present invention can be manufactured to "match" the radiobiology of a particular tumor and thus produce an "optimal" dose rate of continuous irradiation and thus serve as a "radiosensitizer" by blocking the cells within the tumor target volume in the G-2 phase of their cell cycles.

Percutaneous needle biopsy using either CT (computed tomography) or sonographic (ultrasound) guidance is a common procedure that has been developed over the past 15 years. In the early years of radiologically guided needle biopsy, most biopsies were performed using thin-caliber (21-gauge to 22 gauge) needles which provided a known wide margin of safety. The use of thin-gauge needles to perform biopsies is historically associated with the lowest risk of bleeding and tissue trauma. Even overlying loops of stomach or small intestine are not a contraindication to needle biopsy if small-caliber thin-gauge needles are used. The most common human body sites in which radiologically guided biopsy has been performed include the liver, pancreas, retroperitoneum, adrenal gland, pelvis, chest, bone, extremity, and neck.

Because of its small size, (usually less than 0.40 mm diameter) the multilayer radioactive microspheres of the present invention can be easily and safely implanted into almost any body site using a small-caliber thin-gauge (21 G to 22 G) interstitial implantation needle using the same techniques initially developed to perform percutaneous needle biopsies under CT and sonographic guidance. Additionally, multilayer radioactive microspheres of the present invention can be implanted using MRI guidance (magnetic resonance imaging).

The relatively recent use of computers to digitize the relative spatial coordinates of human body organs derived from CT, MRI, and PET (positron emission tomography) scans and produce three-dimensional images (Scandiplan, Scanditronix Inc, Uppsula, Sweden) could be utilized to stereotactically implant multilayer radioactive microspheres into specific body sites using such digitized data to guide the interstitial needle to specific Cartesian or polar body coordinates in relation to a reference system. While stereotactic frames have been used extensively in the past to perform neurosurgical procedures, stereotactic techniques have not been used in the past to implant radioactive seeds into body sites other than the brain, pituitary, or skull base. However, such stereotactic techniques may be applied to implant multilayer radioactive microspheres into any body site in a "stereotactic body-implantation" system using either a "stereotactic frame" or a "robotic-arm".

Stereotactic brain surgery is a technique for guiding the tip of a probe into the brain through a hole drilled in the skull without having direct visualization of the surgical site. Such techniques have been developed and applied in the field of neurosurgery. Stereotactic surgical frames have been coupled with CT scanners since any point identifiable on a CT scan can be related to stereotactic coordinates, allowing stereotactic guidance of surgical instruments for biopsy or neurosurgical procedures. There are numerous geometrical systems upon which stereotactic frame coordinates could be based.

The four main types of frames developed to date include: (1) polar coordinate; (2) arc-radius; (3) focal point; (4) phantom target. A typical polar coordinate stereotactic system requires that a trajectory is described in polar coordinates relative to an entry point. Arc radius frames employ a probe in a semicircular arc which is introduced orthogonal to a tangent along the arc. Phantom or "dummy" devices may use any coordinate system to determine the angles and probe lengths of a stereotactic device mechanically rather than trigonometrically. This approach may be used to implant microspheres at the selected locations.

A new teqhnique in which a commercially available robot (Unimation Puma 200 robot) performs a "robotic stereotactic" brain biopsy is known. Spatial information determined by CT scanning is tied into a base frame used to immobilize the patient, and this information is translated into robotic spatial coordinates that are used to direct the robotic arm and biopsy needle to the proper location.

Robotic stereotactic techniques may be applied to implant multilayer radioactive microspheres into any body site in a "robotic body-implantation" system without relying upon a "stereotactic-frame". The primary use of multilayer radioactive microspheres and related products is the safe delivery of high tumoricidal radiation doses to human tumors that are two to five times higher than those achievable by conventional external-beam radiation therapy. A second use of multilayer radioactive microspheres is the clinical use of multilayer radioactive microspheres as radiation sensitizers to enhance the tumor-effect of a conventional course of external-beam radiation therapy.

Generally, the primary use of multilayer radioactive microspheres is to permit safe delivery of tumoricidal doses of radiation that are two to five times higher than that deliverable by external means. In the first application of multilayer radioactive microspheres, the total dose delivered is the critical factor, and this dose must be completely tumoricidal. The second use of multilayer radioactive microspheres of the present invention includes the use of multilayer radioactive microspheres radiation as a radiation sensitizer in the sense that continuous low dose rate irradiation produced by multilayer radioactive microspheres optimally synchronizes tumors and causes cells to remain blocked in the radiosensitive portion of their cell cycles. In this secondary application, the dose of radiation delivered by the seed is not critical, and in most cases it may not even be substantially tumoricidal. However, the tumor volume dose rate is critical, and it must be high enough to hold cells in the G-2 block 24 hours per day, but it must be low enough to permit cells to progress through their cell cycles until they come to G-2. An excessively high dose rate would result in immobilization of all cells at their particular points within their cell cycles and is an undesirable effect.

Because of their small diameters, the multilayer radioactive microspheres of the present invention may be implanted using thin-caliber 21-Gauge or 22-Gauge needles using either CT, MRI, or sonographic guidance techniques originally developed in the field of radiology to perform percutaneous needle biopsies.

Stereotactic techniques developed and applied to the field of neurosurgery are now applied to all body sites to permit stereotactic implantation of multilayer radioactive microspheres of the present invention into any body site. A stereotactic body frame is introduced for implantation of multilayer radioactive microspheres using CT or MRI guidance.

Robotic techniques developed and applied to the field of neurosurgery are now applied to all body sites to permit robotic implantation of multilayer radioactive microspheres of the present invention Into any body site. A robotic multilayer radioactive microspheres implantation system is introduced for implantation of multilayer radioactive microspheres using CT or MRI guidance coupled to a robotic arm without a stereotactic frame.

Multilayer radioactive microspheres implanted into human tumor tissues whether permanently or temporarily, are used to deliver tumoricidal radiation doses that are two to five times higher than those achievable using conventional external-beam radiation therapy techniques. In some cases, a standard course of radiation therapy may be delivered before seed implantation (4,000 cGy to 7,000 cGy in four to eight weeks) to achieve some tumor shrinkage prior to multilayer radioactive microsphere implantation. The combination of external-beam radiation therapy delivered either before or after seed implantation generally improves the homogeneity of the radiation within the target volume over that obtained using radioactive seeds alone.

External beam radiation therapy given before or after seed implantation is frequently used to irradiate occult microscopic metastases in regional nodes around a primary tumor and beyond the tumor target volume treated by the radioactive (multilayer radioactive microspheres) seed implant. For example, the treatment of a poorly-differentiated adenocarcinoma of the prostate could involve irradiation of the pelvic lymph nodes followed by radioactive seed (multilayer radioactive microspheres) implantation of the primary tumor mass.

This approach is effective because it is known that 5,000 cGy will control 90 percent of occult microscopic metastases in regional lymph nodes, but much higher doses of 16,000 cGy are necessary to achieve 90 percent control of a primary solid tumor mass in the prostate. Thus, sterilization of occult regional nodal metastases is accomplished by administration of external-beam radiation therapy, and sterilization of the primary tumor mass is accomplished by delivery of a high localized radiation dose using multilayer radioactive microspheres radioactive seed implantation of the tumor mass.

The course of external beam radiation therapy is then followed by implantation of multilayer radioactive microspheres radioactive seeds to safely deliver a high tumoricidal radiation dose to the target volume encompassing the tumor (8,000 cGy to 300,000 cGy). Alternatively, seed implantation alone can he used to treat a human tumor without the addition of external beam radiation therapy. Thus, tumoricidal radiation doses are achieved using either implantation of multilayer radioactive microspheres alone, or by administration of external beam radiation therapy before or after radioactive seed (multilayer radioactive microspheres) implantation. The critical point is that the primary goal of treatment using multilayer radioactive microspheres implantation with or without the addition of external beam radiation therapy is to achieve safe delivery of high tumoricidal radiation doses that are effective in controlling human tumors.

The primary types of endocurietherapy applications utilizing multilayer radioactive microspheres include: (1) permanent implantation of multilayer radioactive microspheres into human tumor tissues in locations such as the brain, pituitary, skull base, parotid, base of tongue, thyroid, tonsil, pharyngeal wall, neck nodes, mediastinum, spinal cord, lung, chest wall, axilla, brachial plexus, pleura, pancreas, liver, stomach, adrenals, abdominal wall, prostate, bladder, sacral tumors (chordoma), pelvic tumors (cervix, endometrium, prostate, bladder, rectum, anus, ovary, sarcomas), extremity tumors, et cetera, and implantation of multilayer radioactive microspheres surgical fabric in a resected tumor bed; (2) temporary interstitial needle or catheter implantation of multilayer radioactive microspheres (via removable tubes or sutures threaded through the needles, or via removable multilayered radioactive needles) into human tumor tissues located in accessible body sites such as the brain, floor of the mouth, anterior tongue, tonsil, face, scalp, skin surface, buccal mucosa, lip, extremities, neck nodes, chest wall, mediastinum, lung, bladder, cervix, endometrium, vagina, anus, rectum; (3) temporary intracavitary application of encapsulated multilayer radioactive microspheres or coated intracavitary cylinders or wires into accessible body cavities such as the bladder, rectum, vagina, cervix, endometrium, esophagus, trachea, bronchus, nose, nasopharynx et cetera; and (4) temporary application of multilayered radioactive plaques to accessible sites such as the hard palate, extremities, and globe of the eye.

In the second application, the dose delivered by the multilayer radioactive microspheres may be much less than tumoricidal. The goal of multilayer radioactive microspheres implantation in this case is not to directly kill the tumor by radiation emitted by the multilayer radioactive microspheres. Instead, the multilayer radioactive microspheres functioning as a radiation sensitizer is used to deliver continuous low dose rate radiation at a dose rate that serves to synchronize and block tumor cell populations in the most radio-sensitive phases of their cell cycles throughout a six to eight-week course of conventional external-beam radiation therapy.

This therapy accomplished by delivering radiation to the tumor tissues continuously 24-hours per day at a rate that permits cells to cycle yet causes the cell cycle to be blocked in the radio-sensitive part of the cell cycle ($G_2M$, late $G_2$, or $G_2/S$). The continuous radiation dose rate must be sufficiently high to prevent cell escape from the block and thus hold them at the block, but it must be sufficiently low to permit cells to proceed through their cell cycles without complete cycle inhibition. If the cells are blocked and held in the most radiosensitive phases of their cell cycles, then the daily administration of conventional fractionated external-beam radiotherapy (given daily, 5 days/week, 1 fraction/day, 150–225 cGy/fraction, 100–400 cGy/minute dose rate) will be much more efficient in killing tumor cells that might otherwise be in radioresistant phases (S-phase, $G_1$) at the time of administration of external-beam radiation (given in two-minutes every 24-hours).

Because of the great flexibility of the manufacturing process for production of multilayer radioactive microspheres of the present invention and the ability to produce multilayer radioactive microspheres containing over 220 different radionuclides, the half-life, energy, and activity of the multilayer radioactive microspheres can be precisely matched to the type and size of tumor being treated to deliver continuous low dose rate radiation at the proper rate to produce a sustained G-2 block.

Normally, the majority of cells in a tumor population are in radioresistant phases (quiescent somatic, resting phases) during the majority of the time, and only a small percentage of the population resides in radiosensitive phases. Thus, daily administration of fractionated external-beam radiation therapy results in irradiation of tumors composed mainly of cells that are radioresistant. The dose of conventional fractionated radiation required to control a radioresistant tumor cell population is relatively high (8,000 to 12,000 centi-Gray), and this dose is approximately 40 percent to 60 percent higher than what the surrounding normal tissues can tolerate.

For this reason, it is only possible to control approximately 30 percent of solid tumors (adenocarcinomas, squamous cell carcinomas, sarcomas, melanomas) treated by a conventional modern course of external-beam radiation therapy. This poor therapeutic ratio characteristic of conventional fractionated external-beam radiation therapy could be dramatically improved by modifying the radiosensitivity of the tumors under treatment. If tumors composed mainly of radiosensitive cells are irradiated in a conventional fashion, then the required tumor dose should be much lower. In fact, cell culture studies have indicated that cells blocked in G-2 phase can be killed by approximately half the dose of radiation normally required.

The amount of radiation that can be safely delivered by external means is limited by the surrounding normal tissues to a maximum of approximately 7,000 centi-Gray (cGy). This dose applied to a 5 centimenter diameter tumor composed largely of radioresistant cells results in approximately a 30 percent local control rate.

However, the same dose applied to a tumor composed largely of radiosensitive cells should result in a much higher local control rate. The tumor can be converted from one composed of radioresistant cells to one composed of radiosensitive cells by the permanent implantation of one or several multilayer radioactive microspheres which deliver continuous low dose rate irradiation at the proper rate to cause a sustained G-2 cell cycle block. Consequently, prior to administration of a conventional course of external-beam radiation therapy, implantation of one or several multilayer radioactive microspheres should dramatically increase the cure rate. This can be accomplished without an increased complication rate, because a relatively low total dose of radiation is delivered by the multilayer radioactive microspheres, and this dose is sharply localized due to the physical characteristics of the radionuclide.

If tumors treated by external-beam radiation therapy are first "radiosensitized" by implantation of one or several multilayer radioactive microspheres, then the seed implantation procedure may safely performed in a wide variety of human body sites without risk of complication caused by seed implantation. Because of the seed design, multilayer radioactive microspheres may be implanted into almost any body site using thin-caliber (21-gauge to 22-gauge) needles. Multilayer radioactive microspheres implantation performed using these thin gauge needles permits safe implantation without significant risk of bleeding or tissue trauma, and overlying loops of stomach or small intestine are usually not a contraindication.

In one system of therapy, a CT scanning system or other imaging system such as MRI (magnetic resonance imaging) is used to obtain images. A flat table is designed to attach over the standard curved CT scanner patient table. This table serves as a reference base for a stereotactic coordinate system. The table has built into the side rails X-ray markers that may be seen on the CT scout film, and allow determination of distance from a reference point on the Z-axis of the coordinate system.

The patient is immobilized on this table by means of straps or pins. A CT scan of the body is taken with images taken 0.20 to 2.0 centimeters apart. The area to be implanted with multilayer radioactive microspheres is determined by a physician, and a scan image (for example, image 5, Z=−90 millimeters) corresponding to the desired point of implantation is chosen. A semicircular arc composed of a material that is relatively transparent to X-ray images (titanium, or carbon filament) is then attached to the reference table at the level corresponding to the chosen scan image. A stereotactic instrument holder is attached to the arc or aiming bow.

The 21-gauge or 22-gauge implantation needle is inserted into the instrument holder. Stereotactic coordinates of the biopsy point are set on the aiming bow (arc) and instrument holder to direct the needle to the proper point, and adjustment are locked. A table slides the patient to the proper scan point, and using repeated CT scans through the chosen Z-coordinate slice, the needle is inserted into the target point within the patient under CT-guidance. The position of the needle tip is verified with a final CT scan when it is positioned in the center of the tumor to be implanted. The stylet is removed from the 21-G or 22-G implantation needle, and the radioactive multilayer radioactive microspheres is placed into the hollow needle and implanted into the tissue by replacing the needle stylet.

In another such system, the flat table is designed to attach over the standard curved CT scanner patient table. This table serves as a reference base for the robotic coordinate system. The table has built into the side rails "Z-shaped" X-ray markers that may be seen on the CT scout film, and allow determination of distance from a reference point on the Z-axis of the coordinate system. A commercially-available robot arm containing six joints of rotation and a relative accuracy of 0.05 millimeters is attached to a gantry linked to the table base coordinate system. The robotic arm is modified in that the arm is constructed only of materials known not to interfere with CT scanning X-rays (titanium, carbon filaments).

The patient is immobilized on this table by means of straps or pins. A CT scan of the body is taken with images taken 0.20 to 2.0 centimeters apart. The area to be implanted with multilayer radioactive microspheres is determined by a physician, and a scan image (for example, image 5, Z=−90 millimeters) corresponding to the desired point of implantation is chosen. Spatial target coordinates are determined by selecting the target point on the chosen CT-slice, and these are translated into base-reference system coordinates and robotic arm coordinates. The robotic arm aims a spring-loaded needle injector (which is capable of instantaneously injecting a 21-gauge or 22-gauge thin-diameter needle through human tissues to any desired distance at 1 to 5 millimeters increments to a maximum depth of 40 centimeters) at the target point.

The base table slides patient to proper scan point, and the needle injector is fired, placing the needle tip instantaneously at the desired target point within the body. The correct position of the needle tip is verified with a final CT scan when it is positioned in the center of the tumor to be implanted. The stylet is removed from the 21-G or 22-G implantation needle, and the radioactive multilayer radioactive microspheres is mechanically injected into the hollow needle and implanted into the tissue by mechanically pushing the stylet through the needle behind the seed.

EXAMPLES

The following hypothetical nonlimited examples illustrate the invention:

Example 1

A patient has a malignant adenocarcinoma of the head of the pancreas which is inoperable because of its proximity to the celiac plexus and porta hepatis and measures 3.5 in length×2.0 centimeters in diameter. The patient receives external-beam radiation therapy, but the maximum deliverable dose is limited to 6,000 centi-Gray because of potential toxicity to the surrounding normal tissues. This dose of 60 Gray delivered over 6 weeks, 200 centi-Gray/fraction, 5 days/week is known to be inadequate to result in lasting local control of this radioresistant tumor. His chances for local tumor control are now less than 30 percent.

The tumor is needle biopsied, and cell culture of the tumor is accomplished, and the cells are exposed to various dose rates of continuous irradiation. It is determined using flow cytometry techniques that a sustained G-2 block occurs if the cells receive continuous irradiation at a rate of 25 to 50 centi-Gray per hour. Computerized radiation dosimetry indicates that two I-125 seeds containing 25 mCi each implanted 1.7 centimeters apart produce a dose of 35 centi-Gray/hour to a tumor target volume measuring 3.5 cm×2.0 cm.

Two spherical multilayer radioactive microspheres 0.30 millimeters in diameter and containing 25 mCi of radioactive I-125 as described above are obtained. The patient is taken to the CT scanner and placed on the special flat base table connected to the robot gantry. Scans are taken, the target points are chosen, and coordinates are calculated and translated into robot arm coordinates. The robot arm fires the spring loaded 21-G needle to the correct location within the pancreatic tumor, and the correct position is verified with CT scan. The first I-125 multilayer radioactive microspheres is injected and permanently implanted. Another 25 mCi multilayer radioactive microspheres is implanted 1.7 centimeters from the first using the same technique.

Repeat tumor biopsy is performed 5 days later, and using flow cytometry, it is found that more than 90 percent of the tumor cells are blocked at G-2. Now the radiation dose of 6,000 cGy will be twice as effective because the tumor is composed mainly of radiosensitive tumor cells blocked in G-2. The 6,000 centi-Gray will be biologically equivalent to a dose of 12,000 centi-Gray, and chances for tumor control are increased to over 90 percent. The radiation dose delivered by the I-125 seeds adds to the tumoricidal effect, in addition to producing a sustained G-2 block that results in radio-sensitization to external-beam irradiation.

Example 2

A female patient with a malignant fibrous histiocytoma (MFH, soft tissue sarcoma) located in the presacral hollow and measuring 10 centimeters in diameter is determined to have an inoperable tumor due to bony invasion of the first sacral vertebral body. She is to receive a course of external-beam radiation therapy, but the maximum dose deliverable is limited to 7,000 centi-Gray in 7 weeks due to the poor tolerance of surrounding normal tissues including small bowel and colon. Her chances for local tumor control are less than 30 percent.

Cell culture of the tumor is successful, and cells are exposed to low dose rate irradiation. Flow cytometry studies indicate that radiation dose rates of 150 centi-Gray/hour are required to produce a sustained G-2 block, and thus render the sarcoma cells radiosensitive. Because of the high dose rates required to produce a G-2 block, the radioactive seed must have low energy to avoid irradiation adjacent structures.

Palladium-112 is chosen as the radionuclide with an energy of 18.5 KeV and half-life of 21.0 hours. Computerized radiation dosimetry indicates that ten seeds should optimally be implanted throughout the tumor volume. Ten spherical multilayer radioactive microspheres containing the required amount of Pd-112 and measuring less than 0.30 millimeters in diameter are manufactured according to the present disclosure.

The patient is taken to the CT scanner and the robotic arm is used to implant ten Pd-112 MRM's via a 21-G needle using CT guidance for verification. Repeat biopsy and cell culture with flow cytometry analysis indicates that more than 90 percent of cells are in G-2 block, and external-beam radiation therapy is initiated. The 7,000 cGy dose will be biologically equivalent to approximately 14,000 cry due to radiosensitization and G-2 block produced by the multilayer radioactive microspheres. Tumor control probability is increased to over 90 percent. Because of the short half-life of the radionuclide, the robotic multilayer radioactive microspheres implantation procedure is repeated twice a week during the patient's external-beam radiation therapy (seven week course).

Figure 6:
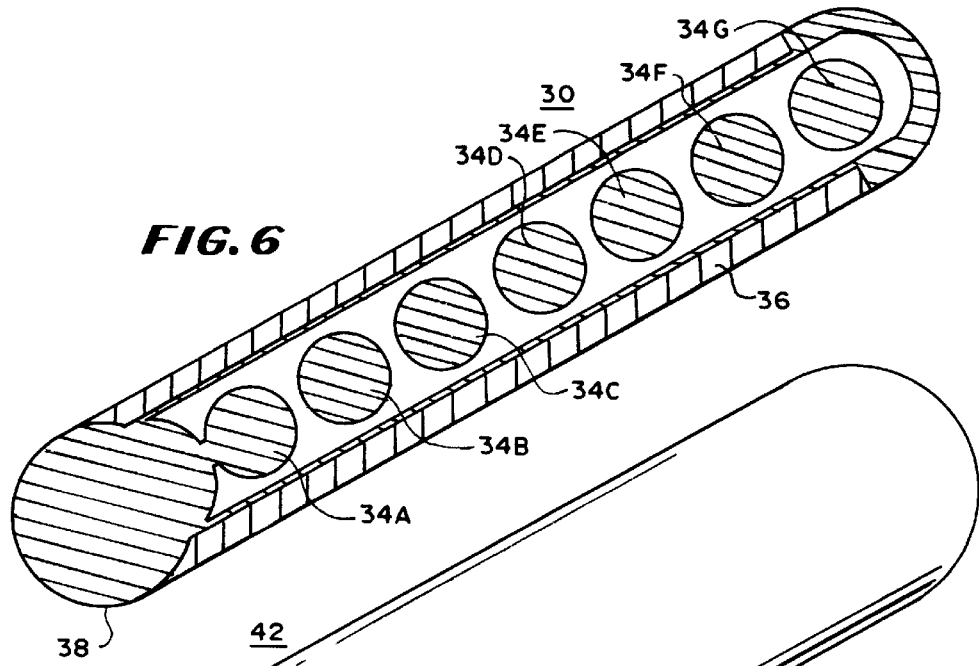
FIG. 6 is a longitudinal sectional view of an embodiment of intracavitary radiation-emitting implant.

In FIG. 6, there is shown an intracavitary radiation-emitting capsule 30 having a plurality of radiation emitting microspheres 34A–34G, a stainless steel tube 36 and an end weld 38. The end weld 38 seals the tube 36 which contains the microspheres 34A–34G. The microspheres 34A–34G are of the type described in connection with FIGS. 1–5 and are selected for the therapeutic treatment desired. While only 7 are shown in FIG. 6, a larger number are normally used and there may be as many as 40 contained in a cylindrical tube that is 2.0 centimeters long and 1 millimeter in diameter.

While microspheres are shown in FIG. 6 as inserts to the intracavitary implant 30, other sizes and shapes may be used such as cylindrical bars or other geometric shaped radiating units. However, standard sizes manufactured by the electron bonding processes in quantities are desirable because of their economy and the ability to manufacture them with different radiation characteristics for flexibility of treatment. Moreover different shapes and sizes of containers may be used and the walls, instead of being of only one material, may include different materials or added materials to provide different amounts of shielding. For example a square tube may contain square radiating elements and include shielding and elements of different radiating intensities and characteristics.

A wide variety of radionuclides with energies varying from very low to very high can he incorporated into composite intracavitary sources by sealing mulitple multilayer radioactive microspheres of one or several types into an appropriate container. Use of low energy intracavitary sources composed of low energy multilayer radioactive microspheres allows selective shielding of adjacent vital structures such as rectum and bladder using relatively thin high atomic weight foils placed over the intracavitary sources. Morever, a 1 millimeter diameter solid intracavitary source and a solid needle source can be manufactured by coating the rod or needle substrate with a radioactive coat, diffusion barrier coat and protective coat.

The intracavitary sources of the present invention eliminate the need for dilating openings because of their small size. For example: (1) the cervial canal or endocervical canal need not be dilated because the intracavitary multilayer radioactive microspheres or wires have an outside diameter not exceeding 1 millimeter and cervial applicator has an outside diameter of only 2 millimeters which can be easily inserted into the uterus without cervical dilitation; (2) the diameter of the intracavitary multilayer radioactive microsphere applicator is less than that of a uterine sound; (3) an intraoperative brain tumor applicator has a diameter of only two millimeters; and (4) the 1 millimeter source can be placed in a balloon catheter and easily slipped through the urethra for intracavitary bladder tumor irradiation.

The intracavitary multilayer radioactive microspheres can be easily shielded, making possible effective in vivo shielding of critical normal tissues at risk for radiation toxicity such as the bladder and rectum adjacent to the cervix. Thus, a radiation dose distribution can be designed that suits the individual patient's anatomy. The intracavitary multilayer radioactive sources of the present invention are suitable for treatment of cervix and uterine cancer, bladder cancers, esophageal cancers, biliary duct cancers, brain tumors, and nasopharyngeal cancers.

Figure 7:
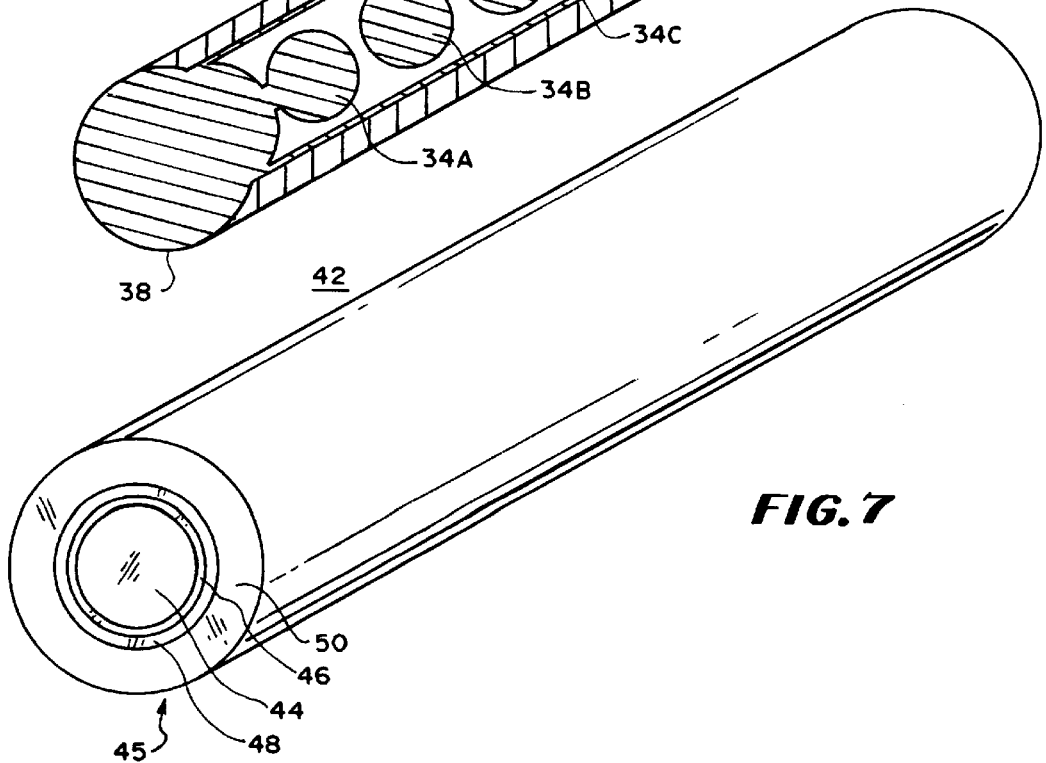
FIG. 7 is a perspective view of another embodiment of the invention formed as a wire or rod-like member.

In FIG. 7, there is shown another embodiment 42 of multilayer radiation emitting implant formed as a solid wire-like cylinder, without void spaces, and v having a plurality of layers similar to the microspheres described in connection with FIGS. 1–5.

In the preferred embodiment, the radiation emitting implant 42 is substantially 10 to 20 centimeters long and has an outer diameter of approximately 0.15 to 0.40 millimeters in diameter. The intensity of its emission may vary along its length and may vary in intensity and half-life. Moreover, radioactive shielding may be coated on part of it. It has a sufficiently high yield point to permit bending to that it can be shaped in coordination with its radiation characteristics along its length to permit planned dosage in three dimensions through a tumor.

The wire-like implant 42 includes a central cylinder 44 and a plurality of tubular layers 45 concentric with the central cylinder 44 and bonded to each other. The central cylinder serves as a substrate upon which other other layers, at least one of is a radiation emitter, are coated. The type of radiation emitting material is selected for appropriate intensity, to be beta particle or gamma ray emissive and for a predetermined half-life.

In the preferred embodiment, the central cylinder is 0.10 millimeter in diameter and made of tantalum and the layers are a holmium I-125 cylindrical tube 46, a hafnium nitride (HfN) cylindrical tube 48 and a titanium cylindrical tube 50, in the order named from the inside outwardly. The tube 46 is radiation emitting and may be applied at different thicknesses along the length of a wire-like implant by any of several methods to be described hereinunder. However, in the preferred embodiment, it is approximately 0.01 to 0.045 millimeters thick. The tube 48 is a diffusion barrier and substantially 0.005 to 0.05 millimeters in thickness and the tube 50 is a protective layer and is approximately 0.05 millimeter thick.

The multilayer radioactive wires of the present invention are used primarily for temporary removable implants. Instead of inserting bits of iridium wire into nylon tubing for afterloading (Pad/Irid Inc, Capitol Heights, Md.), a variety of different radionuclides incorporated into multilayered radioactive wires may be inserted into nylon or tissue compatible polyethylene tubing (American V. Mueller, American Hospital Supply Corporation) for temporary removable interstitial implants. These types of temporary removable implants are useful for implantation of tumors at accessible sites where the tubes penetrate the skin surface. Furthermore, a cut multilayer wire 1 millimeter in outer diameter may serve as an intracavitary source, or as a removable radioactive needle.

Temporary removable iridium-192 nylon ribbon implants have been used for treatment of head, neck, lung, vaginal, cervical, vulvar cancers, prostrate, breast, soft-tissue sarcomas and skin cancers. Radioactive wires placed in afterloading tubing may also be used for intracavitary treatment of esophageal cancer and biliary duct cancers (Klatskin's tumor) or bronchial lung cancers.

In FIGS. 8 and 9, there are shown a side sectional view and top sectional view of a ribbon-like radiation emissive implant 54 having a flexible ribbon-like connecting member 56 and a plurality of microsphere radiation emitters 58A–58C. The ribbon-like connecting member 56 acts as a rigid spacer between radiation emitters 58A–58C and allows multiple emitters to be implanted at once with a conventional thin gauge hollow needle by pushing the ribbon-like implant 54 out of the conventional tissue-embedded needle with a stylet while withdrawing the needle. The preferred rigid spacer -material is metal with a diamond coat.

In the preferred embodiment, the ribbon and the ribbon-emitters 58A–58C may be implanted with a very thin 21 or 22 -gauge needle. Although three radiation emitters are shown in FIG. 8, the ribbon-like implant 54 may be of any length and may contain any number of radiation emitters and any variety of different types of radiation emitters.

The ribbon-like implant 54 connects radioactive members internally by means of a thin metal ribbon or wire, rather than by an external suture, reducing the overall diameter. The ribbon-like connecting members are made rigid by locating lengths of tissue-compatible material over the connecting member between radiation emitters or by coating diamond-like carbon, or a low-atomic weight metal such as titanium or metal compound such as titanium nitride or zirocnium carbide over the connecting member between emitters using sputtering or plasma deposition. This rigid structure may be pushed into tissues from the proximal rather than distal end while simultaneously withdrawing the interstitial needle or may be implanted rapidly using automatic implantation devices described hereinafter.

In the preferred embodiment, the connecting member 56 is a 0.01 millimeter ribbon, substantially square or a 0.01 millimeter wire made of tungsten and the microspherical emitters contain, as shown in connection with emitter 58B an inner sphere 60 welded to the connector 56.

In this embodiment, the central sphere is 0.10 millimeters in diameter and made of tantalum and the layers are a holmium I-125 sphere 62, a hafnium nitride sphere 64 and a titanium sphere 66, in the order named from the inside outwardly. The sphere 62 is radiation emitting and methods to be described hereinunder. In the preferred embodiment, it is approximately 0.01 to 0.045 millimeters thick. The sphere 64 is a diffusion barrier and substantially 0.005 to 0.05 millimeters in a thickness and the sphere 66 is a protective layer and is approximately 0.05 millimeters thick.

The radiation emitters 58A–58C are optimized for individual tumor types so that permanent implants which deliver continuous low dose-rate irradiation over less than 130 days, may be used for slowly growing tumors such as prostate cancers, but because they may be less suitable for rapidly growing tumors such as glioblastomas, other shorter-lived emitters can be manufactured as needed by simply changing deposition parameters as discussed hereinafter. The ribbon-emitters are used mainly for permanent implants and the wire-emitters are used primarily for temporary-removable implants.

In FIGS. 10 and 11, there are shown a plan and a sectional view of a curved circular optical plaque 70 for applying radiation to the eye having a central radioactive layer 76, two outer steel or titanium supports 72A and 72B on either side of the radioactive layer 76, separated from the radioactive layer 76 by a corresponding two diffusion layers 78A and 78B. On the outside may be tissue compatible, anti-corrosive additional layers 80 and 82, if necessary. The layers form a section of a sphere with circumferentially spaced suture holes 74A–74H through it that provides a concave socket for applying a therapeutic dose of radiation inwardly to the eye.

To fit against the eye, the socket has a radius of curvature between 1.40 to 1.10 centimeters and the socket is formed in layers with no voids. The radioactive layer is low energy gamma emitter or beta emitter and may be a titanium-44 layer, an Sm-145, Sm-151, Tm-171 or I-125 layer having a thickness of about 0.01 to 0.045 millimeters. -Titanium-44 provides 68–78 kiloelectron volts (KeV) of radiation a half life of 47 years. The cord length from edge to edge (diameter of plan view) is between 8 millimeters to 22 millimeters.

In FIG. 12, there is shown a plan view of another embodiment of optical plaque 70A similar in construction to the plaque of 70 except that one portion at 71 is cut away so as to fit close to the lens to avoid damage thereto. Generally, this type of optical plaque will have a cord diameter of between 20 to 22 milimeters. Similarly, FIG. 13 shows an embodiment having an arc shaped cut away compartment at 71A to provide space around the optic nerve so as to avoid damage thereto. This embodiment may range in size between 8 millimeters to 22 millimeters in cord size.

Similar sized plaques are shown in the embodiment 70C in FIG. 14 with a larger portion cut away for convenient fitting and three other embodiments 70D, 70F, and 70F are shown in FIGS. 15, 16 and 17 respectfully, all of which have multiple parts. The embodiment 70D of FIG. 15 is generally an 8 millimeter embodiment and is formed in two section divided along a hemispheric line whereas the embodiments 16 and 17 are formed in three sections having a central section and two end sections, with the embodiment 7F including an optic nerve cut away in one of the sections.

Other variations are possible and are designed to fit closely adjacent to the cancerous tissue with minimum overlapping that might unnecessarily irradiate healthy tissue. All of these embodiments are intended to provide a high radiation level such as 10,000 centi-Gray encompassing the cancerous tissue near the capular wall and retina with rapid attenuation so that a short distance out the energy level falls below 3,000 centi-Gray which is tolerable to the retina and optic nerve. Generally that drop occurs at a 30 percent isodose line.

In FIG. 18, there is shown a surgical radiation-emitting fabric 90 having a border strip 92 of X-ray opaque fiber, a fabric base 94 of cellulose fibers, and a plurality of radiation emitters 96 spaced throughout the fabric base 94. The radiation emitters 96 have basic structure of the microspheres of FIGS. 1–5 extending from it.

One embodiment of the fabric of this invention self-adheres to the tissues over which it is placed. The fabric may be either tissue-absorbable or non-tissue absorbable and may contain multiple multilayered radioactive microspheres. This construction allows rapid surgical implantation of multiple seeds without need of interstitial needles or a seed gun. The radiation emitters 96 may be spaced at 1.0 to 2.5 centimeter intervals embeded into a tissue compatible fabric. This fabric may be sewn intraoperatively into the tumor bed, or in the case of brain tumors, the fabric is simply laid over the area to be treated. It self-adheres to the tissues over which it is placed.

Two types of fabric multilayer radioactive microspheres are produced—tissue-absorbable fabric and non-tissue absorbable fabric. The tissue-absorbable fabric is also hemostatic and is suitable for intraoperative permanent implantation of the surgical bed in the chest, abdomen, extremity, or brain. Since the multilayer radioactive microsphere surgical fabric is hemostatic, it sticks to the tissues upon which is applied and need not be sutured.

However, it may be sutured in for additional immobilization if desired. The fabric eventually dissolves after several months, and tissue fibrosis caused by local seed irradiation holds the seeds in place. The tissue half-life of the fabric is made to match the radioactive half-life of the radioactive seeds. The non-tissue absorbable multilayer radioactive microsphere surgical fabric may be used in accessible body cavities.

To be clinically useful, the multilayered radioactive microspheres should contain a minimum of 0.50 millicuries (mCi) of radioactive material, and the multilayered radioactive wires or filaments should contain a minimum of 0.50 millicuries (mCi) of radioactive material per centimeter of length.

The basic structures described in connection with FIGS. 1–18 can he used in many different therapy modalities depending on the characteristics of the material in the implants. For example, a "mixed" gamma/electron seed or microfilament can be prepared to produce a combination of high dose beta irradiation of a grossly visible tumor mass coupled with a lower dose "regional" gamma irradiation that spares the surrounding normal tissues yet provides enough radiation dose to sterilize microscopic tumor extensions into the normal tissues.

Thus, the mixed beta/gamma seed or microfilament accomplishes two goals simultaneously—it safely delivers an extremely well-localized tumoricidal dose to the grossly visible tumor mass and delivers a lower radiation dose to the surrounding normal tissues that is sufficient to sterilize microscopic tumor emboli or infiltrations. A seed such as this effectively eliminates the need for external-beam irradiation of the surrounding normal tissues and greatly simplifies definitive cancer treatment. It also reduces treatment cost and patient inconvenience since a course of external irradiation normally takes five to eight weeks to complete.

The beta seed and beta microfilament allows the beta particles to escape into the patient's tumor tissues by employing a container that is essentially "transparent" to beta particles. If beta-radiation is the only desired seed emission, then in the beta-particle-producing seed design, a low-Z atomic center must be used to prevent the production of bremsstrahlung X-rays by interaction of the electrons with a high-Z material. If a combination of beta particles and X-rays is desired, then a high-Z material would be used for the seed substrate center.

Above dose rates of 150 cGy/hour, there is no sparing beyond that produced by conventional external beam irradiation. At dose rates of 5–20 -cGy/hour, there is a marked sparing effect on normal tissues.

In clinical practice, permanently-implanted radioactive seeds with long half-lives have a biological advantage because they typically spare the adjacent normal tissue through a mechanism commonly known as "cellular repair of sublethal radiation damage" because they deliver cumulative radiation doses at very low dose rates over a long period of time. The disadvantage of radioactive seeds with long half-lives is that the cellular population of the tumor repopulates faster than cells are being killed by the low-dose-rate irradiation, resulting in clinical tumor recurrence and treatment failure.

On the other hand, seeds with short half-lives deliver their total radiation dose over a shorter period of time at much higher dose rates, resulting in somewhat less normal tissue sparing effect. They do produce a more rapid tumor cell killing effect, resulting in a more rapid clinical response.

These effects are combined into a single seed or radioactive microfilament design that contains radionuclides both with long and short half-lives. The short half-life component serves to get the tumor under control and reduce the tumor cell population without damaging the surrounding normal tissues. This radiation dose by itself does not result in permanent tumor cure but brings the tumor into remission. The second component of the seed is designed to deliver a large total radiation dose over an extended period of time without damaging the normal surrounding tissues, resulting in permanent tumor kill.

Multilayered radioactive implants that contain two or more different radionuclides with different half-lives, are produced by changing targets during the coating process. After one radionuclide or non-radioactive radionuclide precursor is coated, another can be coated over the first. The remainder of the seed or microfilament is manufactured as described above.

Neutron-producing microspheres and microfilaments consist of a substrate core that is coated by means of evaporation, sputtering, ion-beam sputtering, cathodic arc deposition, ion plating, or like means with either an alpha-particle-producing or gamma-producing material that is in turn coated with a light element target material that produces neutrons when irradiated by either high energy gamma rays or alpha particles produced by the inner coat. The energy produced by the alpha particle or gamma ray must be greater than the threshold energy of the target material used to produce the neutrons.

Since the alpha particles are very energetic, a wide variety of target elements may be used. With gamma-n sources, only two targets have a sufficiently low threshold energy to be useful— these are beryllium (1.67 MeV) and deuterium (2.23 MeV). The alpha-particle-producing or gamma-producing material can also be one that is initially non-radioactive but may he later activated by neutron activation in a neutron oven.

A microspherical substrate or microfilament is sputter-coated with an alpha-producing radioactive material from an alpha-producing radioactive sputter target. Alternatively, the coats may be produced by reactive coating from a radioactive alpha particle producing gas and a metal target. Examples of such materials would include radioactive americium-241 (t–1/2=458 years, alpha Energy (E)=5.5 MeVV, lead-210 (t–1/2=22 y, Alpha E=5.3 MeV), plutonium-238 (86 y, 5.5 MeV), actinium-225 (10.0d, 5.7 Me V), actinium-227 (22 y, 4.94 MeV), americium-241 (458 y, 5.48 MeV), curium-242 (163 d, 6.1 MeV), curium-244 (18 y, 5.8 MeV), neptunium-237 (2 million y, 4.8 MeV), thorium-228 (1.9 y, 5.4 MeV), uranium-232 (74 y, 5.3 MeV), plutonium-239 (24,400 y, 5.1 MeV), polonium-210 (138 days, k 5.3 MeV), radium-226 (1620 years, 4.5–7.7 MeV), uranium-238 (4.2 MeV, $4.5 \times 10^9$ years).

Following sputter-deposition of a sufficient amount of this material onto the microspherical substrate (1–50 microns thick) then a sufficient amount of the target material (1–50 microns thick) is sputter-coated directly onto the radioactive alpha particle producing coat. Suitable target materials for this purpose includes aluminum, beryllium, boron, lithium, magnesium, and sodium. The preferred alpha-producing coating of the present invention is polonium-210, and the preferred target coatings are boron and beryllium. These targets produce neutrons with energies of 5.0 MeV and 10.8 MeV, respectively, following alpha particle bombardment by the polonium-210 coat.

In another design, the nonradioactive elements may be sputter-coated, and the finished microspheres may be later activated in a neutron oven to produce the final alpha-n multilayered radioactive microspheres. For example, a batch of several thousand 400 micron titanium microspherical substrates are coated with 25 microns of bismuth. These are then coated with 25 microns of boron, followed by a 2 micron coat of chromium as a diffusion barrier and 50 microns of titanium as a protective coat.

The finished nonradioactive microspheres are then placed into a neutron flux, and the bismuth is converted to polonium-210 (saturation 1500 microcuries/gm in a flux of $10^{12}$n/cm$^2$/s). The polonium-210 then produces 5.3 MeV alpha particles that hit the adjacent boron target material, producing 5.0 MeV neutron irradiation over the lifetime of the polonium-210 (198 days). ,he neutrons produced in the boron coat exit through the titanium coat into the patient's tumor tissues.

In a similar fashion, several thousand 150 micron diameter microfilament substrates can be primed with 1 micron of chromium, then coated with 10 microns of bismuth, then coated with 10 microns of boron, 1 micron of chromium, and 30 microns of titanium to produce a neutron-emitting microfilament with an average lifetime of 198 days.

A microspherical substrate or microfilament is sputter-coated with a high-energy gamma-producing radioactive material from a gamma-producing radioactive sputter target. Alternatively, the coats may be produced by reactive coating from a radioactive high-energy gamma-producing gas and a metal target. Examples of such materials include radioactive antimony-124 (6% 2.09 MeV+98% 0.60 MeV, 60 d), radium-226+daughters, thorium-228+daughters, arsenic-76 (0.9% 2.08 MeV+44.6% 0.56 MeV, 26.5 hr), bismuth-207 (0.5% 2.47 MeV+98%0.56 MeV, 28 y), cobalt-56 (47% 2.5 MeV, 15% 3.25 MeV, 77 d), iodine-124 (2% 2.26 MeV, 51% 0.51 MeV, 4.0 d), lanthanum-240 (4% 2.54 MeV, 95% 1.60 MeV, 40.2 hr), rubidium-88 (2.5% 2.68 MeV, 23% 1.85 MeV), yttrium-88 (0.5% 2.76 MeV, 99.5% 1.84 MeV, 106 d).

Following sputter-deposition of a sufficient amount of this material onto the microspherical substrate (1–50 microns thick) then a sufficient amount of the target material (1–50 microns thick) is sputter-coated directly onto the radioactive high-energy gamma producing coat. Suitable target materials for this purpose are beryllium and deuterium. The preferred high-energy gamma producing coatings of the present invention include antimony-124 and arsenic-76. The preferred target coating is beryllium. This target produces neutrons with relatively low energies of 0.248 MeV.

In another design, the nonradioactive elements may be sputter-coated, and the finished microspheres may be later activated in a neutron oven to produce the final gamma-n multilayered radioactive microspheres. For example, a batch of several thousand 400 micron titanium microspherical substrates could be coated with 25 microns of antimony or arsenic. These are then coated with 25 microns of beryllium, followed by a 2 micron coat of chromium as a diffusion harrier and 50 microns of titanium as a protective coat. The finished nonradioactive microspheres are then placed into a neutron flux, and the antimony is converted to antimony-124 (Sb-124, saturation 140 mCi/gm in a flux of $10^{12}$n/cm$^2$/s) and arsenic is converted to As-76 (saturation 920 mCi/gm in neutron flux). The Sb-124 or As-76 then produces 2.1 MeV gamma rays that hit the adjacent beryllium target material, producing 0.248 MeV neutron irradiation over the lifetime of the Sb-124 (86 days) or As-76 (38 hrs). The neutrons produced in the boron coat exit through the titanium coat into the patient's tumor tissues.

In a similar fashion, several thousand 150 micron diameter microfilament substrates could be primed with 1 micron of chromium, then coated with 10 microns of antimony or arsenic, then coated with 10 microns of beryllium, 1 micron of chromium, and 30 microns of titanium to produce a neutron-emitting microfilament with an average lifetime of 86 days.

To control the energy level of X-rays produced by an implant, beta particle energy is modulated prior to the collision of the beta particle with a bremsstrahlung coat.

The beta particle energies are modulated by applying a low atomic weight coat (Z [ 40) over a beta particle producing coat. The thicker the coat, the lower the beta particle energy. Also, the energy degradation of the beta particle is controlled by the coat thickness and by the Z or E of the modulation material as well as the modulation material density. The starting energy of the beta particle should be less than 500 KeV to degrade the value using maximum modulating coats up to 100 microns thick.

To tailor low X-ray energies emitted from multilayered radioactive microspheres or microfilaments, a radioactive seed is prepared that consists of microspherical or microfilament substrate uniformly coated by an electron-producing (beta particle) radioactive coat with a kinetic energy modulation layer, that is in turn coated by a bremsstrahlung X-ray producing coat, that is in turn coated by a K-fluorescent or L-fluorescent low energy X-ray producing coat. The seed is finished with a protective tissue-compatible coat.

In another design, a radioactive microsphere or microfilament consists of a substrate uniformly coated by an electron-producing (beta particle) radioactive coat with a kinetic energy modulation layer, that is in turn coated by a bremsstrahlung X-ray producing coat, that is in turn coated by an Auger low energy electron producing coat, that is in turn coated by another bremsstrahlung X-ray producing coat. The seed is finished with a protective tissue-compatible coat.

In another design, a radioactive microsphere or microfilament consists of a substrate that is uniformly coated by an electron-producing (beta particle) radioactive coat with a kinetic energy modulation layer, that is in turn coated by a bremsstrahlung X-ray producing coat, that is in turn coated by an element that produces a mixture of Auger electrons and low energy K-fluorescence or L-fluorescence X-rays, that is in turn coated by another bremsstrahlung X-ray producing coat to produce additional low energy X-rays from the Auger electrons. The seed is finished with a protective tissue-compatible coat.

In another design, the microsphere or microfilament substrate itself serves as the target source of bremsstrahlung radiation after bombardment by a radioactive beta-producing coat. The beta particle kinetic energy modulation coat is therefore placed between the beta-particle coat and the non-radioactive central substrate material. After beta-particle bombardment, the central core emits bremsstrahlung X-rays that travel back through the modulation and beta radioactive coats into the K-fluorescent/L-fluorescent coat and Auger target coats. The K-fluorescent coat is stimulated by the bremsstrahlung radiation to emit additional lower energy X-rays. Likewise, the Auger target coat is stimulated by the bremsstrahlung radiation to emit lower energy beta particles. Thus, the Auger coat needs to be flanked on the inside and outside by two additional bremsstrahlung target coats. Finally, a tissue-compatible protective coat such as titanium and an optional finishing coat such as diamond-like carbon is applied to finish the manufacture of the radioactive fluorescent microspheres or microfilaments.

More specifically, this implant includes nine coats. The first coat is a central microspherical or microfilament core that is composed of an efficient bremsstrahlung-producing high-Z material such as hafnium, tantalum, tungsten, rhenium, osmium, or uranium. This high-Z core also serves as an X-ray marker that permits visualization of the seed implanted into human tissues. Bremsstrahlung X-ray production is proportional to $Z^2$. The average energy of the photons produced will be about ⅓ of the modulated beta energy.

The second coat is a beta-particle kinetic energy (KE) modulation coat that serves to slow the beta particles before they collide with the bremsstrahlung target material in the central core. The preferred kinetic energy modulation coats are low-Z materials including carbon graphite, diamond-like carbon, diamond, aluminum, titanium, vanadium, and chromium.

The third coat is the radioactive beta-particle producing coat. This produces beta particles that have kinetic energies of between 5 KeV and 500 KeV. It is desirable to have a radioactive coat that produces only beta particles without significant gamma-ray production. In this manner, an excess amount of beta-producing radioactive material can be placed in the coat to overcome the inherent inefficiency of the bremsstrahlung X-ray production process. The preferred radioactive beta-particle-producing radionuclides for this coat include Pd-112, Tm-165, N i-66, U-237, Er-169, P-33, W-185, S-35, Os-194, H-3 (tritium), Ru-106, Pb-210, and Sr-90. The fourth coat is a diffusion barrier such as chromium nitride or titanium nitride is coated over the radioactive coat to prevent atomic leakage into the outer seed coats.

The fifth coat is a K-fluorescent or L-fluorescent target material coated over the diffusion barrier coat. This coat would produce characteristic low energy X-rays (5–60 KeV) when bombarded by white bremsstrahlung X-rays produced by the stimulated central core high-Z material. Preferred materials for this fluorescent X-ray coat consist of zirconium, molybdenum, palladium, silver, cadmium, indium, tin, antimony, and tellurium.

The sixth coat is a secondary bremsstrahlung coat. This coat is again composed of a thin layer of a high-Z material such as tungsten. It is placed adjacent to the seventh coat which is the Auger electron producing coat. Lower energy X-rays are produced by bremsstrahlung from the low energy Auger electrons stimulated by the bremsstrahlung radiation originating from the central core material.

The seventh coat is the Auger electron target coat. This coat serves to produce Auger electrons due to stimulation from bremsstrahlung X-rays produced in the central core material. The low energy Auger electrons are utilized to produce even lower bremsstrahlung X-rays as they strike the adjacent high-Z target materials. Preferred Auger electron-producing materials would have Z-values below 30. Preferred target materials for this purpose include titanium, vanadium, chromium, nickel, copper, zinc, and aluminum.

The eighth coat is a secondary bremsstrahlung coat. This coat is composed of a thin layer of a high-Z material such as tungsten. It is also placed adjacent to the seventh coat, the Auger electron producing coat.

The ninth coat is an optional marker coat. This thin coat is composed of a paramagnetic material such as samarium that is easily visualized on conventional magnetic resonance imaging scanners.

The tenth coat is a protective coat. This is a relatively thick coat designed to mechanically protect the inner coats. Preferred materials for this coat include relatively low-Z materials that have a high corrosion-resistance and good human tissue compatibility such as titanium, vanadium, and chromium.

The eleventh coat is an optional outer coat. This coat is designed to impart additional corrosion resistance, improve friction reduction, impart additional hardness and smoothness, and or to add colors. Preferred materials include diamond-like carbon or diamond coats, titanium nitride, hafnium nitride, tungsten nitride, or tantalum nitride.

The preferred radioactive coats used in the production of fluorescent X-ray producing radioactive seeds and wires of the present invention are shown in tables 123 and 124.

Since a relatively high level of radioactivity may be needed in the beta-particle coat to produce sufficient bremsstrahlung radiation, beta-producing radionuclides are preferred that do not also produce gamma rays. Therefore, the preferred radionuclides produce beta particles with essentially no gamma component. Additionally, the electron energy must be below approximately 500 KeV,. These energies may be modulated downward using a low-Z coating.

The preferred beta particle energy modulation coatings consist of materials that will slow but not shield the beta particles. These are listed in table 125. The R (in microns) or average distance

TABLE 62

| ISOTOPE | HALF-LIFE | ENERGY | RADIOACTIVE REACTIVE SPUTTER-GAS |
|---|---|---|---|
| Sb-119 | 36.1 hrs | 23.9 KeV | Sb-119H$_3$ Sb-119Cl$_5$ |
| Sb-125 | 2.8 yrs | 427–636 KeV | Sb-125H$_3$ Sb-125Cl$_5$ |

TABLE 63

| ISOTOPE | HALF-LIFE | ENERGY | RADIOACTIVE REACTIVE SPUTTER-GAS |
|---|---|---|---|
| As-73 | 80.3 days | 53.4 KeV | As-73CL$_3$ As-73F$_5$ As-73H$_3$ |
| As-74 | 17.8 days | 595 KeV | As-74Cl$_3$ As-74F$_5$ As-73H$_3$ |
| As-77 | 38.8 hours | 239 KeV | As-77Cl$_3$ As-77F$_5$ As-77H$_3$ |

TABLE 64

| ISOTOPE | HALF-LIFE | ENERGY | RADIOACTIVE REACTIVE SPUTTER-GAS |
|---|---|---|---|
| Bi-210 | 5.0 days | 1.16 MeV Beta | Bi-210H$_3$ |

TABLE 65

| ISOTOPE | HALF-LIFE | ENERGY | RADIOACTIVE REACTIVE SPUTTER-GAS |
|---|---|---|---|
| Br-77 | 57.0 hours | 87.0–818 KeV | (Br-77)$_2$ Br-77F$_{1.5}$ |

TABLE 66

| ISOTOPE | HALF-LIFE | ENERGY | RADIOACTIVE REACTIVE SPUTTER-GAS |
|---|---|---|---|
| Ca-45 | 163.8 days | 257 KeV Beta Particle | Ca-45S Ca-45F |

TABLE 67

| ISOTOPE | HALF-LIFE | ENERGY | RADIOACTIVE REACTIVE SPUTTER-GAS |
|---|---|---|---|
| Cd-109 | 450 days | 88 KeV | Cd-1090 |
| Cd-113m | 13.7 years | 590 KeV Beta Particle | Cd-113mO |
| Cd-115m | 43 days | 935 KeV (0.9%) 1.62 MeV Beta Particle | Cd-115mO |

TABLE 68

| ISOTOPE | HALF-LIFE | ENERGY | RADIOACTIVE REACTIVE SPUTTER-GAS |
|---|---|---|---|
| Ce-141 | 33 days | 145 KeV | Ce-141F$_3$ Ce-141Te |

TABLE 69

| ISOTOPE | HALF-LIFE | ENERGY | RADIOACTIVE REACTIVE SPUTTER-GAS |
|---|---|---|---|
| Cs-129 | 32.3 hours | 371-412 KeV | Cs-129Br$_2$Cl |
| Cs-131 | 9.7 days | 4.0–30.0 KeV | Cs-131Br$_2$Cl |
| Cs-135 | 1000 years | 210 KeV Beta Particle | Cs-135Br$_2$ |
| Cs-137 | 30.2 years | 662 KeV | Cs-137Br$_2$Cl |

TABLE 70

| ISOTOPE | HALF-LIFE | ENERGY | RADIOACTIVE REACTIVE SPUTTER-GAS |
|---|---|---|---|
| Cr-48 | 21.6 hours | 116–305 KeV | Cr-48O$_2$Cl$_2$ |
| Cr-51 | 27.0 days | 320 KeV | Cr-51O$_2$Cl$_2$ |

TABLE 71

| ISOTOPE | HALF-LIFE | ENERGY | RADIOACTIVE REACTIVE SPUTTER-GAS |
|---|---|---|---|
| Dy-166 | 81.6 hours | 82.5 KeV (400 KeV Beta) | Dy-166F$_3$ Dy-166Cl$_3$ |
| Dy-159 | 144 days | 326 KeV | Dy-159F$_3$ Dy-159Cl$_3$ |

TABLE 72

| ISOTOPE | HALF-LIFE | ENERGY | RADIOACTIVE REACTIVE SPUTTER-GAS |
|---|---|---|---|
| Er-169 | 9.4 days | 8.42 KeV | Er-169F$_3$ |
| | | 340 KeV Beta | Er-169Cl$_3$ |
| | | | Er-169Br$_3$ |

TABLE 73

| ISOTOPE | HALF-LIFE | ENERGY | RADIOACTIVE REACTIVE SPUTTER-GAS |
|---|---|---|---|
| Eu-155 | 4.7 years | 105 KeV | Fu-155Cl$_3$ |
| | | | EU-155F$_3$ |
| | | | Eu-155S |

TABLE 74

| ISOTOPE | HALF-LIFE | ENERGY | RADIOACTIVE REACTIVE SPUTTER-GAS |
|---|---|---|---|
| Ga-67 | 78.3 hours | 93–394 KeV | (Ga-67)$_2$H$_6$ |
| | | | Ga-67Cl$_3$ |

TABLE 75

| ISOTOPE | HALF-LIFE | ENERGY | RADIOACTIVE REACTIVE SPUTTER-GAS |
|---|---|---|---|
| Gs-159 | 18.6 hours | 364 KeV | Gd-159Cl$_3$ |
| | | | Gd-159F$_3$ |

TABLE 76

| ISOTOPE | HALF-LIFE | ENERGY | RADIOACTIVE REACTIVE SPUTTER-GAS |
|---|---|---|---|
| Ge-68 | 280 days | 92 KeV | Ge-68F$_3$Cl |
| | | | Ge-68Cl$_2$F$_2$ |
| | | | Ge-68H$_4$ |
| Ge-71 | 11 days | 92 KeV | Ge-71F$_3$Cl |
| | | | Ge-71Cl$_2$F$_2$ |
| | | | Ge-71H$_4$ |

TABLE 77

| ISOTOPE | HALF-LIFE | ENERGY | RADIOACTIVE REACTIVE SPUTTER-GAS |
|---|---|---|---|
| Au-193 | 17.6 hours | 112–439 KeV | Au-193S |
| Au-198 | 2.7 days | 412 KeV | Au-198S |
| Au-199 | 3.1 days | 158–208 KeV | Au-199S |

TABLE 78

| ISOTOPE | HALF-LIFE | ENERGY | RADIOACTIVE REACTIVE SPUTTER-GAS |
|---|---|---|---|
| Hf-181 | 42 days | 133–482 KeV | Hf-181Cl$_2$ |
| | | | Hf-181F$_4$ |

TABLE 79

| ISOTOPE | HALF-LIFE | ENERGY | RADIOACTIVE REACTIVE SPUTTER-GAS |
|---|---|---|---|
| Ho-166 | 1.1 days | 80.5 KeV | Ho-166Cl$_3$ |
| | | 1.8 MeV | Ho-166F$_3$ |
| | | Beta Part. | |

TABLE 80

| ISOTOPE | HALF-LIFE | ENERGY | RADIOACTIVE REACTIVE SPUTTER-GAS |
|---|---|---|---|
| In-111 | 2.8 days | 170–245 KeV | In-111F$_3$ |
| In-114m | 50 days | 191–724 KeV | In-114mF$_3$ |

TABLE 81

| ISOTOPE | HALF-LIFE | ENERGY | RADIOACTIVE REACTIVE SPUTTER-GAS |
|---|---|---|---|
| I-125 | 59.9 days | 35.5 KeV | (I-125)$_2$ |
| | | | I-125F$_5$ |
| | | | HI-125 |
| | | | AgI-125 |
| | | | Al(I-125)$_3$ |
| I-129 | 1000 years | 189 KeV Beta Part. (39.6 KeV gamma) | (I-129)$_2$ |
| | | | I-129F$_5$ |
| | | | I-129 |
| | | | AgI-129 |
| | | | Al(I-129)$_3$ |
| I-131 | 8.0 days | 364 KeV | (I-131)$_2$ |
| | | | I-131F$_5$ |
| | | | I-131 |
| | | | AgI-131 |
| | | | Al(I-125)$_3$ |

TABLE 82

| ISOTOPE | HALF-LIFE | ENERGY | RADIOACTIVE REACTIVE SPUTTER-GAS |
|---|---|---|---|
| Ir-189 | 13.2 days | 245 KeV | Ir-189F$_6$ |
| | | | Ir-189O$_3$ |
| Ir-192 | 73.8 days | 205–604 KeV | Ir-192F$_6$ |
| | | | Ir-192O$_3$ |

TABLE 83

| ISOTOPE | HALF-LIFE | ENERGY | RADIOACTIVE REACTIVE SPUTTER-GAS |
|---|---|---|---|
| Fe-52 | 8.2 hours | 168–377 KeV | $Fe\text{-}52(CO)_5$ |
| | | | $Fe\text{-}52F_3$ |

TABLE 84

| ISOTOPE | HALF-LIFE | ENERGY | RADIOACTIVE REACTIVE SPUTTER-GAS |
|---|---|---|---|
| La-140 | 40 hours | 408–815 KeV | $La\text{-}140Cl_3$ |

TABLE 85

| ISOTOPE | HALF-LIFE | ENERGY | RADIOACTIVE REACTIVE SPUTTER-GAS |
|---|---|---|---|
| PB-210 | 21 years | 46.5 KeV gamma 15–61 KeV Beta Particle | $Pb\text{-}210F_4$ $Pb\text{-}210Te$ |

TABLE 86

| ISOTOPE | HALF-LIFE | ENERGY | RADIOACTIVE REACTIVE SPUTTER-GAS |
|---|---|---|---|
| Lu-173 | 1.4 years | 78–271 KeV | $Lu\text{-}173F_3$ |
| Lu-174 | 3.3 years | 76.6 KeV | $Lu\text{-}174F_3$ |
| Lu-176m | 3.6 hours | 88.3 KeV | $Lu\text{-}176mF_3$ |
| Lu-177 | 6.7 days | 113–332 KeV | $Lu\text{-}177F_3$ |

TABLE 87

| ISOTOPE | HALF-LIFE | ENERGY | RADIOACTIVE REACTIVE SPUTTER-GAS |
|---|---|---|---|
| Hg-197 | 65 hours | 69–77 Kev | Hg-197 $Hg\text{-}197Br_2$ Hg-197F |
| Hg-195m | 40.0 hours | 262 KeV | Hg-195m $Hg\text{-}195mBr_2$ Hg-195F |
| Hg-197m | 23.8 hours | 134 KeV | Hg-197m $Hg\text{-}197mBr_2$ Hg-197F |

TABLE 88

| ISOTOPE | HALF-LIFE | ENERGY | RADIOACTIVE REACTIVE SPUTTER-GAS |
|---|---|---|---|
| Mo-99 | 65.9 hours | 144–739 KeV | $Mo\text{-}99F_6$ $Mo\text{-}99OF_4$ $Mo\text{-}99Cl_5$ |
| Mo-93 | 3500 years | 30.4 KeV | $Mo\text{-}93F_6$ $Mo\text{-}93OF_4$ |

TABLE 89

| ISOTOPE | HALF-LIFE | ENERGY | RADIOACTIVE REACTIVE SPUTTER-GAS |
|---|---|---|---|
| Nd-147 | 10.9 days | 91–531 KeV | $Nd\text{-}147I_3$ |

TABLE 90

| ISOTOPE | HALF-LIFE | ENERGY | RADIOACTIVE REACTIVE SPUTTER-GAS |
|---|---|---|---|
| Nb-92M | 10.1 days | 934 KeV | $Nb\text{-}92Mf_5$ $Nb\text{-}92mCl_5$ |
| Nb-93m | 13.6 years | 30.4 KeV | $Nb\text{-}93mF_5$ $Nb\text{-}93mCl_5$ |

TABLE 91

| ISOTOPE | HALF-LIFE | ENERGY | RADIOACTIVE REACTIVE SPUTTER-GAS |
|---|---|---|---|
| Nd-147 | 11 days | 91 KeV | $Nd\text{-}147F_3$ $Nd\text{-}147Cl_3$ |

TABLE 92

| ISOTOPE | HALF-LIFE | ENERGY | RADIOACTIVE REACTIVE SPUTTER-GAS |
|---|---|---|---|
| Ni-63 | 92.0 years | 67 KeV Beta Particle | $Ni\text{-}63(CO)_4$ |
| Ni-66 | 54.6 hours | 200 KeV Beta Particle | $Ni\text{-}66(CO)_4$ |

TABLE 93

| ISOTOPE | HALF-LIFE | ENERGY | RADIOACTIVE REACTIVE SPUTTER-GAS |
|---|---|---|---|
| Os-182 | 21.5 hours | 131–510 KeV | $Os\text{-}182F_6$ $Os\text{-}182O_4$ |
| Os-191 | 15.4 days | 129.4 KeV | $Os\text{-}191F_6$ $Os\text{-}191O_4$ |
| Os-194 | 6.0 years | 42.9 KeV (10% gamma) 54.0 KeV Beta Particle | $Os\text{-}194F_6$ $Os\text{-}194O_4$ |

TABLE 94

| ISOTOPE | HALF-LIFE | ENERGY | RADIOACTIVE REACTIVE SPUTTER-GAS |
|---|---|---|---|
| P-32 | 14.3 days | 1.71 MeV Beta Particle | $P\text{-}32H_3$ $P\text{-}32F_5$ $P\text{-}32Cl_2F_3$ |
| P-33 | 25.3 days | 249 KeV | $P\text{-}33H_3$ $P\text{-}33F_5$ $P\text{-}33Cl_2F_3$ |

TABLE 95

| ISOTOPE | HALF-LIFE | ENERGY | RADIOACTIVE REACTIVE SPUTTER-GAS |
|---|---|---|---|
| Pr-143 | 13.6 days | 935 KeV Beta Particle | Pr-143Cl$_3$ Pr-143F$_3$ |

TABLE 96

| ISOTOPE | HALF-LIFE | ENERGY | RADIOACTIVE REACTIVE SPUTTER-GAS |
|---|---|---|---|
| Pu-237 | 45.1 days | 59.5 KeV gamma | Pu-237F$_6$ |
| Pu-246- | 10.9 days | 44–224 KeV gamma 150–330 KeV Beta Particle | Pu-246F$_6$ |

TABLE 97

| ISOTOPE | HALF-LIFE | ENERGY | RADIOACTIVE REACTIVE SPUTTER-GAS |
|---|---|---|---|
| K-42 | 12.4 hours | 3.52 MeV Beta Particle | K-42H |

TABLE 98

| ISOTOPE | HALF-LIFE | ENERGY | RADIOACTIVE REACTIVE SPUTTER-GAS |
|---|---|---|---|
| Re-181 | 20.0 hours | 177–365 KeV | Re-181F$_6$ Re-181O$F_4$ Re-181O$_3$Br |
| Re-183 | 70.0 days | 163 KeV | Re-183F$_6$ Re-183OF$_4$ Re-183O$_3$Br |
| Re-186 | 3.7 days | 1.07 MeV Beta Particle | Re-186F$_6$ Re-186OF$_4$ Re-186O$_3$Br |
| Re-187 | 1000 years | 8 KeV Beta Particle | Re-187F$_6$ Re-187OF$_4$ Re-187O$_3$Br |

TABLE 99

| ISOTOPE | HALF-LIFE | ENERGY | RADIOACTIVE REACTIVE SPUTTER-GAS |
|---|---|---|---|
| Rh-105 | 35.4 hours | 306–319 KeV | Rh-105Cl$_3$ Rh-105O$_2$ |

TABLE 100

| ISOTOPE | HALF-LIFE | ENERGY | RADIOACTIVE REACTIVE SPUTTER-GAS |
|---|---|---|---|
| Rb-87 | 1000 years | 274 KeV Beta Particle | Rb-187Cl Rb-187F$_2$ |

TABLE 101

| ISOTOPE | HALF-LIFE | ENERGY | RADIOACTIVE REACTIVE SPUTTER-GAS |
|---|---|---|---|
| Ru-97 | 2.9 days | 216–461 KeV | Ru-97F$_5$ Ru-97Cl$_3$ |
| Ru-106 | 367 days | 39.2 KeV Beta Particle | Ru-106$_5$ Ru-106O$_3$ |

TABLE 102

| ISOTOPE | HALF-LIFE | ENERGY | RADIOACTIVE REACTIVE SPUTTER-GAS |
|---|---|---|---|
| Sm-151 | 93 years | 55–76 KeV Beta Particle | Sm-151 |
| Sm-153 | 46.7 hours | 103 KeV | Sm-153 |
| Sm-145 | 340 days | 61.3 KeV | Sm-145 |

TABLE 103

| ISOTOPE | HALF-LIFE | ENERGY | RADIOACTIVE REACTIVE SPUTTER-GAS |
|---|---|---|---|
| Sc-47 | 3.4 days | 159 KeV | Sc-47F$_3$ |

TABLE 104

| ISOTOPE | HALF-LIFE | ENERGY | RADIOACTIVE REACTIVE SPUTTER-GAS |
|---|---|---|---|
| Se-72 | 8.4 days | 46.0 KeV | Se-72H$_2$ Se-72F$_6$ Se-72O$_3$ |
| Se-79 | 1000 years | 154 KeV Beta Particle | Se-73H$_2$ Se-73F$_6$ Se-73O$_3$ |

TABLE 105

| ISOTOPE | HALF-LIFE | ENERGY | RADIOACTIVE REACTIVE SPUTTER-GAS |
|---|---|---|---|
| Ag-111 | 7.5 days | 250–340 KeV 1.0 MeV Beta Particle | Ag-111N$_3$ |

TABLE 106

| ISOTOPE | HALF-LIFE | ENERGY | RADIOACTIVE REACTIVE SPUTTER-GAS |
|---|---|---|---|
| Si-32 | 650 years | 210 KeV Beta Particle | Si-32H$_4$ Si-32H Si-32F$_4$ Si-32O |

TABLE 107

| ISOTOPE | HALF-LIFE | ENERGY | RADIOACTIVE REACTIVE SPUTTER-GAS |
|---|---|---|---|
| Sr-83 | 32.4 hours | 763 KeV | Sr-83O$_2$ Sr-83s |
| Sr-85 | 64.8 days | 514 KeV | Sr-85O$_2$ Sr-85s |
| Sr-89 | 50.5 days | 1.49 MeV Beta | Sr-89O$_2$ Sr-89s |
| Sr-90 | 29.0 years | 546 KeV Beta | Sr-90O$_2$ Sr-90s |

TABLE 108

| ISOTOPE | HALF-LIFE | ENERGY | RADIOACTIVE REACTIVE SPUTTER-GAS |
|---|---|---|---|
| S-35 | 87.2 days | 167 KeV Beta Particle | S-32Cl$_4$ S35F$_6$ S-35O$_2$ H$_2$S-35 |

TABLE 109

| ISOTOPE | HALF-LIFE | ENERGY | RADIOACTIVE REACTIVE SPUTTER-GAS |
|---|---|---|---|
| Ta-177 | 2.4 days | 113 KeV | Ta-177F$_8$ Ta-177I$_5$ Ta-177S |
| Ta-180m | 8.2 hours | 93.3–103 KeV | Ta-180mF$_8$ Ta-180mI$_5$ Ta-180S |
| Ta-182 | 115 days | 100–1221 KeV | Ta-182F$_8$ Ta-182I$_5$ Ta-182S |

TABLE 110

| ISOTOPE | HALF-LIFE | ENERGY | RADIOACTIVE REACTIVE SPUTTER-GAS |
|---|---|---|---|
| Tc-99m | 6 hours | 140 KeV | Tc-99m (Tc-99m)$_2$O$_7$ |
| Tc-99 | 1000 years | 292 KeV Beta Particle | Tc-99 (Tc-99)$_2$O$_7$ |

TABLE 111

| ISOTOPE | HALF-LIFE | ENERGY | RADIOACTIVE REACTIVE SPUTTER-GAS |
|---|---|---|---|
| Te-123m | 117 days | 88–159 KeV | Te-123mH$_2$ Te-123mF$_6$ Te-123mF$_4$ |
| Te-125m | 58.0 days | 35.5 KeV | Te-125mH$_2$ Te-125mF$_6$ Te-125mF$_4$ |
| Te-127m | 109 days | 88.3 KeV | Te-127mH$_2$ Te-127mF$_6$ Te-127mF$_4$ |
| Te-132 | 78.2 hours | 49.7–228 KeV | Te-132H$_2$ Te-132F$_6$ Te-132F$_4$ |

TABLE 112

| ISOTOPE | HALF-LIFE | ENERGY | RADIOACTIVE REACTIVE SPUTTER-GAS |
|---|---|---|---|
| Tb-151 | 17.6 hours | 108–731 KeV | Tb-151Se Tb-151Te Tb-151Cl$_3$ |
| Tb-155 | 5.3 days | 86.5–105.3 KeV | Tb-155Se Tb-155Te Tb-155Cl$_3$ |
| Tb-160 | 73 days | 298 KeV | Tb-160Se Tb-160Te Tb-160Cl$_3$ |
| Tb-161 | 6.9 days | 25.6–74.6 KeV | Tb-161Se Tb-161Te Tb-161Cl$_3$ |

TABLE 113

| ISOTOPE | HALF-LIFE | ENERGY | RADIOACTIVE REACTIVE SPUTTER-GAS |
|---|---|---|---|
| Th-231 | 25.5 | 84.2 KeV gamma 299 KeV Beta Particle | Th-231 (C$_5$H$_7$O$_2$)$_4$ Th-231F$_4$ Th-231I$_4$ Th-231O$_2$ |
| Th-234 | 24.1 days | 63.3–92.7 KeV | Th-234 (C$_5$H$_7$O$_2$)4 Th-234F$_4$ Th-234I$_4$ Th-234O$_2$ |

TABLE 114

| ISOTOPE | HALF-LIFE | ENERGY | RADIOACTIVE REACTIVE SPUTTER-GAS |
|---|---|---|---|
| Sn-117 | 14 days | 159 KeV | Sn-117H$_4$ Sn-117BrCl$_3$ Sn-117Cl$_4$ Sn-117ClBr$_3$ Sn-117Te |
| Sn-119m | 245 days | 24.0–65.0 KeV | Sn-119mH$_4$ Sn-119mBrCl$_3$ Sn-119mCl$_4$ Sn-119mClBr$_3$ Sn-119mTe |
| Sn-121 | 76 years | 37 KeV | Sn-121H$_4$ Sn-121BrCl$_3$ |

TABLE 114-continued

| ISOTOPE | HALF-LIFE | ENERGY | RADIOACTIVE REACTIVE SPUTTER-GAS |
|---|---|---|---|
| Sn-123 | 129.2 days | 1.43 MeV Beta Particle | Sn-121Cl$_4$ Sn-121ClBr$_3$ Sn-121Te Sn-123H$_4$ Sn-123BrCl$_3$ Sn-123Cl$_4$ Sn-123ClBr$_3$ Sn-123Te |

TABLE 115

| ISOTOPE | HALF-LIFE | ENERGY | RADIOACTIVE REACTIVE SPUTTER-GAS |
|---|---|---|---|
| Ti-44 | 48 years | 68–78 KeV | Ti-44Cl$_4$ Ti-44Br$_4$ Ti-44F$_4$ |
| Ti-45 | 3.1 | 1.04 MeV Beta Particle | Ti-45Cl$_4$ Ti-45Br$_4$ Ti-45F$_4$ |

TABLE 116

| ISOTOPE | HALF-LIFE | ENERGY | RADIOACTIVE REACTIVE SPUTTER-GAS |
|---|---|---|---|
| Tl-201 | 3.05 days | Hg K-X-ray 136–167 KeV | Tl-201Cl Tl-201Cl$_2$ Tl-201F$_2$ (Tl-201)$_2$O Tl-201I |
| Tl-202 | 12.2 days | 439 KeV | Tl-202Cl Tl-202Cl$_2$ Tl-202F$_2$ Tl-202F$_2$ (Tl-202)$_2$O Tl-202I |
| Tl-204 | 3.8 years | 763 KeV Beta Particle | Tl-204Cl Tl-204Cl$_2$ Tl-204F$_2$ (Tl-204)$_2$O Tl-204I |

TABLE 117

| ISOTOPE | HALF-LIFE | ENERGY | RADIOACTIVE REACTIVE SPUTTER-GAS |
|---|---|---|---|
| Tm-165 | 30.1 hours | 84.2 KeV 100 KeV Beta Part. | Tm-165Br$_3$ Tm-165Cl$_3$ Tm-165F$_3$ Tm-165I$_{32}$ |
| Tm-167 | 9.4 days | 208 KeV | Tm-167Br$_3$ Tm-167Cl$_3$ Tm-167F$_3$ Tm-167I$_{32}$ |
| Tm-170 | 128.6 days | 883 KeV Beta Part. | Tm-170Br$_3$ Tm-170Cl$_3$ Tm-170F$_3$ Tm-170I$_{32}$ |

TABLE 118

| ISOTOPE | HALF-LIFE | ENERGY | RADIOACTIVE REACTIVE SPUTTER-GAS |
|---|---|---|---|
| H-3 | 12.26 years | 18.6 KeV Beta Particle | H-3$_2$ |

TABLE 119

| ISOTOPE | HALF-LIFE | ENERGY | RADIOACTIVE REACTIVE SPUTTER-GAS |
|---|---|---|---|
| W-185 | 76 days | 432 KeV Beta Part. (0.019% 125 gamma) | W-185F$_6$ W-185(CO)$_6$ |
| W-187 | 1 day | 479–685 KeV | W-187F$_6$ W-187(CO)$_6$ |

TABLE 120

| ISOTOPE | HALF-LIFE | ENERGY | RADIOACTIVE REACTIVE SPUTTER-GAS |
|---|---|---|---|
| U-231 | 4.2 days | 25.6–84.2 KeV | U-231F$_6$ U-231F$_5$ U-231F$_4$ U-231Cl$_5$ U-231I$_4$ |
| U-237 | 6.75 days | 59–208 KeV 248 KeV Beta Part. | U-237F$_6$ U-237F$_5$ U-237F$_4$ U-237Cl$_5$ U-237I$_4$ |

TABLE 121

| ISOTOPE | HALF-LIFE | ENERGY | RADIOACTIVE REACTIVE SPUTTER-GAS |
|---|---|---|---|
| V-48 | 15.9 days | 984 KeV | V-48F$_5$ V-48Cl$_4$ V-48OCl$_3$ |

TABLE 122

| ISOTOPE | HALF-LIFE | ENERGY | RADIOACTIVE REACTIVE SPUTTER-GAS |
|---|---|---|---|
| Zr086 | 16.5 hours | 243 KeV | Zr-86Cl$_4$ Zr-86F$_4$ Zr-86O |
| Zr-88 | 83.4 days | 393 KeV | Zr-88Cl$_4$ Zr-88F$_4$ Zr-88O |
| Zr-93 | 1000 years | 30.4 KeV (gamma) 60 KeV Beta Part. | Zr-93Cl$_4$ Zr-88F$_4$ Zr-88O |

TABLE 123

| Radio-nuclide | T-1/2 | Beta Particle Energy | Gamma Compn. |
|---|---|---|---|
| Pd-112 | 21.0 hours | 300 KeV | 20% 18.5 KeV |
| Th-231 | 25.5 hours | 299 KeV | 100% 84.2 KeV |
| Tm-165 | 30.1 hours | 100 KeV | 0.004% 15–60.4 KeV |
| Ni-66 | 54.6 hours | 200 KeV | — |
| Dy-166 | 81.5 hours | 400 KeV | 100% 82.4 KeV |
| U-237 | 6.75 days | 248 KeV | 59–208 KeV |
| Er-169 | 9.6 days | 340 KeV | 0.1% 8 KeV |
| Pu-246 | 10.9 days | 150–350 KeV | 44–224 KeV |
| P-33 | 25.3 days | 249 KeV | — |
| W-185 | 74.8 days | 433 KeV | 0.01% 125 KeV |
| S-35 | 87.2 days | 167 KeV | — |
| Os-194 | 6.0 years | 54 KeV | 10% 43.0 KeV |
| H-3 | 12.26 years | 18.6 KeV | — |
| Ca-45 | 163.8 days | 257 KeV | — |

TABLE 124

| Radio-nuclide | T-1/2 | Beta Particle Energy | Gamma Compn. |
|---|---|---|---|
| Ru-106 | 367 days | 39.2 KeV | — |
| Pb-210 | 21 years | 15–61 KeV | 4.1% 46.5 KeV |
| Sr-90 | 29.0 years | 546 KeV | — |
| Ni-63 | 92.0 years | 67 KeV | — |
| Sm-151 | 93 years | 55–76 KeV | 21.6 KeV |
| Si-32 | 650 years | 210 KeV | — |
| Se-79 | 1000 years | 154 KeV | — |
| Rb-87 | 1000 years | 274 KeV | — |
| Zr-93 | 1000 years | 60 KeV | — |
| Tc-99 | 1000 years | 292 KeV | — |
| Pd-107 | 1000 years | 35 KeV | — |
| I-129 | 1000 years | 189 KeV | 39.6 KeV |
| Cs-135 | 1000 years | 210 KeV | — |
| Re-187 | 1000 years | 8 KeV | — |
| Ra-228 | 1000 years | 24–48 KeV | 10–26 KeV |

TABLE 125

| Coating | Z Atomic Number | Density gm/cm | 100 KeV R (micron) Distance ×25%/×50% |
|---|---|---|---|
| Carbon | 6 | 3.51 | 36/72 |
| Auminum | 13 | 2.7 | 46/-- |
| Titanium | 22 | 4.5 | 28/56 |
| Vanadium | 23 | 5.96 | 21/42 |
| Chromium | 24 | 7.20 | 17/35 |

TABLE 126

| Coating | Symbol | Z Atomic Number | M Atomic Weight |
|---|---|---|---|
| Hafnium | Hf | 72 | 178.5 |
| Tantalum | Ta | 73 | 180.9 |
| Tungsten | W | 74 | 183.8 |
| Rhenium | Re | 75 | 186.2 |
| Osmium | Os | 76 | 190.2 |
| Uranium | U | 92 | 238.0 |

TABLE 127

| Coating | Symbol | Z Atomic Number |
|---|---|---|
| Zirconium | Zr | 40 |
| Molybdenum | Mo | 42 |
| Palladium | Pd | 46 |
| Silver | Ag | 47 |
| Cadmium | Cd | 48 |
| Indium | In | 49 |
| Tin | Sn | 50 |
| Antimony | Sb | 51 |
| Tellurium | Te | 52 |

TABLE 128

| Coating | Symbol | Z Atomic Number |
|---|---|---|
| Magnesium | Mg | 12 |
| Aluminum | Al | 13 |
| Silicon | Si | 14 |
| Phosphorous | P | 15 |
| Titanium | Ti | 22 |
| Vanadium | v | 23 |
| Chromium | Cr | 24 |
| Nickel | Ni | 28 |
| Copper | Cu | 29 |

TABLE 129

| | |
|---|---|
| Sphere, 200 micron substrate 25 micron coat: | 12.5 Ci/gram |
| Sphere, 300 micron substrate 25 micron coat: | 6.0 Ci/gram |
| Sphere, 400 micron substrate 25 micron coat: | 3.52 Ci/gram |
| Sphere, 600 micron substrate 25 micron coat: | 1.63 Ci/gram |
| Sphere, 600 micron substrate 50 micron coat: | 750 mCi/gram |
| Microfilament 400 micron substrate (8-0 suture) 10 micron coat: | 388 mCi/gram |
| Microfilament 300 micron substrate (9-0 suture) 25 micron coat: | 196 mCi/gram |
| Microfilament 300 micron substrate (9-0 suture) 30 micron coat: | 161 mCi/gram |
| Microfilament 150 micron substrate 10 micron coat: | 1.00 Ci/gram |
| Microfilament 150 micron substrate 25 micron coat: | 360 mCi/gram |
| Microfilament 150 micron substrate 50 micron coat: | 159 mCi/gram |
| Microfilament 15 micron substrate 10 micron coat: | 3.9 Ci/gram |
| Microfilament 15 micron substrate 20 micron coat: | 1.59 Ci/gram |

TABLE 130

RADIOACTIVE MICROSPHERES, 200 MICRON SUBSTRATE FOR PERMANENT IMPLANTATION INTO TISSUE
25 MICRON COAT

| TARGET MATERIAL | ACTIVATION CROSS-SECTION (BARNS) | ACTIVITY PRODUCED BY FLUX $10^{12}$N/CM$^2$/S | FINAL PRODUCT | T-1/2 | ENERGY | OTHER ISOTOPES PRESENT |
|---|---|---|---|---|---|---|
| Dysprosium Dy | 790 Barns | 57 Ci/g/4 h | Dy-165 | 2.35 hrs | 95–630 KV | Dy-159 Dy-166 |

TABLE 131

RADIOACTIVE MICROSPHERES, 300 MICRON SUBSTRATE FOR PERMANENT IMPLANTATION INTO TISSUE
25 MICRON COAT

| TARGET MATERIAL | ACTIVATION CROSS-SECTION (BARNS) | ACTIVITY PRODUCED BY FLUX $10^{12}$N/CM$^2$/S | FINAL PRODUCT | T-1/2 | ENERGY | OTHER ISOTOPES PRESENT |
|---|---|---|---|---|---|---|
| Gold Au | 98 Barns | 6.2 Ci/g/wk 8.0 Ci/g/wk | Au-198 | 2.7 d | 412 KeV | Au-199 |
| Holmium Ho | 60 Barns | 2.7 Ci/g/wk 5.9 Ci/g/satn. | Ho-166 | 27 hrs | 80 KeV | — |
| Lutecium Lu | 100 Barns | 4.3 Ci/g/wk 8.5 Ci/g/wk 8.3 Ci/g/sat. | Lu-177 | 6.7 d | 210 KeV | Lu-176m Yb-169 Yb-175 |

TABLE 132

RADIOACTIVE MICROSPHERES, 600 MICRON SUBSTRATE FOR PERMANENT IMPLANTATION INTO TISSUE
25 MICRON COAT

| TARGET MATERIAL | ACTIVATION CROSS-SECTION (BARNS) | ACTIVITY PRODUCED BY FLUX $10^{12}$N/CM$^2$/S | FINAL PRODUCT | T-1/2 | ENERGY | OTHER ISOTOPES PRESENT |
|---|---|---|---|---|---|---|
| Rhenium Re | 44 Barns | 2.5 Ci/g/wk 3.8 Ci/g/satn. | Re-186 | 90 hr | 137 KeV + 1.07 MeV Beta | Re-188 |
| Re | 43 Barns | 2.4 Ci/g/24 h 3.8 Ci/g/wk | Re-188 | 17 hr | 155 KeV + 2.12 MeV Beta | Re-186 |
| Samarium Sm | 37 Barns | 1.2 Ci/g/24 hr 3.5 Ci/g/wk 4.0 Ci/g/satn. | Sm-153 | 47 hr | 100 KeV | Sm-155 Eu-155 Eu-156 |
| Enriched Calcium-46 Ca-46 | | Depends on Enrichment | Sc-47 | 3.4 d | 160 KeV | Ca-45 Ca-47 Ca-49 Sc-49 |
| Praseodymium Pr | 11.0 Barns | 0.75 Ci/g/24 h 1.3 Ci/g/sat. | Pr-142 | 19.2 hr | 2.15 MeV Beta Part. | — |

TABLE 133

RADIOACTIVE MICROSPHERES, 600 MICRON SUBSTRATE FOR PERMANENT IMPLANTATION INTO TISSUE
50 MICRON COAT

| TARGET MATERIAL | ACTIVATION CROSS-SECTION (BARNS) | ACTIVITY PRODUCED BY FLUX $10^{12}$ N/CM$^2$/S | FINAL PRODUCT | T-1/2 | ENERGY | OTHER ISOTOPES PRESENT |
|---|---|---|---|---|---|---|
| Antimony Sb | 3.9 Barns | 380 mCi/g/week 520 mCi/g/sat. | Sb-122 | 2.74 days | 570 KeV | Sb-122m Sb-124m Sb-124 |
| Arsenic As | 4.2 Barns | 430 mCi/g/24 h 920-mCi/g/saturate | As-76 | 26.5 hrs | 560 KeV | — |
| Copper Cu | 3.0 Barns | 270 mCi/g/8 h 760 mCi/g/sat. | Cu-64 | 12.8 hrs | 510 KeV | Cu-66 |
| Lanthanum La | 8.2 barns | 860 mCi/g/wk 960 mCi/g/sat. | La-140 | 40.2 hr | 1600 KeV | — |
| Tungsten W | 9.7 Barns | 425 mCi/g/wk 850 mCi/g/sat. | W-187 | 24 hr | 72–686 KeV | W-181 W-185 |
| Ytterbium-169 Yb-169 | 15.4 Barns | 180 mCi/g/wk 0.55 Ci/g/mo | Yb-169 | 31 d | 63–198 KeV | Yb-175 Yb-177 Lu-177 |
| Palladium (Enriched) Pd | 2.7 Barns | 290 mCi/g/24 h 410 mCi/g/satn. (Depends upon enrichment) | Pd-109 Pd-109m | 14 hr | 88 KeV | Pd-103 |

TABLE 134

MULTILAYERED RADIOACTIVE MICROSPHERES, 200 MICRON SUBSTRATE FOR TEMPORARY IMPLANTATION INTO TISSUE
25 MICRON COAT

| TARGET MATERIAL | ACTIVATION CROSS-SECTION (BARNS) | ACTIVITY PRODUCED BY FLUX $10^{12}$ N/CM$^2$/S | FINAL PRODUCT | T-1/2 | ENERGY | OTHER ISOTOPES PRESENT |
|---|---|---|---|---|---|---|
| Europium Eu | 3360 Barns | 0.31 Ci/g/wk 1.2 Ci/g/mo 15 Ci/g/yr | Eu-152 | 12.4 yr | 340–1410 KeV | Eu-152m Eu-154 |
| Iridium Ir | 370 Barns | 1.7 Ci/g/wk 6.5 Ci/g/mo 32 Ci/g/satn. | Ir-192 | 74 d | 316 KeV | Ir-194 |

TABLE 135

MULTILAYERED RADIOACTIVE MICROSPHERES, 600 MICRON SUBSTRATE FOR TEMPORARY IMPLANTATION INTO TISSUE
25 MICRON COAT

| TARGET MATERIAL | ACTIVATION CROSS-SECTION (BARNS) | ACTIVITY PRODUCED BY FLUX $10^{12}$ N/CM$^2$/S | FINAL PRODUCT | T-1/2 | ENERGY | OTHER ISOTOPES PRESENT |
|---|---|---|---|---|---|---|
| Enriched Calcium-46 Ca-46 | 22 Barns | 380 mCi/g/wk 1.4 Ci/g/mo 7.9 Ci/g/satn. | Sc-46 | 84 d | 1120 KeV | Ca-45 |
| Thulium Tm | 130 Barns | 0.39 Ci/g/wk 1.4 Ci/g/mo 10 Ci/g/yr | Tm-170 | 127 d | 7–84 KeV | — |

TABLE 136

MULTILAYERED RADIOACTIVE MICROSPHERES, 600 MICRON SUBSTRATE FOR TEMPORARY IMPLANTATION INTO TISSUE
25 MICRON COAT

| TARGET MATERIAL | ACTIVATION CROSS-SECTION (BARNS) | ACTIVITY PRODUCED BY FLUX $10^{12} N/CM^2/S$ | FINAL PRODUCT | T-1/2 | ENERGY | OTHER ISOTOPES PRESENT |
|---|---|---|---|---|---|---|
| Tantalum Ta | 19 Barns | 60 mCi/g/wk 220 mCi/g/mo 1400 mCi/g/yr | Ta-182 | 115 d | 68–1230 KeV | Ta-183 |
| Terbium Tb | 22 Barns | 120 mCi/g/wk 440 mCi/g/mo 2200 mCi/g/satn. | Tb-160 | 74.2 d | 87–966 KeV | — |

TABLE 137

MULTILAYERED RADIOACTIVE MICROSPHERES, 600 MICRON SUBSTRATE FOR TEMPORARY IMPLANTATION INTO TISSUE
50 MICRON COAT

| TARGET MATERIAL | ACTIVATION CROSS-SECTION (BARNS) | ACTIVITY PRODUCED BY FLUX $10^{12} N/CM^2/S$ | FINAL PRODUCT | T-1/2 | ENERGY | OTHER ISOTOPES PRESENT |
|---|---|---|---|---|---|---|
| Cesium Cs | 33 Barns | 18 mCi/g/wk 63 mCi/g/mo 810 mCi/g/saturate | Cs-134 | 2.1 years | 800 KeV | Cs-134m |

TABLE 138

RADIOACTIVE MICROFILAMENTS, 150 MICRON DIAMETER
10 MICRON ACTIVE COAT
MULTILAYERED RADIOACTIVE MICROFILAMENTS FOR PERMANENT IMPLANTATION

| TARGET MATERIAL | ACTIVATION CROSS-SECTION (BARNS) | ACTIVITY PRODUCED BY FLUX $10^{12} N/CM^2/S$ | FINAL PRODUCT | T-1/2 | ENERGY | OTHER ISOTOPES PRESENT |
|---|---|---|---|---|---|---|
| Gold Au | 98 Barns | 6.2 Ci/g/wk 8.0 Ci/g/wk | Au-198 | 2.7 d | 412 KeV | Au-199 |
| Holmium Ho | 60 Barns | 2.7 Ci/g/wk 5.9 Ci/g/satn. | Ho-166 | 27 hrs | 80 KeV | — |
| Lutecium Lu | 100 Barns | 4.3 Ci/g/wk 8.5 Ci/g/mo 9.3 Ci/g/satn. | Lu-177 | 6.7 d | 210 KeV | Lu-176m Yb-169 Yb-175 |
| Praseodymium Pr | 11.0 Barns | 0.75 Ci/g/24 h 1.3 Ci/g/satn. | Pr-142 | 19.2 hr | 2.15 MeV Beta Particle | — |
| Phenium Re | 44 Barns | 2.5 Ci/g/wk 3.8 Ci/g/satn. | Re-186 | 90 hr | 137 KeV | Re-188 |
| Re | 43 Barns | 2.4 Ci/g/24 hr 3.8 Ci/g/wk | Re-188 | 17 hr | 155 KeV | Re-186 |
| Samarium Sm | 37 Barns | 1.2 Ci/g/24 hr 3.5 Ci/g/wk 4.0 Ci/g/satn. | Sm-153 | 47 hr | 100 KeV | Sm-155 Eu-155 Eu-156 |

TABLE 139

RADIOACTIVE MICROFILAMENTS, 150 MICRON DIAMETER
10 MICRON ACTIVE COAT
MULTILAYERED RADIOACTIVE MICROFILAMENTS FOR PERMANENT IMPLANTATION

| TARGET MATERIAL | ACTIVATION CROSS-SECTION (BARNS) | ACTIVITY PRODUCED BY FLUX $10^{12} N/CM^2/S$ | FINAL PRODUCT | T-1/2 | ENERGY | OTHER ISOTOPES PRESENT |
|---|---|---|---|---|---|---|
| Enriched Calcium-46 Ca-46 | | Depends on Enrichment | Sc-47 | 3.4 d | 160 KeV | Ca-45 Ca-47 Ca-49 Sc-49 |
| Arsenic As | 4.2 Barns | 430 mCi/g/24 h 920 mCi/g/sat. | As-76 | 26.5 hrs | 560 KeV | — |
| Lanthanum La | 8.2 Barns | 860 mCi/g/wk 960 mCi/g/satn. | La-140 | 40.2 hrs | 1600 KeV | — |
| Tungsten W | 9.7 Barns | 425 mCi/g/wk 850 mCi/g/satn. | W-187 | 24 hr | 72–686 KeV | W-181 W-185 |
| Dysprosium Dy | 790 Barns | 57 Ci/g/4 hrs | Dy-165 | 2.35 hrs | 95–630 KV | Dy-159 Dy-166 |

TABLE 140

RADIOACTIVE MICROFILAMENTS, 150 MICRON DIAMETER
50 MICRON ACTIVE COAT
MULTILAYERED RADIOACTIVE MICROFILAMENTS FOR PERMANENT IMPLANTATION

| TARGET MATERIAL | ACTIVATION CROSS-SECTION (BARNS) | ACTIVITY PRODUCED BY FLUX $10^{12} N/CM^2/S$ | FINAL PRODUCT | T-1/2 | ENERGY | OTHER ISOTOPES PRESENT |
|---|---|---|---|---|---|---|
| Ytterbium-169 Yb-169 | 15.4 Barns | 180 mCi/g/wk 0.55 Ci/g/mo | Yb-169 | 31 d | 63–198 KeV | Yb-175 Yb-177 Lu-177 |
| Antimony Sb | 3.9 Barns | 380 mCi/g/wk 520 mCi/g/sat. | Sb-122 Sb-124m | 2.74 days | 570 KeV | Sb-122m Sb-124 |
| Bromine Be | 1.6 Barns | 160 mCi/g/24 h 310 mCi/g/wk 330 mCi/g/satn. | Br-82 | 35.4 hrs | 780 KeV | Br-80 |
| Chromium Cr | 0.69 Barns | 30 mCi/g/wk 95 mCi/g/mo 210 mCi/g/sat. | Cr-51 | 27.8 d | 323 KeV | — |
| Copper Cu | 3.0 Barns | 270 mCi/g/8 hrs 760 mCi/g/sat. | Cu-64 | 12.8 hrs | 510 KeV | Cu-66 |

TABLE 141

RADIOACTIVE MICROFILAMENTS, 150 MICRON DIAMETER
50 MICRON ACTIVE COAT
MULTILAYERED RADIOACTIVE MICROFILAMENTS FOR PERMANENT IMPLANTATION

| TARGET MATERIAL | ACTIVATION CROSS-SECTION (BARNS) | ACTIVITY PRODUCED BY FLUX $10^{12} N/CM^2/S$ | FINAL PRODUCT | T-1/2 | ENERGY | OTHER ISOTOPES PRESENT |
|---|---|---|---|---|---|---|
| Gallium Ga | 2.0 Barns | 330 mCi/g/wk 480 mCi/g/satn. | Ga-72 | 14 hrs | 835–2510 KeV | Ga-70 |
| Germanium Ge | 0.70 Barns | 50 mCi/g/wk 120 mCi/g/mo 160 mCi/g/satn. | Ge-71 | 11 d | 92 KeV | Ge-75 Ge-77 As-77 |
| Mercury Hg | 4.5 Barns | 350 mCi/g/wk 360 mCi/g/satn. | Hg-197 | 65 hr | 77 KeV | Hg-199m Hg-203 Hg-205 |

TABLE 142

RADIOACTIVE MICROFILAMENTS, 150 MICRON DIAMETER
10 MICRON ACTIVE COAT
MULTILAYERED RADIOACTIVE MICROFILAMENTS FOR PERMANENT IMPLANTATION

| TARGET MATERIAL | ACTIVATION CROSS-SECTION (BARNS) | ACTIVITY PRODUCED BY FLUX $10^{12}$ N/CM$^2$/S | FINAL PRODUCT | T-1/2 | ENERGY | OTHER ISOTOPES PRESENT |
|---|---|---|---|---|---|---|
| Palladium Pd | 2.7 Barns | 290 mCi/g/24 h 410 mCi/g/satn. | Pd-109 | 14 hr | 88 KeV | Pd-103 Pd-109m Pd-111 Ag-111 |
| Sodium Na | 0.54 Barns | 260 mCi/g/24 h 390 mCi/g/satn. | Na-24 | 15 hr | 1370–2750 KeV | — |
| Yttrium Y | 1.3 Barns | 52 mCi/g/wk 190 mCi/g/mo 230 mCi/g/satn. | Y-90 | 64.2 hr | 2270 KeV Beta Particle | — |
| Phosphorous P | 0.19 Barns | 25 mCi/g/wk 67 mCi/g/mo 100 mCi/g/satn. | P-32 | 14.3 d | 1.7 MeV Beta only | — |

TABLE 143

RADIOACTIVE MICROFILAMENTS, 150 MICRON DIAMETER
10 MICRON ACTIVE COAT
MULTILAYERED RADIOACTIVE MICROFILAMENTS FOR TEMPORARY REMOVABLE IMPLANTATION

| TARGET MATERIAL | ACTIVATION CROSS-SECTION (BARNS) | ACTIVITY PRODUCED BY FLUX $10^{12}$ N/CM$^2$/S | FINAL PRODUCT | T-1/2 | ENERGY | OTHER ISOTOPES PRESENT |
|---|---|---|---|---|---|---|
| Cobalt Co | 37 Barns | 23 mCi/g/wk 87 mCi/g/mo 1060 mCi/g/yr | Co-60 | 5.26 yr | 1.25 KeV | — |
| Europium Eu | 360 Barns | 0.31 Ci/g/wk 1.2 Ci/g/mo 15 Ci/g/yr | Eu-152 | 12.4 yr | 340–1410 KeV | Eu-152m Eu-154 |
| Iridium Ir | 370 Barns | 1.7 Ci/g/wk 6.5 Ci/g/mo 32 Ci/g/satn. | Ir-192 | 74 d | 316 KeV | Ir-194 |
| Enriched Calcium-46 Ca-46 | 22 Barns | 380 mCi/g/wk 1.4 Ci/g/mo 7.9 Ci/g/satn | Sc-46 | 84 d | 1120 KeV | Ca-45 |

TABLE 144

RADIOACTIVE MICROFILAMENTS, 150 MICRON DIAMETER
10 MICRON ACTIVE COAT
MULTILAYERED RADIOACTIVE MICROFILAMENTS FOR TEMPORARY REMOVABLE
IMPLANTATION

| TARGET MATERIAL | ACTIVATION CROSS-SECTION (BARNS) | ACTIVITY PRODUCED BY FLUX $10^{12}$N/CM$^2$/S | FINAL PRODUCT | T-1/2 | ENERGY | OTHER ISOTOPES PRESENT |
|---|---|---|---|---|---|---|
| Thulium Tm | 130 Barns | 0.39 Ci/g/wk 1.4 Ci/g/mo 10 Ci/g/yr | Tm-170 | 127 d | 7–84 KeV | — |
| Tantalum Ta | 19 Barns | 60 mCi/g/wk 220 mCi/g/mo 1400 mCi/g/yr | Ta-182 | 115 d | 68–1230 KeV | Ta-183 |
| Terbium Tb | 22 Barns | 120 mCi/g/wk 440 mCi/g/mo 2200 mCi/g/satn. | Tb-160 | 74.2 d | 87–966 KeV | — |

TABLE 145

RADIOACTIVE MICROFILAMENTS, 150 MICRON DIAMETER
50 MICRON ACTIVE COAT
MULTILAYERED RADIOACTIVE MICROFILAMENTS FOR TEMPORARY REMOVABLE
IMPLANTATION

| TARGET MATERIAL | ACTIVATION CROSS-SECTION (BARNS) | ACTIVITY PRODUCED BY FLUX $10^{12}$N/CM$^2$/S | FINAL PRODUCT | T-1/2 | ENERGY | OTHER ISOTOPES PRESENT |
|---|---|---|---|---|---|---|
| Cesium Cs | 33 Barns | 18 mCi/g/wk 63 mCi/g/mo 810 mCi/g/sat. | Cs-134 | 2.1 yrs | 800 KeV | Cs-134m |
| Hafnium Hf | 2.7 Barns | 15 mCi/g/wk 51 mCi/g/mo 250 mCi/g/satn. | Hf-175 | 70 d | 343 KeV | Hf-181 |
| Hf | 3.5 Barns | 28 mCi/g/wk 95 mCi/g/mo 320 mCi/g/satn. | Hf-181 | 45 d | 482 KeV | Hf-175 |
| Indium In | 2.37 Barns | 27 mCi/g/wk 93 mCi/g/mo 330 mCi/g/satn. | In-114m | 50 d | 190 KeV | In-116m In-114 |
| Protactinium Pa | 7.3 Barns | 72 mCi/g/wk 230 mCi/g/mo 510 mCi/g/satn. | Pa-233 | 27.0 d | 310 KeV | Th prod. |
| Mercury Hg | 1.13 Barns | 7.3 mCi/g/wk 26 mCi/g/mo 91 mCi/g/satn. | Hg-203 | 47.0 d | 279 KeV | Hg-197 |

TABLE 146

15 MICRON DIAMETER WITH 10 MICRON ACTIVE COAT
or 400 MICRON DIAMETER (8-0 SUTURE) WITH 10 MICRON ACTIVE COAT
MULTILAYERED RADIOACTIVE MICROFILAMENTS FOR PERMANENT IMPLANTATION

| TARGET MATERIAL | ACTIVATION CROSS-SECTION (BARNS) | ACTIVITY PRODUCED BY FLUX $10^{12}$N/CM$^2$/S | FINAL PRODUCT | T-1/2 | ENERGY | OTHER ISOTOPES PRESENT |
|---|---|---|---|---|---|---|
| Dysprosium Dy | 790 Barns | 57 Ci/g/4 hrs | Dy-165 | 2.35 hrs | 95–630 KV | Dy-159 Dy-166 |
| Gold Au | 98 Barns | 6.2 Ci/g/wk 8.0 Ci/g/wk | Au-198 | 2.7 d | 412 KeV | Au-199 |
| Holmium Ho | 60 Barns | 2.7 Ci/g/wk 5.9 Ci/g/satn. | Ho-166 | 27 hrs | 80 KeV | — |
| Lutecium Lu | 100 Barns | 4.3 Ci/g/wk 8.5 Ci/g/mo 9.3 Ci/g/satn. | Lu-177 | 6.7 d | 210 KeV | Lu-176m Yb-169 Yb-175 |

TABLE 147

15 MICRON DIAMETER WITH 10 MICRON ACTIVE COAT
OR 400 MICRON DIAMETER (8-0 SUTURE) WITH 10 MICRON ACTIVE COAT
MULTILAYERED RADIOACTIVE MICROFILAMENTS FOR PERMANENT IMPLANTATION

| TARGET MATERIAL | ACTIVATION CROSS-SECTION (BARNS) | ACTIVITY PRODUCED BY FLUX $10^{12}$N/CM$^2$/S | FINAL PRODUCT | T-1/2 | ENERGY | OTHER ISOTOPES PRESENT |
|---|---|---|---|---|---|---|
| Rhenium Re | 44 Barns | 2.5 Ci/g/wk 3.8 Ci/g/satn. | Re-186 | 90 hr | 137 KeV | Re-188 |
| Re | 43 Burns | 2.4 Ci/g/24 hr 3.8 Ci/g/wk | Re-188 | 17 hr | 155 KeV | Re-186 |
| Samarium Sm | 37 Barns | 1.2 Ci/g/24 hr 3.5 Ci/g/wk 4.0 Ci/g/satn. | Sm-153 | 47 hr | 100 KeV | Sm-155 Eu-155 Eu-156 |
| Enriched Calcium-46 Ca-46 | | Depends on Enrichment | Sc-47 | 3.4 d | 160 KeV | Ca-45 Ca-47 Ca-49 Sc-49 |

TABLE 148

15 MICRON DIAMETER WITH 20 MICRON ACTIVE COAT
OR 300 MICRON DIAMETER (9-0 SUTURE) WITH 30 MICRON ACTIVE COAT
MULTILAYERED RADIOACTIVE MICROFILAMENTS FOR PERMANENT IMPLANTATION

| TARGET MATERIAL | ACTIVATION CROSS-SECTION (BARNS) | ACTIVITY PRODUCED BY FLUX $10^{12}$N/CM$^2$/S | FINAL PRODUCT | T-1/2 | ENERGY | OTHER ISOTOPES PRESENT |
|---|---|---|---|---|---|---|
| Praseodymium Pr | 11.0 Barns | 0.75 Ci/g/24 h 1.3 Ci/g/satn | Pr-142 | 19.2 hr | 2.15 MeV Beta Particle | — |
| Arsenic As | 4.2 Barns | 430 mCi/g/24 h 920 mCi/g/sat. | As-76 | 26.5 hrs | 560 KeV | — |
| Lanthanum La | 8.2 Barns | 860 mCi/g/wk 960 mCi/g/satn. | La-140 | 40.2 hr | 1600 KeV | — |
| Tungsten W | 9.7 Barns | 425 mCi/g/wk 850 mCi/g/satn. | W-187 | 24 hr | 72–686 KeV | W-181 W-185 |

TABLE 149

15 MICRON DIAMETER WITH 10 MICRON ACTIVE COAT
OR 400 MICRON DIAMETER (8-0 SUTURE) WITH 10 MICRON ACTIVE COAT
MULTILAYERED RADIOACTIVE MICROFILAMENTS FOR TEMPORARY REMOVABLE
IMPLANTATION

| TARGET MATERIAL | ACTIVATION CROSS-SECTION (BARNS) | ACTIVITY PRODUCED BY FLUX $10^{12} N/CM^2/S$ | FINAL PRODUCT | T-1/2 | ENERGY | OTHER ISOTOPES PRESENT |
|---|---|---|---|---|---|---|
| Cobalt Co | 37 Barns | 34 mCi/g/wk 87 mCi/g/mo 1060 mCi/g/yr | Co-60 | 5.26 yr | 1.25 KeV | — |
| Europium Eu | 360 Barns | 0.31 Ci/g/wk 1.2 Ci/g/mo 15 Ci/g/yr | Eu-152 | 12.4 yr | 340–1410 KeV | Eu-152m Eu-154 |
| Iridium Ir | 370 Barns | 1.7 Ci/g/wk 6.5 Ci/g/mo 32 Ci/g/satn. | Ir-192 | 74 d | 316 KeV | Ir-194 |
| Enriched Calcium-46 Ca-46 | 22 Barns | 380 mCi/g/wk 1.4 Ci/g/mo 7.9 Ci/g/satn | Sc-46 | 84 d | 1120 KeV | Ca-45 |
| Thulium Tm | 130 Barns | 0.39 Ci/g/wk 1.4 Ci/g/mo 10 Ci/g/yr | Tm-170 | 127 d | 7–84 KeV | — |

TABLE 150

15 MICRON DIAMETER WITH 20 MICRON ACTIVE COAT
OR 300 MICRON DIAMETER (9-0 SUTURE) WITH 30 MICRON ACTIVE COAT
MULTILAYERED RADIOACTIVE MICROFILAMENTS FOR TEMPORARY REMOVABLE
IMPLANTATION

| TARGET MATERIAL | ACTIVATION CROSS-SECTION (BARNS) | ACTIVITY PRODUCED BY FLUX $10^{12} N/CM^2/S$ | FINAL PRODUCT | T-1/2 | ENERGY | OTHER ISOTOPES PRESENT |
|---|---|---|---|---|---|---|
| Tantalum Ta | 19 Barns | 60 mCi/g/wk 220 mCi/g/mo 1400 mCi/g/yr | Ta-182 | 115 d | 68–1230 KeV | Ta-183 |
| Terbium Tb | 22 Barns | 120 mCi/g/wk 440 mCi/g/mo 2200 mCi/g/satn. | Tb-160 | 74.2 d | 87–966 KeV | — | that the beta particles travel multiplied by 25% and 50% corresponds roughly to the coating thickness (in microns) of listed material required to reduce the KE of the beta particles by 25% and 50%, respectively.

The preferred target materials used to produce bremsstrahlung X-rays from the beta particle collisions are listed in table 126. The bremsstrahlung material is a coating applied over the beta-KE modulation coat that is in turn placed over the radioactive beta-particle-producing coat. To obtain the most efficient conversion of beta particle KE to bremsstrahlung radiation, higher Z target materials are preferred since the energy radiated is approximately proportional to E×Z.

The bremsstrahlung coat is in turn coated with a material that will effectively produce either K-fluorescent or L-fluorescent Low Energy X-rays. The preferred materials for this coat are listed in table 127.

Either the bremsstrahlung coat or the K-fluorescent coat is in turn coated with a material that will effectively produce Auger electrons. The preferred materials for this coat are listed in table 128.

In use, a non-tissue absorbable tissue-compatible fabric containing multilayer radioactive microspheres is placed into a cavity being treated. Either gauze packing or suture can be used to immobilize this temporary removable fabric multilayer radioactive microsphere. After an adequate treatment time, the fabric multilayer radioactive microsphere is removed. Because the fabric multilayer radioactive microsphere incorporates the entire wide range of radionuclides used in single multilayer radioactive microsphere, a great flexibility in treatment is provided. Using low energy multilayer radioactive microsphere surgical fabric, the patient may be discharged home with the low energy temporary removable implant in place and return at a later date for implant removal.

Tumors are detected either visually or through the use of imaging devices such as CAT, MR, PET or the like. A determination is made as to whether permanent implants or temporary multilayer radioactive implants should be used generally based on location of the tumor. A determination is then made concerning the use of temporary or permanent multilayer radioactive appliances. This determination is principally based on the location of the tissue.

Temporary implants are inserted for the required amount of time or permanent implants of selected half-lifes and energy levels are implanted for treatment. Scanning may be utilized both to aid in the proper implanting location or to monitor what has been implanted already.

To utilize temporary implants, generally needles formed from the multilayer wires, plaques such as ocular plaques or radioactive wires are inserted in accessible sites. For example, the very thin needles formed as wires and cut to size may be inserted at spaced locations through the epidermal layer or mucus membranes into the tumor. The energy of the temporary multilayer radioactive implants may be relatively high and the half-lives relatively long because of the temporary implantation.

In the case of needles, the needles may be inserted directly through the skin spaced apart from each other to achieve an appropriate energy absorbed by the tissue. This may require either lower energy needles near the center of the tumor and higher energy extending outwardly where the additive effect of the radiation is lower and need for radiation higher or a closer spacing of the needles near the outside of the tumor. Placement of the needles may be controlled by sonograms and a computer to make the appropriate configuration.

With a wire, a relatively small needle may be used because of the thinness and compactness of the wire or ribbon and a pattern may be sewn under the control of a imaging device and computer to apply the optimum field. To aid in the versatility of this approach, the needles may have higher energy radiation at the outer ends of the needle and lower in the center to aid in applying the correct concentration or where the wire is to be threaded, a controlled variation in energy may be created. The needle used to thread wire through a tumor or ribbon through a tumor may be as small in diameter as 21 or 22 gauge to permit ready insertion through tissues.

Relatively small intracavitary containers may be used to implant temporarily radioactive spheres in a safe manner without excessive dilation of body parts. These may be inserted in a conventional manner except that reduced dilation is required. Such intracavitary containers may be inserted and later removed from the bladder, cervix and the like.

Fabric may be used to quickly supply a contoured radiation over wide areas such as the chest. It is laid over the entire area. Stiff ribbon may be used to supply microspheres quickly through a tumor.

Permanent multilayer radioactive implants with low half-lifes or low energy are permanently implanted. Generally, microspheres are injected for this purpose and in some embodiments, may be injected percutaneously through the mucus membrane or the skin using an injector gun with a needle smaller than 19 gauge and preferably being 21 or 22 gauge.

Relatively small intracavitary containers may be used to implant temporarily radiactive spheres in a safe manner without excessive dilation of body parts. These may be inserted in a conventional manner without excessive dilation of body parts. These may be inserted in a conventional manner except that reduced dilation is required. Such intracavitary containers may be inserted and later removed from the bladder, cervix and the like.

Fabric may be used to quickly supply a contoured radiation intraoperatively over wide areas such as the chest and abdomen. It is laid over the entire area. Stiff ribbon may be used to supply microspheres quickly through a tumor.

In implanting sutures, an anchoring seed is attached to the end of a radioactive ribbon or suture to be implanted. This is driven through an implantation needle into the human tumor tissues with a stylet under fluoroscopy visualization until the anchor seed just protrudes beyond the needle tip in the patent's tumor tissue. A seed placed at the end of a suture will anchor the suture into human tumor tissues. The needle is then withdrawn over the stylet, leaving the anchor seed and its attached suture in the human tumor tissue. The stylet is then twisted and gently withdrawn, leaving the radioactive suture material implanted in the patient's tumor.

To produce varied X-ray energies and delivery of these rays over varied time periods, such as for example, $X\text{-ray}_1$ with $\text{energy}_1$ delivered to a tumor by a seed for the duration $\text{time}_1$; $X\text{-ray}_2$ with $\text{energy}_2$ delivered to a tumor by a seed for a duration of $\text{time}_2$; and so on, a seed may have several coats of different beta-producing radionuclides which are applied to the seed. Each radionuclide coat has its own diffusion barrier. Therefore, each additional radionuclide added to the seed design adds two coating steps to the manufacturing process.

For example, a tungsten seed substrate is coated with a layer containing a therapeutic amount of Dy-166 producing 400 KeV beta particles and 82 KeV gamma rays over 4.9 days. This is sealed with a diffusion barrier coat. The 400 KeV beta particles produce bremsstrahlung radiation with an average energy of 266 KeV. This effectively irradiates a larger tumor volume over a shorter period of time, and serves to sterilize microscopic tumor extensions beyond the grossly-visible tumor mass. The irradiation delivered over a short period of time modifies the repopulation dynamics of the tumor, stopping its growth immediately.

Next, a beta particle kinetic energy modulation coat is applied to the seed to reduce the KE of the beta particle of the next coat by fifty percent. A coat of P-33 radionuclide is then applied to produce 249 KeV beta particles over 36.4 days. The KE modulation coat reduces this effective energy to a beta particle energy of 124 KeV, producing bremsstrahlung X-rays with an average energy of 83 KeV. This irradiates a more confined area to a higher dose over a longer period of time.

The continuous low-dose-rate irradiation also has a sparing-effect on the normal surrounding tissues due to repair of sublethal radiation injury. A diffusion coat is applied over this. Another beta particle KE modulation coat is applied, and a coat of radioactive S-35 is applied which produces a beta particle having a KE of 167 KeV over 125.5 days. The second KE modulation coat reduces this KE to 83.5 KeV, and the first, inner KE modulation coat reduces this again to 41.75 KeV, before the beta particles collide with the tungsten substrate seed center.

The average bremsstrahlung energy is then 27.8 KeV. This produces an extremely high tumoricidal dose to a confined tumor volume over an extended time period, allowing for normal tissue repair of sublethal radiation injury. This is covered with a diffusion barrier and a thick protective coating, as previously described.

In FIG. 19, there is shown a diagramatic view showing the treatment of an eye 91 with a multilayered radioactive ocular plaque 108 positioned adjacent to a tumor 110 adjacent to it. The sectional view of the eye 91 is simplified to show only the cornea 112 a lens 113, the sclera 115, the retina 114 and the vitreas center section 117. With this arrangement, the ocular plaque 108 is positioned adjacent to the tumor 110 with its curved portion mounted to irradiate the tumor 110 with relatively high energy radiation.

To treat the tumor 110, after locating it visually, sonographically, radiographically or using MRI, the ocular plaque 108 is selected by size to have minimum overlap on either side of the tumor 110 and to avoid the optic nerve. If the tumor is close to the optic nerve, a plaque having a cup or hemispheric portion is selected and if the tumor is large, a multiple part plaque is used to avoid muscles attached to the globe (rectus muscles). Generally, it is mounted outside the wall of the globe adjacent to the location of the tumor 110 so that its isodose line of 10,000 centi-Gray 121 extends just over and adjacent to the tumor with its lower isodose lines being substantially beyond the tumor so that the highest energy is applied directly to the tumor but normal tissue and adjacent retina is less irradiated.

After the plaque is positioned properly, it is sutured in place for the prescribed period of time, after which the sutures are removed and the plaque removed. The thinness of the plaque facilitates placement, which is usually difficult using state-of-the-art plaques with bulky seed inserts.

In manufacturing the multilayer radioactive microspheres, decisions are first made as to: (1) the intensity of radiation desired; (2) the permanency of the radioactivity desired; (3) the magnetic or ferromagnetic characteristics; (4) tissue compatibility; (5) the ability to be heated by radio frequency radiation for hyperthermia treatment; and (6) its ability to visually identify them such as by X-rays or by magnetic resonance imaging or the like. The substrate is chosen in accordance with this process and the appropriate coats are applied one on the other in intimate contact with each other and with no voids. They are then classified and sent to the customer (when the radioactive microspheres are manufactured directly from radioactive targets or gases). Alternatively, the finished microspheres are manufactured using non-radioactive isotopes. These are sent to be activated in a "neutron oven" and sent to the customer.

The multi-layered radioactive spheres may comprise several distinct structural components. Four of these are basic to produce a functional multilayer radioactive microsphere and two are optional enhancements. The layers may be applied by any of several processes such as by: (1) sputter-deposition of radioactive dielectric or radioactive metal target followed by sputtering, laser ablation, ion-plating, or cathodic arc deposition of multilayers from non-radioactive targets in non-radioactive gases; (2) reactive sputter-deposition or laser-ablation deposition in excited radionuclide gas followed by sputter-deposition or laser-ablation deposition of multilayers from non-radioactive targets in non-radioactive gas; (3) reactive cathodic arc plasma deposition in excited radionuclide gas and cathodic arc multilayer deposition from non-radioactive targets in non-radiaoctive gas; (4) reactive ion beam sputtering using a cathodic arc ion source in excited radionuclide gas and ion-beam self-sputtering multilayer deposition from non-radioactive targets in non-radioactive gas; (5) reactive ion plating in excited radioncuclide gas and multilayer ion-plating from non-radioactaive targets in non-radioactive gas; and (6) cathodic arc plasma deposition of radioactive dielectric and radioactive metal targets followed by cathodic arc deposition of multilayers from non-radioactive targets.

The central core of the multilayer radioactive microsphere is selected for certain functions. For example, it may consist of a starting solid metal microspherical x-ray marker substrate of high atomic number metal or alloy such as iridium, platinum, gold, tantalum, tungsten or lead. Additionally, a lower atomic weight metal or alloy which is satisfactorily visualized on radiographs may be used including molybdenum, indium, lithium, silver, copper, and steel. Platinum, tantalum, gold, and silver are the preferred X-ray marker MRM core substrate materials in the present invention on conventional radiographs.

In another seed design disclosed wherein only magnetic resonance imaging (MRI) of the seed is clinically desirable and X-ray imaging is not necessary, the seed core is composed of a non-metal such as carbon or glass and an outer seed coat produces a an MRI signal (gadolinium) described below produces the seed image. An MRM without a ferromagnetic metal core is essentially non-magnetic. This absence of ferromagnetic metal is advantageous for clinical situations where multiple seeds are implanted in close proximity to critical structures. In such situations, a strong magnetic field produced by MRI equipment may exert enough force to dislodge or move a metal-containing seed. A magnetically dislodged seed in the brain could cause immediate neurologic damage, stoke, or death of the patient. It could also be lost into the cerebrospinal fluid. For MRI imaging, a non-metal containing multilayer radioactive microspheres would be an improvement over the metal encapsulated seeds currently marketed for clinical usage.

The microspherical substrates are then primed by applying a coat several Angstroms thick of the appropriate primer metal, metal oxide, or metal nitride by means of sputtering or reactive sputtering. Preferred primer metals include titanium, aluminum, tin, tantalum, vanadium, titanium nitride, titanium iodide, titanium oxide, titanium carbide, or metal alloys such as stainless steels or nickel alloys. If the coated material does not have good surface comparability with any primer metal, then a graded interface can be created composed of the substrate material and the radioactive dielecric material.

Another layer consists of an uniformly distributed highly controlled spherical radioacative coat produced by either: (1) radio-frequency (rf), laser ablation, magnetron, or planar magnetron sputter-deposition of a dielectric radioactive coat from a radioactive dielectric target material; or (2) dc or rf sputter-deposition from a target composed of pure electrically conducting radioactive metals. This radionuclide coating is a smooth, spherical, uniform, fine-grained, and thin (less than 0.01 mm to 0.045 mm) radioactive layer that uniformly covers the solid micropherical metal core (substrate).

A Also, the target material may be a nonradioactive isotope precursor of the desired radioactive isotope. For example, a multilayer radioactive microsphere containing a primary coat of nonradioactive palladium-102 or samarium-144 is later irradiated with neutrons in a nuclear reactor or in a neutron oven to produce a finished multilayered radioactive microsphere containing radioactive palladium-103 or radioactive samarium-145, respectively.

Another layer may be a dc, rf, laser ablation or magnetron sputter-deposited thin single or multilayered spherical (less than 0.01 millimeter thick) diffusion barrier coating the laminated radionuclide layer.

When the highest quality coat are required, sputter-deposition (direct current dc magnetron, or radio-frequency rf) is the preferred method of producing both the radionuclide coats and diffusion barrier coats because this process is more versatile and is able to produce very thin fine grained smooth surfaces with low peak to valley heights. The sputtering process is highly controllable because many operational parameters of the sputtering process can be changed or adjusted to produce an optimum coat. High coat quality is paid for at the expense of increased manufacturing time due to slower deposition rates and lower energy deposition characteristic of sputter. This may be improved by using large sputter-guns and high-watt power supplies.

Still another layer may be an optional (non-essential) relatively thin (less than 0.01 millimeter thick) rf, magnetron, laser ablation or dc sputter-deposited, or ion-plated, or ion-beam self-sputtered, curvilinear cathodic arc plasma deposited or standard cathodic arc plasma deposited layer or layers of material that have specialized purposes such as magnetic resonance imaging enhancement or positron emission imaging enhancement for seed identification.

A coat such as gadolinium, erbium, terbium, thulium, cerium, cobalt fluoride, dysprosium oxide, dysporsium sulfide, neodymium fluoride, terbium oxide, samarium bromide, thulium oxide, etc. is chosen for the purpose of MRI imaging because of their properties of paramagnetism and high magnetic susceptibility as well as high-boiling point that reduces vacuum welding during coating deposition. Elements or compounds that are suitable or the MRI imaging layer of the present invention include cerium, cobalt fluoride, dysprosium oxide, dysprosium sulfide, erbium, gadolinium, manganese dichloride, neodymium fluoride, samarium bromide, terbium, terbium oxide, thulium and thulium oxide. If lower boiling point materials are to be used, under some circumstances vacuum welding can be prevented by introducing a small amount of oxygen into the sputtering chamber to form an oxide.

Because these elements have sufficiently high boiling points to be effectively coated into the microspheres (boiling points above 2,300 degrees Centigrade are considered higher boiling points for this purpose) and because they have significantly different magnetic susceptibilities, it is possible to separately identify different spheres with different magnetic resonance imaging agents within the same tumor for purposes of tumor dose calculations. To take full advantage of the wide variety of spheres available, it is advantageous to implant more than one type in one procedure into the same tumor. Certain radionuclides with particular energy emissions form a coat that is detected by PET scanner for imaging purposes.

The thick protective coat may be: (1) produced by dc or rf sputtering, planar, magnetron or laser-ablation sputtering, ion plating, ion-beam self-sputtering using a cathodic arc ion source or standard or curvilinear cathodic arc plasma deposition of a metal; or (2) produced by a reactive deposition processes of a compound metal or nonmetallic material.

Some embodiments require low boiling point or soft metals. To coat substrates with these low boiling point metals, such as low boiling point radionuclides without having microspheres fuse together, two targets are used, one of high boiling point harder metal and one of low boiling point softer metal, either simultaneously or one after the other. In the alternative, a target can be prepared with both materials on it. In this specification, high boiling point means in excess of 1,000 degrees Centigrade and low boiling point means lower than 1,000 degrees Centigrade.

The term "high boiling point metals" is used herein to refer to metals or compounds that tend not to vacuum weld when used to coat microspheres in a sputtering apparatus. The term "low boiling point metals" is used herein to refer to metals or compounds that do tend to vacuum weld when used to coat microspheres in a sputtering apparatus. While in many cases these same metals actually do have relatively high boiling points in terms of degrees Centigrade, this is not always the case. Metals with lower boiling points in degrees Centigrade will still be referred to as "high boiling point metals" for the purposes herein.

Thus, the term "boiling point" is correlated with vacuum welding insofar as metals that tend to vacuum weld are generally the same metals that tend to have high sputtering rates also have increasinly-filled "d" shells. Thus, looking at the Periodic Chart of Elements it can be seen that the microsphere coatings used to avoid vacuum-welding come from metals located to the left of the Cu—Ag—Au column, with the Ni—Pd—Pt column being acceptable but marginal, and the Ti—Zr—Ff column being excellent in terms of reduced tendency to vacuum weld.

Metals located in the Periodic Chart of Elements in columns 4, 5, 6, 7, 8, 9 using new notation; or using previous IUPAC notation: columns IVA, VA, VIA, VIIA, and VIIIA (with the exception of Ni, Pd, and Pt from VIIIA) form acceptable microsphere "high-boiling point" coatings to reduce vacuum-welding between microspheres. Be from col 2: B from col 13: C, Si, and Ge from col 14 also form acceptable hard "high boiling point" coatings.

Thus, elements from columns 4, 5, 6, 7, 8, 9 of the Periodic Table of Elements form excellent coatings on microspheres with little tendency to vacuum-weld. These can also be alloyed or laminated with softer metals to form acceptable microsphere coatings. Be from col 2: B from col 13: C, Si, and Ge from col 14 also form acceptable hard coatings.

Elements from column 10 form acceptable to marginally-acceptable coatings that can be produced by adding dopant gas such as oxygen.

Elements in columns 11–17 (previous IUPAC IT, IIB, IIIB, IVB, VB, VIB, VIIB) to the right of column 10 including aluminum, copper, gold, silver, and (excluding carbon-diamond coatings and boron coatings, and silicon and Ge coatings) tend to vacuum-weld and form unacceptable microsphere coatings unless they are alloyed or laminated with a hard element from columns 2–9. Elements from columns 1 and 2 are also unacceptable with the exception of Be and possibly Ra. Another criteria for acceptable microsphere coats is a coat hardness of greater than 4.0 on the MOHS scale. This criteria also applies to compounds whereas the previous periodic table rule only applies to individual elements.

Some acceptable microsphere metal coatings that tend not to vacuum-weld are Be, Ti, Zr, Hf, V, Nb, Ta, Cr, Mo, W, Mn, Tc, Re, Fe, Ru, Ir, Ni (dopant gas necessary), Pd (dopant gas necessary), Pt (dopant gas necessary), B, C (diamond only), Si, Ge. The element may be a radioactive isotope.

Some unacceptable microsphere metal coatings that tend to vacuum-weld are Cu, Ag, Au, Zn, Cd, Hg, Al, Ga, In, Tl, Sn, Pb, P, As, Sb, Bi, S, Se, Te, Po, Cl, Br, I, and At.

Table 59 gives some acceptable compounds for microspherical coats that do not vacuum-weld followed by their hardness rating. One of elements may be radioactive isotope of element. These may be laminated or alloyed with softer metals to form acceptable microsphere coatings.

Table 60 gives some acceptable compounds for microspherical coats that do not vacuum-weld followed by hardness rating. One of elements may be * radioactive isotope of element. These may be laminated or alloyed with softer metals to form acceptable microsphere coatings.

Table 61 shows some acceptable compounds for microspherical coats that do not vacuum-weld followed by hardness rating. One of elements may be radioactive isotope of element. These may be laminated or alloyed with softer metals to form acceptable microsphere coats.

Because of spherical uniform construction, any self-shielding can be compensated for by increasing the seed activity. In the preferred embodiment of this invention, titanium (low atomic weight with minimal shielding of low-energy gamma rays, tissue and corrosion resistant, high hardness and boiling point) is the preferred metal casing used for construction of multilayer radioactive microspheres containing low energy emitting (less than 100 KeV) radionuclides, and tantalum (high atomic weight with some shielding of low-energy gamma rays and very little shielding of high energy gamma rays, highly tissue and corrosion resistant, high hardness and very high boiling point) and is the preferred metal casing used for construction of multi-layer radioactive microspheres containing high-energy emitting (greater than 100 KeV) radionuclides.

If necessary, to reduce porosity or remove crystallization of the coats of the finished product or to improve adhesion between layers after completion of coating, the microspheres may be annealed by heating close to the bulk metal melting temperature in a microsphere bouncing pan.

The sputtering and other deposition techniques as practiced in this invention are substantially adaptations of existing systems and will not be described in detail herein. The adaptation can be made with knowledge of the parameters of the equipment such as the rate of deposition and the materials which can be deposited coupled together with an explanation of the microspheres, wires and fabrics disclosed herein. However, the techniques are modified to form radioactive layers in some embodiments that: (1) sputter or otherwise coat in a high energy vacuum process "high and low boiling point radioactive metals" (as previously defined on page 184) together or as interleaved layers while levitating or bouncing the spheres to prevent sticking of the spheres; and (2) in other embodiments, sputter or otherwise coat in high energy vacuum processes a gaseous radioactive nuclide and non-radioactive metal to form a radioactive metal compound coat because of the reaction of the metal target material and the gas radioactive nuclide to form a radioactive compound coat.

The natural or enriched nonradioactive starting elements must be capable of producing the minimum activities when exposed to a typical neutron flux density of $10^{12}$neutrons/$cm^2$/second shown in table 129 in first entry. Activities per gram of starting material required following neutron activation to produce a minimum therapeutic amount of activity (0.5 mCi/seed, or 0.5 mCi/cm filament), according to volume available on substrate material is shown in the second entry of table 129 opposite the corresponding first entry.

Suitable nonradioactive natural elements or electromagnetically enhanced nonradioactive isotopes suitable for manufacture of multilayered radioactive microspheres or multilayered radioactive filaments of the present invention are summarized below with their typical activities produced by a neutron flux density of $10^{12}$ neutrons/$cm^2$/second. These materials are used to place nonradioactive coats on substrate microspheres or wires, and the finished product is later activated in a neutron oven.

In producing multilayered microspheres from nonradioactive materials that can be later activated the microspheres are "pre-manufactured" in batches of several thousand at a time, stored, and later activated in a neutron flux in small quantities when needed. This is done because the manufacture of thousands of "short-lived" radioactive microspheres directly from radioactive targets or gases may result in production of thousands of seeds that may decay before they could be used, since they would all decay together from the time of manufacture.

In addition to producing radioactive seeds from thermal neutron irradiation of naturally occurring nonradioactive elements, it is also possible to obtain commercially available electromagnetically-enriched elements that contain a higher percentage of the desired nonradioactive isotope. The use of "enriched" nonradioactive isotopes in targets or gases used in the manufacturing of precursor multilayered radioactive microspheres that are later neutron activated permits the use of thinner active coats and production of smaller diameter seeds.

The activities are indicated for types of implants in tables 130–150.

To manufacture radioactive implants from a gas, either in its natural form, or from a gas created from evaporation of a liquid or solid radioactive material into an inert carrier gas such as argon, a radioactive coat on a substrate microsphere or microfilament is produced by reactive sputtering of the radioactive gas with a nonradioactive target material that forms a compound with the element in the sputter gas. Reactive radioactive sputter gases that may be used in production of microspheres of the present invention are listed in the preceding tables 62–122.

Many of these radioactive reactive sputter gases may be prepared direcetly from corresponding solid radioactive materials by reacting an acid with the corresponding radioactive metal or metal oxide at en elevated temperature. For example, uranium-231 hexafluoride may be prepared by reacting anhydrous hydrofluoric acid with uranium-231 dioxide at 450–600 degrees centigrade to form a uranium-231 tetrafluoride. This is then reacted with chlorine trifluoride at 50–150 degrees centigrade to form the uranium-231 hexafluoride sputter gas.

Many of these reactive radioactive sputter gases may also be prepared from corresponding solids or liquids (at room temperature) by means of evaporation into a carrier gas such as argon, hydrogen, nitrogen, oxygen, helium, xenon, or krypton. The vapor pressure of the liquid or solid may be adjusted to the proper level to produce a one percent to twenty percent concentration in an inert carrier gas such as argon or helium by adjusting the temperature or pressure of the evaporation chamber. For some liquids with high vapor pressures at room temperature, it may be necessary to cool the evaporation chamber to maintain the concentration in the carrier gas below five to twenty percent. For heavier liquids or solids it may be necessary to heat the chamber to produce an adequate vapor pressure of the radioactive gas component.

Radioactive liquids with an adequate vapor pressure easily evaporates into an argon carrier gas at low pressures. Because the necessary amount of radioactivity is generally contained within a very small volume of liquid (0.5 cc to 5 cc), it is desirable to dilute the liquid into a carrier gas to a concentration within the range of 0.10% to 20.0% but mostly one to five percent concentration, which then serves as a radioactive reactive sputter gas to produce radioactive coats by vacuum deposition such as physical vapor deposition, chemical vapor deposition, sputtering, cathodic arc deposition, ion beam sputtering, ion plating, et cetera.

In another embodiment of a manufacturing method, microspherical substrates are first prepared by chemical or electroplating processes as described in U.S. Pat. No. 4,323,055 to Kubiatowicz or by sputter-coating with a primer metal and then followed by application of a thick coat of radioactive metal deposition in "wet" solution by means of standard methods of electroplating or electroless plating. These would then be transferred to a vacuum-deposition apparatus to finish the seeds.

For example in the manufacture of a radioactive cesium-131 microsphere, a metal primer coat such as chromium that is compatible with cesium-131 is first sputter-coated over the microspheres. The sputter-coated microspherical substrates are immersed and continuously agitated in a hot aqueous solution of radioactive cesium-131 nitrate. The container bottom is constructed of an electrically conductive material such as carbon graphite coated over an insulating layer such as silicon dioxide. This promotes holding of a surface charge on the container bottom by the "capacitor effect".

The conducting coat on the container bottom is connected to the negative terminal of a D.C. power supply, and the positive terminal is connected to a central carbon electrode inserted into the top part of the solution. The agitated microspherical substrates on the beaker bottom adjacent to the positively charged graphite plate thus become coated with pure radioactive cesium-131 metal. At the carbon-graphite rod electrode, water and oxygen gas are produced. After a coat of radioactive metal 1–50 microns thick is obtained, the microspheres are removed and dried, and placed back into the sputter-deposition apparatus where a diffusion barrier such as titanium nitride is coated over the radioactive coat, and the protective and special coats such as titanium or diamond are sputtered over this.

In the production of the 200 micron diameter microsphere, surface plating iodine-125 onto silver via chemical or electrochemical means does not produce enough activity to be therapeutically useful due to the limited surface area and the fact that the halide coat is only a monolayer thick. To solve this problem, the microspherical substrates are first sputter-coated with silver, then they are chemically plated or electroplated with iodine-125 to form silver iodine-125. Then the coated microspheres are primed with an adhesive metal such as chromium, sputter-coated again with silver and re-plated with I-125. This process may be repeated to produce a multilayered radioactive coat with a therapeutic amount of radioactivity.

The multilayered radioactive microsphere of the present invention requires sputter-application of many different metals and compounds. Some of these adhere well together while others do not. Generally, molybednum, titanium, chromium, and vanadium adhere well to most substrate materials regardless of type. Other metals such as tungsten may adhere poorly. Adhersion may be improved by forming a reactive coat instead of the pure metal, e.g. tungsten nitride rather than tungsten metal. Also, one metal may be used as a "sputtered glue" to improve adhesion. Such materials include aluminum, chromium, steel, and vanadium.

Many types of diffusion barriers composed of a variety of materials form excellent smooth, leakproof barriers to chemical migration. Cold has the additional property of being very insoluble to gases and to material that would tend to sublimate. Thus, gold is the preferred diffusion barrier of the present invention.

Several materials are known to have excellent corrosion resistance as well as compatibility with human tissues. Such materials include titanium, platinum, and gold. Other materials may have excellent anticorrosive properties, but their tissue compatibility remains to be confirmed. Such material include diamond, or diamond-like carbon, titanium nitride, tantalum nitride, and titanium carbide. Thus, the preferred human-tissue compatible anticorrosive coats of the microspheres include platinum and gold.

In FIG. 20, there is shown a simplified view of an injector gun 120 for multilayered radioactive microspheres having a needle 122, a seed container assembly 124, a housing 126, a stylet assembly 128, and a motor assembly 130. The ejector 120 is similar to existing ejectors except that: (1) the needle 122 may have a diameter much smaller than the existing seed guns and is no larger than 20 gauge; (2) there is an electronic radioactive seed detector to indicate when a seed is loaded into the chamber; (3) the seed container assembly is circular in shape; (4) the housing is made of radiation-shielding material to protect the operator's hands; and (5) the seed cartridges contain spherical rather than cylindrical seeds. An existing gun is sold by Mick Radio-Nuclear Instruments, Inc., 1470 Outlook Avenue, Bronx, N.Y., 10465 under the designations Mick Application catalog 7308 and 1-125 Gun catalog 8006.

The seed container assembly 124 is circular in shape and includes a plurality of removable and replaceable seed cartridges, two of which are shown at 124A and 124T, which may include seeds of differing activity or type. The injector gun 20 may be mounted to a robotic arm by four eyelets two of which are shown at 151A and 151C. Only the cartridge 124A will be described since the others are substantially the same.

The cartridge 124A includes a seed compartment 121 containing a plurality of spherical seeds compressed by a spring biased plunger 123 and a rotatable release plate having a slot alignable with any of the cartridges to release one seed into the needle 122 each time the plunger is depressed. Beneath the slot is a pair of spring biased bearings at the distal seed chamber which extend into the needle 122 at a location that blocks the path into the needle 122 until the seed is pushed by the stylet, opening bearings 137. With this arrangement, rotation of the slot permits release of a seed from the selected cartridge.

The housing 126 is made of radiation-shielding material to protect the operator's hands. It includes a tubular wall 126A that slides through the housing at either 2 mm or 5 mm increments along its longitudinal axis with the seed container assembly 124 and motor assembly 130 being mounted to it at a central position. It includes at one end a tissue pad 126B for positioning against tissue 125 to permit passage of needle 122 therethrough into the tissue. When assembly 126 is attached to a robotic arm, tissue pad 126B and wall 126A is fully retracted and not used.

To provide a guide for seeds, the needle 122, which is 20 centimeters long and 21 to 22 gauge to permit deep penetration, extends through the tissue pad and upwardly through the housing to the stylet assembly 128, having an opening to receive seeds located adjacent to the seed container assembly.

To force seeds one at a time through the needle 122, the stylet assembly 128 includes a needle stylet 127, 24 centimeters long that fits into the needle 122 and is able to force a seed therethrough for implanting in tissue and a needle stylet handle 127A, 24 centimeters long for forcing a seed from the needle tip or up to the needle tip for release by moving the tubular wall 124 upwardly.

Elements such as palladium-102 can be made radioactive by neutron irradiation which converts them to radioactive palladium-103. Thus, seeds can be packaged in the cartridge 128B as non-radioactive seeds, shipped to a licensed facility and bombarded with neutrons in a neutron oven to make them radioactive and then shipped in a shielded container to the end user.

The motor assembly 130 includes a radiation seed detector diode 129 that detects a seed and provides an indication in indicator lamp 131. The injection of a seed in the needle is accomplished by withdrawing stylet 127 to expose the chamber to the selected cartridge to cause a seed to enter the tube. The stylet is used to block the tube against further seeds and to force the seed to the tip of the needle. Seeds are prevented from falling into needle by a set of spring-loaded ball bearings on each side of seed chamber advancing the stylet deposits a seed in the tissue. The servometor 133 moves the tube downward and needle upwardly at 2 mm to 5 mm increments.

In one embodiment, the nonradioactive microspheres are intially loaded into flat round disks or cylinders such as shown at 124 but containing a plurality spring-loaded chamber that permits placement of five to fifty seeds per chamber rather than a single channel containing seeds. At the opposite end of each chamber is a perpendicular spring-loaded pin that is normally in the down or closed position, blocking the end of the seed chamber. Thus, the plate contains a total of 40 spring-loaded chambers, with 40 spring-loaded "gate pins".

Each disk contains 40 chambers, holding a total of 200 to 2,000 seeds per disk. Six disks are thus prepared. Once all 40 chambers are loaded with seeds, the disk is locked closed by attaching a second disk to it. This locking disk is designed to facilitate transfer of the seeds into a needle implantation gun, one at a time.

For this purpose, at the level of each "gate-pin" there is a chamber underneath on the locking plate. The locking plate has 40 such chambers that all converge on a central point of the plate from the level of the "gate-pins". This central point on the plate corresponds to the breech of the implantation gun, and the disk serves as a magazine holding 200 to 2,000 seeds. At the outer end of each chamber of the locking plate, there is a spring-loaded plunger that is normally in the "open" position. Once a seed is loaded into the locking plate chamber by opening and then closing the "gate-key", pushing on the locking plate plunger moves the seed centrally into the breech of the "gun barrel".

A series of "implantation needles" are placed at surgery into the patient's tumor by attaching the "gun barrel" to each interstitial needle. The seed is then advanced into an implantation needle through the "gun barrel" by advancing the gun barrel stylet. The barrel of the implantation gun is extended to permit operation of the cartridge plate approximately 10 to 20 centimeters above the level of the interstitial needles in the operative field. Each interstitial needle implanted into the human tumor tissues has a flange at the proximal end that attached to the implantation gun barrel. The gun barrel has a tissue guide that rests against the tumor bed and assists retraction of the implantation needle at 5 mm intervals. Thus operation of the implantation gun proceeds as follows:

Step 1: A disk containing 40 spring-loaded chambers containing 5 to 40 seeds per chamber, for a total of 200 to 2,000 seeds is attached to the breech of the implantation gun. The chambers are arranged in a circular fashion on the disk.

Step 2: The muzzle of the implantation gun is attached to the flange of the implantation needle arising from the patient's tumor.

Step 3: Centrally located on the seed disk are 40 buttons. These buttons operate the "gate-keys" blocking the end of each seed chamber. The "gate-keys" are normally in the locked or closed position. The seed implantation process is initiated by pulling open and then closing one "gate-key". This allows a single microsphere to drop into the locking plate away from the seed plate. Closing the "locking key" not only closes off the seed chamber, it also closes the locking plate and encases the seed in the locking plate chamber.

Step 4: Once a single seed is isolated in the locking plate chamber, the locking plate chamber plunger (normally in the "open" position) is closed. This pushes the single microsphere into the center of the locking plate, and into the "breech" of the implantation gun. A silicon diode radiation sensor at this location is activated by the radiation produced by the radioactive microsphere, and a light emitting diode signals that a seed is in the breech of the gun. Once a seed is in the breech of the gun, it is advanced downward through the barrel of the implantation gun into the attached implantation needle, and exits into the patent's tumor. The needle is then retracted 0.5 mm, and the process is repeated. This permits rapid implantation of 200 or more seeds spaced at 5 millimeter intervals into the patient's tumor.

To summarize: the "gate key" (one of forty) is first pulled open, then pushed closed. This isolates a single seed in the locking plate chamber. the locking plate plunger (one of forty) is pushed, loading a seed into the breech. This is signalled by a radiation sensor light. The implantation gun stylet (one of one) is then advanced, implanting the seed into the tumor tissue. The needle tip withdrawn 5 mm, and the process is repeated. This may be done manually, but is more efficiently done by driving the "gate key", locking plate plunger, and implantation gun stylet using computer controlled stepper motors.

In still another implantation gun design, the "gate key" is the only mechanism required to inject a microseed into the "breech" of the implantation gun. The gun consists of a central cylindrical seed cartridge such as shown at 124 consisting of a tube which is encircled by a series of tubes (not shown in FIG. 20) arranged in a parallel fashion around the central tube. The distal end of the central tube of the cylindrical seed cartridge screws into the proximal end of the implantation gun. The seed tubes are spring-loaded and contain 20 to 2,000 seeds per tube.

Ten tubes arranged around the circumference of cartridge permit 200 to 2,000 seeds to be implanted per cartridge. The proximal end of each seed tube is spring-loaded via a plunger mechanism. Once the cylindrical cartridge is screwed onto the implantation gun, the distal end of each tube comes abut the "gate key". Each seed tube thus rests upon a closed "gate key" when the cartridge is attached to the gun. The series of ten "gate keys" line the mouth of the gun, and are attached to the gun.

In this mechanism, the distal tip of the "gate key" has a flange that rests against a stop on the gun that corresponds to the outer wall of the seed tube and the length of the key beyond the flange matches the diameter of the seed tube. The distal end of the key is machined flush against the mouth of the seed implantation gun. The flange of the "gate key" is also spring-loaded against its enclosure. Thus the "gate key" is normally in the down or closed position.

In the closed position, the "gate key" blocks the opening of the seed tube. Thus, when the cartridge is attached to the gun, retracting the "gate key" opens the seed tube, allowing one seed to fall down one seed diameter. Closing the "gate key" by allowing it to fall back into its normal closed position under spring tension pushes the dropped seed into the mouth of the implantation gun, and simultaneously closes the seed tube. The breech of the implantation gun is blocked by two spring-loaded ball bearings that are normally in the closed position. The seed rests against these bearings until the implantation gun stylet is advanced forward, exerting pressure on the seed, parting the ball bearings, and allowing the seed to proceed down the barrel of the implantation gun.

A silicone diode is embedded in the wall of the implantation gun at this point, and a radioactive seed resting against the beall bearing gate will be signalled by activating the silicone diode and illuminating a light-emitting diode on the gun. The muzzle of the gun is locked to the flange of the implantation needle via a button-release mechanism. advancing the stylet pushes the seed into the needle and into the tumor tissue.

Operation of the cylindrical cartridge implantation gun consists of pulling open a "gate key" allowing the seed to drop, and allowing the gate key to snap back into the closed position which simultaneously closes the cartridge seed tube and pushes the dropped seed into the mouth of the implantation gun. Multiple seeds are prevented from dropping, because the depth of the chamber into which the seed falls exactly matches the diameter of the seed. This dimension is critical since a chamber that is either too deep or too shallow could result in seed jamming. Once ejected into the barrel of the implantation gun, the seed falls against the ball bearing gate, and activates the silicone diode detector and illuminates the LED. Advancing the gun stylet pushes the seed through the gate, into the needle, and into the tissue. The tissue holder is steadied, and the needle is withdrawn 5–10 mm, the stylet is removed, and the process is repeated.

The increasing availability of magnetic resonance imaging scanners along with technically advanced computed tomography scanners makes it feasible to implant and perform dosimetry calculations on larger numbers of radioactive seeds than could be counted or seen on conventional x-rays.

For a given tumor target volume, the larger the number the radioactive seeds implanted, the better the radiation dose homogeneity throughout the tumor volume. Thus, a 200 or 400 seed implant that delivers 20,000 cGy minimum peripheral dose to a tumor will have fewer "hot-spots" and "cold-spots" than a similiar implant delivering the same dose to the same volume but using only 20 to 50 seeds. The reason is that the dose falls off from each seed with the inverse square of the distance from the seed. Thus, seeds separated by larger distances have exponentially increasing dose fall-off.

Dose homogeneity is important because "hot-spots" or over-dosed areas can result in tissue break-down, necrosis, and permanent normal tissue damage secondary to destruction of the local blood supply. "Cold-spots" or under-dosed areas can result in diminished tumor kill and later tumor recurrences. Physically confining the radiation dose to the tumor without harming immediately adjacent tissues, and achievement of dose homogeneity throughout a tumor are two sought after goals of modern endocurietherapy.

While implantation of 200 to 400 radioactive seeds in a 5×5 cm tumor produces superior dosimetry compared to the same volume treated by 50 seeds, it is impractical to implant many large (4.5 mm×0.8 mm) cylindrical seeds. It is practical to implant hundreds of seeds one at a time, a new gun was designed that enables implantation of an entire plane of seeds at a time.

This gun design is similar to the cylindrical cartridge design above, but in this gun, an array of implantation units (approximately 20–100 units) is arranged on a grid or "implantation deck". All implantation units have female adapters for seed cartridges. All (20–100) implantation units also have individual "gate key" mechanisms that admit individual seeds into the breech of each of the (20–100) implantation units.

This gun design differs from the prior gun designs in that the 20–22 guage implantation needles (with flanges) are attached to the implantation units on the implantation grid prior to insertion of the needles into the patient's tumor. Once attached, the needle depth can he individually adjusted either upwards or downwards (shallow or deep) in relation to the implanted tumor. Once the depth is adjusted, each needle implantation is locked to the implantation deck.

The first plane of seeds is loader into each of the 49 "breech" mechanisms by retracting their gate keys. In this gun design, the gate keys are all attached in parallel array, so that one movement opens all 49 gate keys simultaneously. Even with a large number of implantation units, the needle stylet mechanism of pushing seeds from the breech through the needle into the tumor tissues may still be used.

Several different methods can also be used to drive the seeds from the breech of the implantation unit into the patient's tumor tissues:

1) A small amount of tissue-compatible liquid is injected under pressure behind the seed, driving the seed into the tissue with the liquid.

2) A small burst of tissue-compatible gas is injected under pressure behind the seed, driving it into the human tumor tissues with the gas jet.

3) An high-voltage low current electrical discharge initiated behind the seed in the breech on the implantation deck travels through a needle composed of an electrically insulating material into the electrically-grounded patient's tumor tissues. Using this apparatus, the seed can either be transported electrostaticlly, or it can be driven through the insulating needle by a traveling gas shock-wave or plasma wave-burst created by the electrical discharge from the gun deck to the patient's tumor tissues. This latter mechanism is also useful because the needle tract is cauterized by the electrical discharge, minimizing bleeding at the needle insertion sites.

4) The seed can be advanced by mechanical pushing with an array of needle stylets.

Following simultaneous implantation of an entire array of seeds into a single plane, the needles are all retracted back towards the deck at multiples of one millimeter intervals (usually 3–5 mm intervals), and the process is repeated to implant multiple planes of seeds. Each plane of seeds implanted need not be flat plane. An irregular plane can be created to conform to the tumor contour by adjusting the needle lengths at different intervals when initially securing them to the gun deck. The needle configuration is determined using a computerized "pre-plan".

In FIG. 21, there is shown a sputtering device, which in this example is a radio-frequency sputtering device 116 having a source of rf power 162 mounted adjacent to a target 164 spaced slightly from an anode 166 to cause the material deposited to be sputtered off into a vacuum chamber. The vacuum chamber is maintained in a vacuum through the vacuum conduit 168. A radionuclide gas is supplied to the vacuum chamber through a conduit 170 together with the appropriate mixture of argon gas supplied through another conduit 172 to create an atmosphere in which a radionuclide gas may be combined with the target material for application to microspheres.

To mount the microspheres for uniform coating, a levitation pan 150 contains the microspheres located generally at 174 and contiually bounces them by vibration so as to permit access to all sides for even coating. Some levitating devices are available commercially or may be constructed as described below.

In FIG. 22, there is shown an enlarged schematic view of the levitation pan 150 containing a holder for the microspheres mounted within a pan 154 and held by a cage 160. Vibrators, 156, which may be crystalls are positioned to be vibrated electronically so as to bounce the microspheres shown in 174.

In FIG. 23, there is shown another embodiment of sputtering device 160A having a cathode target 182 with the material to be coated, a high voltage potential 184, an anode 186 a levitation device and a source of radionuclide gas 188. The cathode target 182 is energized through the conductor 184 to a high potential which causes the material to be plated to be drawn to the anode 186 and coated on the charged levitated microspheres 174. The radionuclide gas 188 may be applied for combining through the conduit 188 in a proper argon gas atmosphere 172 while a vacuum is maintained in the usual manner.

In FIG. 24, there is shown another embodiment of a coating apparatus for sputtering having a vacuum chamber evacuated through the conduits 168 and 160A, an electron beam source 190, target 192, confined by a grid 194 in shutter 196, a source of high frequency rf or positive or negative high voltage 198 substrate bias and the levition pan 150.

In this embodiment, electron beams are emitted to bombard the target 192 and remove sputtered material which is attracted to the radio frequency or high frequency connection to the cage containing the microspheres 174. A radionuclide gas can be applied through the conductor 170 with an argon atmosphere maintained through the conduit 172 in the same manner as in the previous embodiments. The microspheres may be vibrated to provide an even coat from the material from the target and/or radionuclide gas.

In FIG. 25, there is shown another embodiment of coating device 160C having an arc cathode 204, anode 202, a target 208, the levitation pan 150 and a source dc or rf of bias voltage 206 maintained in a vacuum chamber from which vacuum pressure is drawn by a vacuum pump through the conduit 168. The target has coating materials spun off from it under high voltage from an arc supply 212 for drawing by means of the negative or rf bias 206 to the microspheres 174 in the levitation pan 150. Radionuclide gas can be supplied through the conduit 188 and argon gas through the conduit 172 in the manner of the other embodiments so as to coat particles.

In FIG. 26, there is shown another embodiment 160D of sputtering agent having a target 230 a source of ions 232, a controlling solinoid 234, and the levitation pan 150 in a vacuum compartment evacuated through the conduit 168. The ion source 232 generates ions which are propelled by the solinoid 234 against the target 230 to sputter off material which is drawn by a bias potential 206 to the microspheres 174 being levitated in the levitation pan 150. A radionuclide gas can be applied through the conduit 188 together with argon through the conduit 172 for incorporation of a radionuclide onto the coated material.

In FIG. 27, there is shown still another coating apparatus 160E having a tubular plasma guide 250 extending from an anode having a target 256 mounted to it about an arc cathode 258 on one end and the levition pan 150 supporting the microspheres 174 on the opposite end. Guide coils 260 maintain a field around the plasma guide duct at 250 to guide plasma to the microsphere. The conduits 188 and 172 for applying radionuclide gas and argon respectively to the microspheres communicate with the levitation pan directly. An exit solenoid 270 channels the plasma directly onto the levitated microspheres. Only "clean" charged plasma reaches the microspheres and neutral macroparticle contaminants are eliminated. The microspheres and the exit end of the plasma duct are all encased in a vacuum compartment evacuated by a vacuum turbomoleculer pump through the conduit 168.

First, if the radioactive plasma is produced from a radioactive target in a curvilinear cathodic arc deposition device as in FIG. 27, then the radioactive plasma consists of radioactive charged atoms and neutral radioactive macroparticles. The radioactive macroparticles are removed from the plasma beam by the curvilinear plasma solenoid tube.

As the radioactive plasma traverses the bend in the curved solenoid guide tube, the macroparticles are deposited upon the surface of the tube, and the charged species in the plasma follow the electromagnetic field without touching the guide tube. Thus, the radioactive charged atoms are directed by the electromagnetic field produced by a solenoid around a curved guide tube and are deposited directly onto the substrate materials. Unwanted neutral radioactive macroparticles collide with the guide tube, which then becomes contaminated and may be removed and discarded at competion of manufacture. This efficiently places the majority of the radioactive target material onto the substrates without contaminating the apparatus.

Similarly, radioactive coats can be produced using other methods for producing ionized plasma. In such other methods, the solenoid can also be used. For example, the curvilinear plasma solenoid tube can be used to direct an ionized radioactive plasma beam produced by ion beam devices or ion plating devices.

In the case of magnetron sputtering from a radioactive target, confinement of the plasma is more difficult because the plasma is composed mainly of netrual radioactive atoms that sputter from the radioactive target with a given kinetic energy. It is still possible, however, to magnetically enhance the plasma density around the substrate coating area by methods that result in some confinement of the plasma to the coating area. Confinement of the plasma to the substrate coating area increases the coating efficiency and quality and elminates deposition of radioactive materials onto unwanted parts of the coating chamber and apparatus.

There are several methods of plasma confinement for magnetron sputtering. In one method, the plasma is confined to the area of the substrate bouncing pan by placing either permanent magnets or solenoids beneath and around the bouncing pan in various configurations. Also an "unbalanced" magnetron and an unbalanced magnetron operated in the double-site-sustained discharge mode and multipolar magnetic plasma confinement may be used as described by Kadiec and Musil (J Vacuum Science Technology 8(3), May/June 1990, pp. 1318–1324).

In the preferred embodiment, a straight cylidrical superconducting solenoid cylinder is used to produce high-density electromagnetic fields to confine the radioactive plasma and direct it to the substrate bouncing pan without significantly contaminating the wall of the vacuum chamber. The bouncing pan is outfitted with high-tesla permanent neodymium magnets to enhance the plasma density near the microspheres. This plasma confinement system is used both for production of radioactive coats using radioactive target materials and when producing radioactive coats from reaction of a nonradioactive target with a radioactive reactive sputter gas.

In addition to the guide of FIG. 27, further measures are taken to provide self-cleaning. In the preferred embodiment, there are three basic elements of the self-cleaning features of the vacuum system. The first consists of a very efficient glow-discharge plasma stripping or plasma-cleaning cycle to convert the deposited solid radioactive waste back into the gaseous form. The second consists of a trap system to remove the gaseous radioactive waste and store it in a confined space. The last modification converts an open vacuum-system that exhausts to the atmosphere into a closed vacuum system that constantly recirculates more than 95% of its gases per cycle.

Because a variety of reactive radioactive gases are used in the manufacture of radioactive seeds, the vacuum coating apparatus is constructed of stainless steel and Monel metals that are designed to withstand corrosive gases. Corrosion-resistant turbomolecular pumps and seals and entire corrosion-resistant sputtering systems are commercially available.

Hydrogen gas ($H_2$) and oxygen gas ($O_2$) are used to "plasma-strip-clean" the substrate materials and to clean the radioactive contaminants from the entire vacuum chamber. Plasma strip cleaning is most efficiently done at high power plasma densities, and therefore d.c. glow charges are preferred over r.f. glow charges for this purpose.

The vacuum chamber includes a series of vertical antennae placed at equal intervals around the inner circumference of the vacuum chamber equidistance from the wall of the chamber and the substrate bouncing pan. These antennae are conncted to a −1000V, 1500 watt D.C. power supply. Following completion of the radioactive coating over microspherical substrates, a mechnical shutter closes off the bouncing pan and radioactively-coated seeds from the remainder of the vacuum chamber. The chamber is pumped down to $5\times10^{-7}$ Torr and backfilled with pure hydrogen gas at approximately 30 to 60 sccm, and the turbo pump gate valve is adjusted to 20–60 mTorr. Arcing is avoided.

The vertical antennae are energized by the D.C. power supply, igniting a hydrogen plasma. This initiates hydrogen strip cleaning, with added e chlorine in a manner known in the art. However, multiple gases are added to increase the likelihood that deposited material will combine with the stripping gas to form a gaseous compound.

After ignition of the hydrogen plasma, either 5 sccm of chlorine trifluorine gas ($ClF_3$) or 2.5 sccm of chlorine gas ($Cl_2$) or hydrogen chloride (HCl) mixed with 2.5 sccm of fluorine gas ($F_2$) or hydrogen fluoride (HF) is admitted to the vacuum chamber with a total pressure of 20–60 mTorr.

Following (hydrogen+chlorine trifluorine) or (hydrogen+chlorine+fluorine) or (hydrogen+hydrogen chloride+hydrogen fluoride) plasma strip cleaning for 10–20 minutes, the gas flow is stopped, and system is pumped down to $5\times10^{-7}$ Torr. Oxygen gas is admitted to 30–60 sccm at a pressure of 20–60 mtorr, and again the glow-discharge antennae are energized at −1000V, 1500 W d.c., igniting an oxygen plasma. Oxygen strip cleaning removes the residual chlorine and fluorine contaminants. This continues for 10 minutes, and the cleaning cycle is complete. Vacuum chamber is checked for residual radioactivity before venting the system.

During the strip cleaning process, the radioactive contaminants are converted into their corresponding gaseous forms. These gases normaly pass out of the vacuum chamber through the turbomolecular pump to the roughing pump to the exhaust vent. It is desirable to trap the radioactive products as a condensible vapor between the turbo and roughing pumps before they arrive at the exhaust vent.

To remove the radioactive products, a series of three cryogenic liquid nitrogen traps is used. As the gases pass through the traps, they are condensed and frozen with hold-times of 12–16 hours using commercially-available cryogenic liquid nitrogen traps. The frozen radioactive condensate is later transferred to a sealed container and transferred to a radioactive waste disposal site. Any remaining residual radioactive gases are removed at the exhaust port which flows into a rechargeable carbon filter before final venting to atmosphere.

Rather than continuously venting radioactive waste gases out of the vacuum system, it is desirable to recirculate them back into the coating chamber so that the residual radioactivity will remain contained within a closed-loop radioactive coating system. In addition to the exhaust gases, the discharge from the roughing pump contains oil vapor that must be removed prior to gas recirculation. This is accomplished by attaching a hermeticaly-sealed stainless steel corrosion resistant oil mist trap to the exhaust side of the roughing pump. In turn this is connected to a stainless stee gas expansion chamber and holding tank.

The gas expansion chamber has an auxiliary one-way exhaust vent to atmosphere via a carbon filtration system that cleans any residul radioactive gases from the exhaust before venting. The auxiliary vent is used only when pressure becomes excessive in the expansion chamber. After equalization, atmospheric-pressure gas to be recycled is pumped through a one-way vave into a second holding chamber where the gas is micro-filtered and mixed with argon. A gas compressor pumps waste gas mixed with argon to an absolute pressure gauge, through the mass flow meters, and back into the gas inlets of the vacuum system where it is recycled.

During radioactive sputtering from radioactive target or radioactive reactive sputter gas, exhaust gas exiting the turbo pump is condensed through a series of two or three cryogenic liquid nitrogen traps. Non-condensed gases continue though the roughing pump and exit into a closed loop consisting of an oil mist filter, a gas expansion/pressure equalization chamber, one-way pump into an argon or hydrogen mixing and filtering chamber, followed by exit to an absolute pressure valve, mass flow meters, and through the inlet lines of the vacuum chamber again. Excess gas is disposed of at the expansion chamber by venting through a rechargeable carbon filter gas cleaning system.

The sputter deposition system modifications described above can he combined into one system that is both self-cleaning and closed-loop. In this modification after radioactive coating is completed, the sputtering appartus itself is substantially radioactive due to radioactive deposits upon the chamber parts. To eliminate these deposits and prepare the system for the next manufacturing cycle, the glow discharge cycle is initiated in a pure hydrogen plasma at 20–60 mTorr by energizing the vacuum chamber antennae. Then either chlorine and fluorine or chlorine trifluorine, hydrogen fluoride and hydrogen chloride gases are admitted and hydrogen/chlorine/fluorine strip cleaning of the chamber is initiated.

The exhaust gases flow through the turbomolecular pump into the series of three cryogenic nitrogen traps, into the roughing pump and into the expansion chamber to the mixing and filtration chamber to an additional series of three carbon filters and back into the vacuum system. The radiation levels in the vacuum chambers are monitored by silicone diode radiation detector devices, and the self-clean plasma-strip continues and the gases are recycled in a closed loop until the radiation levels fall to acceptable levels and the chamber contaminants have been removed.

The radioactive waste is collected primarily in the three cyrogenic nitrogen traps as a liquified gas, and secondarily in the particulate carbon traps. These may be removed, stored, and allowed to decay, and then may be transferred to a low-level radioactive waste site. The above described self-contained and self-cleaning manufacturing apparatus would typcailiy be contained within a hazardous containment room that contains a shielded radioactive waste material storage area, an air supply to work area that vents to fume hood and environmental carbon filtration system.

In FIG. 28, there is shown another embodiment of coating apparatus 160F having the levitation apparatus 150 for bouncing spheres 174, conduits 172 and 188 plus any auxillary conduits required for introducing inert gasses and reactive gasses and radioactive gasses and seven magnetrons, three of which are shown as 350, 352 and 354 within a vacuum enclosure evacuated through a conduit 356 by turbo-molecular pump, a conduit 358 by a diffusion pump and a conduit 360 by a vacuum pump, depending on the mode of operation of the apparatus. A bias voltage may be applied to the microspheres in the levitation apparatus through an electrical connection 362.

With this arrangement, any of the seven magnatrons including 350, 352 and 354 may cause targets mounted to it to sputter off coating material which, in some instances may be combined with radionuclide gasses such as radioactive hydrides to form compounds composed of the gas and a target metal for preparing a radioactive coat. Other materials for other coats of a microsphere may be sputtered off for application to the spheres under a bias transmitted to the spheres through the conductor 362. In this embodiment, the magnatron 350 is a three inch magnatron, the magnatron 352 is an eight inch magnatron and the magnatron 354 is a six inch magnatron.

The target materials are selected in accordance with the purpose for the coat and the thickness of the coat. The larger magnatron is used for thicker coats to provide a faster coating operation. To energize reactive gasses, a 13 mega-Hertz (mHz) radio frequency excitation coil 362 is provided adjacent to the conduits 172 and 188. Each of the magnatrons 350, 352 and 354 includes a corresponding source of radio frequency power 350A, 352A and 354A, corresponding coolant 350S, 352B and 354B targets 350C, 352C and 354C and shutters for the targets 350D, 352D and 354C.

With this arrangement, the higher powered magnatrons are capable of spinning off target material from a larger surface area to provide a higher rate of reaction and thus enable the same apparatus to prepare different coats of different materials in a step by step manner.

In FIG. 29, there is shown another embodiment of coating apparatus. In FIG. 29, there is shown another embodiment 160G of coating apparatus similar to the embodiment 160F of FIG. 28 except instead of the larger magnatron, a plasma source similar to that of the embodiment of 160F is used to provide macroparticle-free plasma beams to the levitated microspheres from a cathodic arc target to provide a pure uniform coat. The device contains six magnetrons and one cathodic arc source with a curvilinear plasma tube with solenoids used to clean neutral macroparticles from the charged plasma beam.

In FIG. 30, there is shown another holding apparatus 150A for multilayered radioactive implants having a plurality of mask members 260 overwhich a fabric or ribbon 282 to which microspheres 284 are attached is mounted. The mask is mounted to a base 286 and bias voltages are applied to the microspheres through electrical connections shown at 290 and 292. A stepping motor rotates the ribbon or fabric strip to apply coats evenly to the microspheres 284 This holder may be mounted within any of the coating apparatus 160–160G instead of the levitating apparatus 150.

With this arrangement, the microspheres may be coated while on a ribbon or fabric in the manner described above either in a one-by-one manner or with a plurality of them being energized at once for coating. Different coats may be applied to different microspheres for the purpose of providing a contoured radioactive effect along the ribbon or a different locations on the fabric and the coats may be applied one by one.

Any form of deposition may be used with this apparatus and the bias may be adapted from microsphere to microsphere or by masking so as to obtain the desired effect of different amounts of radiation from different microspheres. Moreover, the radionuclide gas may be selected with a metal to form a metallic radioactive coat that contains the gaseous radionuclide introduced into the container.

In FIG. 31, there is shown still another embodiment 150B of coating apparatus for coating a wire 292. This coating apparatus provides a differential radioactivity along the length of the wire and includes a base 290, a differential bias voltage array at 294, a stepping motor 296, a digital to analog amplifier 298 and control mechanism 300 for rotating the wire from angular position to angular position for even coating. The differential bias 294 is controlled through the digital to analog convertor 298 and provides a differential bias along the wire 292. The control of a computer or other device as shown at 300. With this arrangement, since the bias is varied, the sputtered material onto the wire differs from location to location along with wire to provide pre-programmed radioactive contour. A similar arrangement holds an optical plaque or ribbon or fabric and provides a layer area differential bias to create a contoured layer of preprogrammed radioactivity by controlling the thickness of the radioactive layer from location to location.

In FIG. 32, there is shown a composite target top-plate 370 having a target of the type used in the embodiment of FIG. 28 holding plate 380, an O-ring 378, and a centrally located composite target holding plate 382. The plate 380 is circular and surrounded the O-ring 378 to permit fitting with any of the vacuum chambers of the previous embodiments to provide a target containing a plurality of target materials and suitable target sources for applying sequentially coats on multilayered elements or for aiding in the preparation of a composite target material which contains a metal compound of a nuclide gas such as a radioactive hydride gas.

To provide a plurality of target sources, the composite target plate 382 includes six sections 382A–382G each of which supports a different target and each of which is located in an angled plane to permit focusing upon a single element to be coated with multilayers. To provide sputtered material to a multilayered element being coated, each of the target plates 382A–382C includes a corresponding one of the target materials 372A–372G, sources of ions or sputtering energy such as cathodic arc sources or magnatron sources 374A–374G, and feed through conduits to support shutters for closing off certain of the target areas 376B–376G.

With this arrangement, selected sources may have the shutters closed for convenience while one other is energized to sputter off material onto an element to be coated. Alternatively, each target can be sequentially activated by vaporizing the target material with a laser beam as in laser ablation sputtering. Consequently, in each of the targets 370, there is at least one radionuclide material and one material for each of the other coats to be applied to a multilayered radioactive element or there is one metal adapted to be combined with a gaseous radioactive nuclide to form a metal-radionuclide coat within the vacuum chamber and one metal for each of the other different layers to be applied to the multilayer radioactive element.

The target having a radioactive nuclide may be formed in any of the previous apparatus for forming coats by positioning the target within the coating apparatus to receive a sputtered material and sputtering the materials metal onto it from another target. In one embodiment, a target containing a radioactive compound is formed by sputtering a metal in combination with the appropriate radioactive nuclide hydride gas to form a metal radioactive nuclide compound on the target being formed. Thus, the target being formed will contain a sputterable material which has as part of it a radioactive metal compound corresponding to the normal gaseous radioactive nuclide.

While any configuration may be prepared using this target as described in this application, a typical example is for the support 382A to include an eight inch central magnatron target of titanium 372A adapted to be energized by the magnatron 374A used to produce a thick protective coat, the support 382B to include a six inch magnatron target composed of an alloy of gadolinium, nickel, palladium and iron and used to produce magnetic coating, the support 382C to include a three inch magnatron target containing samarium bromide pressed powder as the target 372C used to produce magnetic resonance imaging coat and a three inch magnatron 374C for energizing the compound, for support plate 382D to include a tungsten target 372D used to laminate radioactive titanium iodide-125 coat or form diffusion barrier of tungsten or tungsten nitride and a three inch magnatron 374D; the support 382F to include a titanium plate target 372F used to form radioactive titanium iodide-125 by sputtering in radioactive iodine-125 gas or used to form titanium nitride laminate or diffusion barrier. A three inch magnatron 374E, the support plate 382F to contain a target of Hafnium to produce HFN colored coat and the support plate 382G to include a titanium Ti(I-125)$^2$ target and a three inch magnatron 374G to serve as the single radioactive nuclide source.

Typically, solid pressed powder targets are produced in the shape of flat pltes or disks that are ⅛" thick up to 1" thick. These are made by pressing the corresponding powder under a compression force of approximately 5–20 Newtons per square millimeter. Similar pressed power targets may be manufactured by pressing various radioactive powders. Because a limited amount of radioactivity is required for each manufacturing run, it is usually only necessary to have several milligrams of radioactive material in the target. Therefore, the targets can be pressed from their corresponding nonradioactive powders, and only the outer millimeter of the target would containe the radioactive powder.

For production of radioactive coats onto wires or sutures, a "sputter-up" configuration may be used, in which case a loose radioactive powder may simply be poured into a metal "bucket" or "boat" and then it may be directy sputtered onto the wires or suture substrates placed above the magnetron sputtergun. For coating microspheres, it is usualy necessary to coat in the sputter-down configuration over a bouncing pan.

The manufacture of radioactive microspheres involves sputter-coating of micrspheres with a magnetron sputtergun in a "sputter down" configuration. It is advantageous to directly sputter small amounts of radioactive powders from such a magnetron sputtergun, but prior art arrangements for sputtering targets have been limited to a "sputter-up" configuration when using loose powders.

In a new radioactive sputter target design, the target consists of a high atomic weight backing bucket or "boat" that serves to both shield the radioactive material and to hold the radioactive target material to be sputtered in a magnetron sputtergun. The "bucket" material sputters with the radioactive powder, forming an "alloy." The addition of a hard metal to the compound coat improves the coat quality of the otherwise soft coat.

The design employs a high-Z (high atomic number) shallow metal bucket into which the radioactive powder to be sputtered is poured. The powdered radioactive material is placed into the bucket, which is then covered with either an electroformed nickel mesh screen or a stainless steel mesh screen. Depending upon the powder grain size (5 micron grain size to 600 micron grain size), the mesh opening is between 5 microns to 200 microns. The percent open area of the screen varies depending upon the mesh opening from about 15% to about 75%. The screen is secured in place by placing a retaining ring over the screen, securing it to the bucket. A removable tungsten disk is plaed inside the retaining ring, and this serves to shield to radioactive material, allowing the target to be handled.

With the screen locked into place, target may be inverted without losing the loose radioactive powder. This is placed into the magnetron sputtergun and used to place a radioactive coating on the substrate microspheres or sutures. The central shield may he removed when ready to sputter.

For example, a 3" diameter×0.125" thick tungsten disk-shaped target is milled to produce a shallow circular cavity that has an outer diameter of 2.5"=6.35 cm=63.5 mm and inner diameter of 1.0 inches=2.54 cm=25.4 mm. The cavity is 1 mm deep. Thus, the volume of the cavity is $V_2-V_1=(3.14\times31.7\ mm\times31.7\ mm\times1\ mm)-(3.14\times12.7\ mm\times12.7mm\times1\ mm)=3155.4-506-2649$ cubic millimeters. If the density of the powder if 5 mg/cu-mm, then this volume would hold 13.2 grams of radioactive target material.

The cavity is filled with the required amount of radioactive powder which has a grain size of 25 to 50 microns. An electroformed nickel screen or a stainless steel screen three inches in diameter with a mesh opening size of 10 microns and a 26% open area is placed over the tungsten target and over the powder-filled cavity. Because of the high percentage open area, the sputtering process is not significantly impeded by the fine screen.

A second tungsten target retaining ring 0.125 inch thick hollowed out in the center to a diameter of 2.5 inches is placed over the screen, locking it into place. A 2.5 inch diameter×0.125 inch thick tungsten radiation shield disk is placed inside the retaining ring and secured with a locking mechanism. The shielded radioactive powder filled target is then placed in a "sputter-down" position in a magnetron sputtergun. When ready, the radiation shield is unlocked and removed, and the radioactive powder is sputtered in the standard fashion.

In one method of manufacturing radioactive sources, the target is composed of a non-radioactive ionic conductive isotope which is exposed to an electrical current in the present of a radioactive gas which has a higher equivalent conductivity or transport number than the corresponding non-radioactive ionic conductive isotope in the target material. A radioactive isotope with a lower atomic weight than its corresponding non-radioactive isotope is made to migrate into a heated ionic conductive target material composed of the higher atomic weight non-radioactive isotope by application of an electrical current.

This occurs because at elevated temperatures, some compounds, such as solid halids (e.g.) PbCl or CuI or AgCl, behave as ionic conductors. The heated solid material behaves like a liquid electrolytic cell. Generally, the ionic mobility through the ionic conductor is realted to the atomic weight and atomic friction which is in turn related to the atomic radius and viscosity of the medium (Strokes relationship).

The "electrochemical mobility" of ions can be calculated, and is proportional to the "equivalent conductivity" of the ion which can be measured experimentally. This phenomenon can also be expressed numerically in terms of a "transference" or "transport number" of an ion in a solid electrolyte which is defined as the fraction of the total current which that ion carries when a potential gradient is applied. The "transference numbers" of various ions may be determined experimentally using the Hittorf method (Adamson, Textbook of Physica Chemistry, Academic Press, 1973, pp. 510, 511).

If the ionic mobility or transference number of an ion in an ionic conducting compound is higher than in an adjacent material, then the ion with the higher mobility will migrate into the material with the lower mobilities when an electric current is applied.

For example, since natural iodine has an atomic weight of 127, the lighter radioactive iodine-125 would be expected to have a higher ionic mobility and a higher equivalent conductivity ($cm^2 equiv^{-1} ohm^{-1}$) than I-127. Therefore, if a commercially available electronically charged (positive charge) CuI sputter target plate is heated to approximately 250 degrees Centrigrade in the presence of a radioactive I-125 gas plasma, then the I-125 will migrate into the CuI target material, displacing the natural nonradioactive I-127. The degree to which the migration of I-125 into the CuI-127 target occurs is directly dependent upon the current density which passes through the target material. Thus, any amount of radioactivity can be deposited deeply to any desired depth into the surface of the CuI target, depending upon how long the ionic transport is allowed to proceed.

Thus, in a special argon/vacuum reaction chamber, the anode composed of a plate of non-radioactive copper iodide is energized with a positive d.c. bias voltage. A gas inlet tube is given a negative bias voltage, and radioactive (iodine-125)$_2$ gas is admitted to the system, igniting a radioactive I-125 plasma. The I-125 plasma atoms migrate spontaneously into the CuI anode, forming a radioactive surface layer of CuI-125 approximtely 4 microns thick after 10 Ci of I-125 gas is admitted into the reaction chamber. The actual activity accumulated on the CuI target is measured experimentally.

In FIGS. 33 and 34, there are shown front and side elevational views of a sputter deposition assembly 400 having a chamber 402 and a control and power assembly 404, with the chamber 402 resting on the power and control assembly 404. The control and power assembly 404 includes a moveable frame and holds within it supplies of gases and electrical power as well as control panels for controlling the operations in the chamber 402.

The chamber 402 includes a borosilicate glass cylinder 410, a top plate assembly 412, a base plate assembly 414, a wire cylinder guard 416 (FIG. 33), certain internal operational units shown generally at 418 and certain external parts. The external parts may be considered as external target supply units 420, external cylinder supply units 422, and external bouncing pan units 424. The borosilicate glass may be of the type sold under the trademark Pyrex sold by Corning Glassworks, Corning, N.Y., 14832, United States of America.

The internal operational parts 418 of the chamber include a bouncing pan assembly 430 and a target assembly 432. The bouncing pan assembly maintains the substrates separate from each other and separated from the surface of the bouncing pan during the sputtering operation while the target sputters material for their coats thereon.

The external target supply units 420 include a manual deposition shutter handle 440, a Torus inlet 422, a radio frequency tuner assembly 444, and a tuner support 446. The tuner support holds the radio frequency tuner which is electrically connected to the Torus inlet 442. The manual deposition shutter handle controls a shutter which is part of the target assembly 432 to control the sputtering of metal therethrough onto the substrates within the bouncing pan assembly 430.

To supply gases to the cylinder, the external cylinder service unit 422 includes a process gas/vent manifold 450, a convention gauge tube 454, a capacitance manometer 456, and a manometer isolation valve 458. The process gas/vent manifold supplies gases and vents gases from the internal space within the chamber while the manifolds measure the internal pressure for control purposes.

To drive the bouncing pan, the external bouncing pan units include a piezoelectric bouncing pan drive 460 which is driven from the control and power unit 404. The control and power unit 404 includes a bay frame 470 for supporting the chamber on its top surface and holding within it the manual four-line valve 470, the frequency tuner 464, the amplitude tuner 466, a turbomolecular pump 474, a manual gate valve 476, a series vacuum gauge controller 478, and certain control panels and power supplies 480 to supply electrical d.c. power. These units are conventional except insofar as they cooperate with the novel chamber and bouncing pan to supply sufficient power and frequencies thereto.

In FIG. 35, there is shown a simplified enlarged view of the chamber 402 (FIGS. 33 and 34) having the internal operational units 418, the external target supply units 420, the external cylinder service units 422, and the bouncing pan assembly 424. The internal operational units 418 include the bouncing pan assembly 430 and the target assembly 432.

To provide material for the coats, the target assembly 432 includes the Torus magnetron sputtering gun 490, the Torus target 492, the deposition shield 494, and the magnetron deposition shutter 496. The magnetron deposition switch 496 includes a coupling clamp 500, a steel rod 502, and the deposition shutter 504. With this arrangement, the substrates are confined and the sputtered material is channeled directly down onto the substrates to minimize deposition of material except on the substrates. The deposition shields 494 and shutter 504 can he removed when they become contaminated to aid in the reduction of radioactive contamination.

To levitate the substrates while they are being coated, the bouncing pan assembly 430 includes a sputter shield 510, a pan assembly 512, a pan mounting spool 514, a driver feed-through plate 514, and an electrical bias connection to the pan 518. With this arrangement, the bouncing pan is electrically biased and repels the substrates. It also aids in imparting a charge to the substrates to keep them separated while the shield 510 confines them.

The manual deposition shutter handle 440 is connected to the steel rod 502 through the coupling clamp 500 and the Torus inlet 440 goes through a flange into the chamber. The chamber is also connected to a spare port 520 and an I-bolt from carrying the chamber is attached at 522.

To provide gas and d.c. power to the chamber, the external cylinder service units 422 include the dual-gas feed through 530, a first processed gas inlet 532, a second processed gas inlet 534, and a third processed gas inlet 536 to permit gases to be introduced into the chamber at selected locations. The pumping stack 538 is mounted for evacuation and pressurization purposes and a piezoelectrical driver 490 is connected to the bouncing pan 512 by a sapphire-tipped horn 540 to vibrate the bounding pan.

In FIG. 36, there is shown a fragmentary enlarged broken-away view of the bouncing pan assembly 430 showing the piezoelectric drive 460, the variable frequency power supply 462, the source of d.c. bias 518, the feed-through flange 516, the ultrasonic horn 540, the bouncing pan 512, and the spool 514. As shown in this view, the frequency can be adjusted by control 464 and the intensity of power applied to the piezoelectric driver 460 from the control 466 to vary the power and frequency applied to the horn 512. A d.c. bias is applied through the d.c. bias 518 to the metal center of a surface-insulated pan or to the conducting surfaces of an insulated interior pan.

As best shown in the exploded enlarged sectional view of the bouncing pan 512 in FIG. 37, the bouncing pan assembly 512 includes a screen retaining ring 550, the screen 552, the bouncing pan 554. A plurality of particles 556 as shown retained between the screen 552 and the bouncing pan 554 with the bouncing pan being driven by the horn 540. The bouncing pan includes a central conductor 572 with insulating surfaces 570 and 574 so that a d.c. bias is applied to the interior metal portion of the bouncing pan through the conductor 564 and an adjacent connecting bolt. The top insulating surface 570 is coated with a thin foil conductor.

To prevent welding of substrates 556 in the bouncing pan 554, seeds 556 are prevented from momentarily collecting on the bouncing pan. Under this circumstance, vacuum-welding phenomenon does still occur, but it occurs so infrequently that less one percent of microspheres weld. This is true even when coating using metal targets that are prone to vacuum-weld such as copper. Manufacturing modifications employing alloying and reactive sputtering are known to eliminate this problem and are described hereinafter. To avoid contact of seeds with each other against the bouncing pan surface, at least one of two different mechanisms are used and preferable both are used.

Firstly, a frequency tunable drive or driver set to a frequency slightly different from the resonant frequency of the bouncing system is used. For example, a frequency in the ranges of 90 percent to 99.5 percent or 100.5 percent to 110 percent of the resonant frequency is used.

The pan 554 is driven by a relatively high power (450 watt) ultrasonic driver horn 540 at 10,000 Hertz coupled to the ceramic bouncing pan via a pyrolytic boron nitride disk. Tunining of the driver frequency slightly markedly changes the resonance and pattern of seed bounce in the pan.

The pan is coupled to flat the ultrasonic horn tip by means of tightening three flat head adjusting screws with the horn on at a low power setting. The pattern of vibration of the seeds in the pan can be observed visually, and the screws may be adjusted to produce an even bounce pattern. Then the power is increased, and the tuner is tuned to first produce a "ringing sound" at the coupling of the boron nitride disk to ultrasonic horn. Adjusting the tuner back slightly from the "ringing point" eliminates the ringing sound from the pan and produces a uniform seed bounce at the lowest power levels.

Secondly, the bouncing pan is composed of an insulating ceramic rather than solid metal, and the insulating ceramic pan contains a thin foil metal liner to produce a "capacitor effect". The entire pan is completely electrically isolated and "electrically floated" from the rest of the sputtering apparatus. In an alternate bouncing pan design, the bouncing pan is composed of a low density metal such as titanium, but the metal surface of the pan is coated with an insulating material such as silicone dioxide. This is shown in FIGS. 33–37. The insulating layer of silicone dioxide is then coated with a thin metal layer such as chromium to again produce the "capacitor effect" which results in seed repulsion away from the pan bottom. The "electrostatic" features of this pan design are most important when bouncing relatively small (less than 300 micron diameter) beads, and less important when bouncing large diameter beads (greater than 600 micron diameter).

More specifically, prior art bouncing pans have employed a "low-power" white-noise ultrasonic driver system to minimize seed damage during bouncing. Instead, the bouncing pans in the preferred embodiment include a commercially-available highly tuned single frequency high power longitudinal mechanical ultrasonic transducer, coupled to the bouncing pan by an ultrasonicator horn connecting the transducer to a pyrolytic boron nitride disc located beneath the pan. The pan is secured and leveled against the flat tip of the ultrasonicator horn using three flat-head screws. Correct tension is applied to the screws with the ultrasonic horn powered on at a low level and with the pan filled with seeds.

The bounce pattern of the seeds is observed and the tension on the bolt heads appropriately adjusted. Further adjustments are made at higher power settings by tuning the amplifier frequency (10,000 Hertz) to produce a "ringing" sound in the pan. Once the "ring" is heard, the tuner is backed down slightly to eliminate the ring, and the seeds can be observed to maximally bounce at minimun power levels.

The coupling and transducer is designed to transmit most of the ultrasonic energy (450 watts) in the axial direction with little radial or torsional motion. Tuning of the ultrasonic driver horn will bounce the microspheres at difference intensities.

Prior art ultrasonic bouncing pans have utilized random low intensity (5 watt) or "white noise" drivers. Use of wide frequency band low intensity "white-noise" bouncing pan drivers severely reduces the mecanical power transmitted to the pan. These pans were designed as such with low power drivers to avoid breakage of the microspherical substrates as they hit the pan. In the present invention, high ultrasonic bouncing power levels do not result in coat breakage due to the pan design and because the seeds are deccelerated and cushioned as they approach the pan by the electrostatic repulsion forces described below.

A sputter-coated metal foil lining the electrically isolated and insulating ceramic bouncing pan acts like a capacitor and constantly collects and maintains a high surface electrical charge on the pan. This surface charge strongly repels all approaching like-charged microspherical substrate beads as they near the pan during the sputtering process, resulting in increased seed ejection away from the pan. This surface electrostatice repulsion facilitates seed ejection away from the pan, preventing seed substrates from remaining in contact with each other on the pan surface. This largely eliminates the head-sticking and vacuum-welding problems commonly encountered with solid metal bouncing pan designs, and permits coating of microbeads with pure soft metals like copper without a vacuum welding problem.

In solid bouncing pan designs, although the pan itself may be given a large negative D.C. bias, becuase of the heavy metal mass of the pan, there is not enough surface electrostatis charge to repel the like-charged seeds away to any significant degree. Thus, an insulating ceramic/thin metal foil bouncing pan design that maintains a strong electrostatic surface charge that effectively electrostatically repels approaching like-charged microspheres is used. The other critical factor is the design that incorporated a pyrolytic boron nitride coupling of the bouncing pan to a high power (450 watt) fixed frequency (10,000 Hertz) ultrasonic horn. The delivery of high ultrasonic power levels to the microspheres keeps the microspheres from resting on the pan surface where thay can vacuum-weld.

The local electric surface field created by the ceramic/metal foil pan repels beads away from the surface of the pan, ejecting them back up into the plasma. This also results in a reducting of mechanical force required to bounce the seeds off the pan.

The local electric surface field also serves to cushion and decelerate the beads as they approach the pan, resulting in less mechanical breakage. With this ceramic/metal foil bouncing pan system, whether the pan is electrically biased or neutral, it is not necessary to add an electronegative gas to prevent seed sticking. This has always been required in other prior art systems with solid metal pan designs. Even the neutral unbiased pan retains a surface charge, resulting in seed repulsion.

In another bouncing pan design, the bouncing pan is composed of a lightweight metal such as titanium. The metal pan is again electrically "floated" or isolated. The metal is of a lightweight type to allow a larger load to be bounced, since the ultrasonic driver can only drive a limited weight which includes the weight of the pan itself plus the weight of the substrate material. The titanium pan is then sputter-coated with an insulating coat such as silicone dioxide. A sufficient coat thickness is applied at required to completely electrically insulate the titanium pan. The silicone dioxide coat is then coated with a thin layer of metal such as titanium or tungsten. This titanium pan/silicone dioxide/titanium coating produces the "capacitor effect" described above, and results in repulsion of seeds away from the bouncing pan during plasma sputter-coating by the same mechanism disclosed above. The pan is coupled to an ultrasonicator horn via a pyrolytic boron nitride disc.

The electrostatic forces play a larger part when coating microspherical substrates approximately 200 to 400 microns in diameter. Lower power levels were required to bounce smaller microspherical substrates. For larger microspherical substrates 600 microns or more in diameter, higher ultrasonic power levels are required to levitate the seeds, but electrostatic repulsion still plays a role in decelerating the seeds as they approach the pan, reducing seed breakage. Thus, coupling to a high-power (450 watt) longitudinal mechanical single-frequency tuned transducer that transmits power efficiently in the axial direction to the bouncing pan is an advantage when large diameter (600 microns) microspherical substrate seeds are levitated. Even whith an efficient ocupling, Power levels less than 50 watts did not levitate the 600 micron seeds sufficiently away from the pan to prevent vacuum-welding.

The metal is coated at a low pressure in the presence of a large negative D.C. bias voltage in a manner known in the art in a magnetically-enhanced plasma utilizing an rf sputter gun to obtain metal coats that are free of cracks, fissures, or other surface defects. The coatings produced are type "T" coatings (Thronton's transitiion zone). These are characterically smooth, dense, and free of columns and large grains and are intermediate between a compressive and a tensile microstructure. A more compressive type of coat is produced by decreasing the working pressure.

The quality of the sputter coats over multilayerd radioactive microspheres or microfilaments can be modified as desired by changing the deposition parameters such as sputter gas pressure, substrate bias voltage, plasma density, substrate temperature, power density, and coating rate. Coat quality is also affected by substrate size and shape, and final coating thickness.

To obtain broad zone-l-zone-2 transition regions of densely packed fibrous grains, the argon pressure is set between 1 to 5 microns or milliTorr with a $T/T_m$ of 0.10 to 0.30. At a higher $T/T_m$ in the range of 0.4–0.5, similar coats can be produced at argon pressures of 10 to 20 mTorr.

The preferred r.f. sputter-coating parameters for manufacture of multilayered radioactive microspheres and microfilaments of the present invention generally include the following (although settings may be optimized for particular elements).

The conditions in one embodiment for providing pure metal coat over microspherical substrates are: (1) base pressure equal to $0.5 \times 10^{-7}$; (2) argon pressure equal to 0.5 to 5.0 mTorr; (3) substrate bias voltage equal to −1000.0 volts, 35 watts; (4) plasma density enhanced magnetically; (5) magnetron power equal to 0.150–0.60 kW; (6) a bouncing pan that is an insulated biased thin foil "capacitor pan"; (7) bouncing pan power equal to 450 watts, 10 kHz, tunable; and (8) its bouncing pan coupling being pyrolytic boron nitride. For a compound reactive metal coating over microspherical substrates, the conditions are: (1) base pressure equal to $0.5 \times 10^{-7}$ Torr; (2) argon pressure equal to 5.0–10.0 mTorr; (3) substrate bia voltage equal to −1000.0 volts, 35 watts; (4) plasma density sufficient to enhance magnetically; (5) magnetron power equal to 0.150–0.60 kW; (6) bouncing pan that is an insulated biased thin foil "capacitor pan"; (7) bouncing pan power equal to 450 watts, 10 kHz, tunable; and (8) bouncing pan coupling being pyrolytic boron nitride.

The radioactive single seed design of this invention has several advantages such as: (1) it is smaller than prior art radioactive seeds and is spherical thus permitting a wider range of uses and easier use with less traumatic insertion into human tissues; (2) it is stronger and has high structural integrity and is thus safer; (3) it is symmetrical and spherical and uniform and thus produces a symmetrical and spherical radiation field as shown by symmetrical dosimetry; (4) it may be constructed using a wide variety of isotopes of differing energies and half-lives selected for specific applications, thus permitting optimization of the radiobiology of the type of cancer being treated; (5) it is inexpensive; and (6) in clinical practice, it permits safe delivery of radiation tumor doses that are two to five times higher than that achieved with external beam irradiation; (7) the different multilayered radioactive microspheres can be identified by their different imaging contrast agent coats or center substrate and (8) dose-rate control for purposes of radiosensitization is easily accomplished incorporating a variety of over 220 radionuclides of various half live energies and activities.

In use, the microspheres have several advantages such as: (1) an effective modality for treatment is provided by combining a relatively low continuous dose of radiation by multilayer radioactive microspheres implanted in a tumor at any anatomic location and which serve as radiosensitizers so that a short fractionated conventional course of external-beam radiation therapy is much more effective; (2) radiation dose localization is improved beyond that achievable with the low energy permanent gamma-ray seeds by use of an electron-producing seed because electron dosimetry is more localized than X-ray dosimetry; (3) different types of multilayered radioactive microspheres with different half-lives and photon or electron energies can be implanted into a tumor in the same operation to optimize tumor therapy; (4) the use of permanent implantation of short-lived seeds rather than temporary-removable implants eliminate exposed tubes which penetrate the skin surface and serve as a route for infection over many days; and (5) microspheres can be implanted into tissues using thin-gauge needles reducing risk.

There are also advantages from the composite designs that can be produced using the spheres, such as for example: (1) ribbons and a tissue-compatible fabric containing seeds useful for rapid surgical implantation may be produced; (2) the thin ribbon design containing multiple seeds allows rapid implantation of multiple seeds using a hollow interstitial needle; (3) a tissue-compatible surgical fabric containing multiple radioactive seeds allows rapid intraoperative implantation of a sheet of evently spaced radioactive seeds; and (4) the various surgical procedures and devices used for implantation of radioactive seeds provide better adaptability to a patient's needs.

There are also advantages from a wire multilayered radioactive design such as: (1) it may be cut up into pieces and placed into afterloading catheters or into nylon or polyethylene ribbons for temporary removable implants or placed inside appropriate containers to construct various intracavitary sources; (2) it has the advantages of being flexible or remain as a long needle, with or without an added sleeve for temporary implanting.

When encapsulated: (1) the multilayered radioactive microspheres or wires simplify intracavitary therapy because smaller intracavitary capsules can be constructed using multiple small-diameter seeds of the present invention; (2) a wide variety of radionuclides with energies varying from very low to very high can be incorporated into composite intracavitary sources by sealing multiple multilayered radioactive microspheres of one or several types into an appropriate container; (3) use of low energy intracavitary sources composed of low energy multilayered radioactive microspheres or wires allow selective shielding of adjacent vital structures such as rectum and bladder using relatively thin high atomic weight foils placed over the intracavitary sources or source holders.

There are also several advantages related to manufacturing the radioactive implants such as: (1) it permits mass production of a variety of designs without need of assembly of separate (radioactive) parts; (2) changes in seed composition may be made easily; (3) it permits customized manufacture of multilayered radioactive microspheres, multilayered radioactive wires, ribbon-multilayered radioactive microspheres or ocular plaques optimized for individual tumor types; (4) manufacture of a new models of multilayered radioactive microspheres, multilayered radioactive wires and ribbon-multilayered radioactive microspheres can be accomplished as needed by changing deposition parameters the type, thickness, and layering of deposited elements using the same deposition equipment; (5) it permits construction of seeds containing many optional different types of laminated materials such as imaging contrast agents, colored seed identification markers, or supplemental protective outer layers; (6) use of the high energy processes of sputtering, laser ablation vacuum deposition, ion-beam sputtering, cathodic arc or curvilinear cathodic arc plasma deposition, reactive deposition, and ion plating increase the hardness of metals coated in this manner compared to the bulk materials; and (7) the controlled variable deposition of radioactive material per unit length or per unit surface area permits customized manufacture of brachytherapy sources to exactly match the requirements of 3-dimensional computerized brachytherapy treatment plan.

The ability to provide a variety of half-lives and intensities of implants has several advantages, such as for example: (1) the smaller permanent seeds permit implantation of a greater number of seeds in more body sites using thinner needles with less risk of complication; (2) a combination of short-acting high-energy and long-acting low energy seeds can be implanted in the same procedure; (3) under some circumstances repeated implantation of seeds with short half-lives may be used instead of repeated temporary removable implant procedures thus reducing the risk of infection associated with temporary removable implants; (4) high energy short-lived seeds provide results equivalent to a temporary removable implant, but they may be applied to sites not accessible to temporary removable implantation; (5) short-lived seeds may be implanted as a "tumor-boost", replacing and improving upon a "tumor-boost" delivered by means of external-beam radiation thearpy; (6) with a wide variety of seeds available, many cancers can be more effectivley managed by brachytherapy alone; (7) a wide variety of radionuclides with energies varying from very low to very high can he incorporated into composite intracavitary sources by sealing multiple multilayered radioactive microspheres of one or several types into an appropriate container; (8) use of low energy intracavitary sources composed of low energy multilayered radioactive microspheres allow selective shielding of adjacent vital structures such as rectum and bladder using relatively thin high atomic weight foils placed over the intracavitary sources or source holders.

The ribbons, wire, plaques and fabric of this invention have the advantages of: (1) multiple multilayered radioactive microspheres provided on a m single ribbon allow multiple multilayered radioactive microspheres to be implanted at once by a thin gauge hollow needle by pushing the multilayer radioactive microsphere ribbon out of the tissue-embedded needle with a stylet while withdrawing the needle; (2) the ribbon-multilayered radioactive microspheres of the present invention may be implanted by a very thin 21 or 22 -gauge needle; (3) the fabric of this invention self-adheres to the tissues over which it is placed and may he either tissue-absorbable or non-tissue absorbable; (4) the use a fabric containing multiple multilayered radioactive microspheres or microsphere ribbons allows rapid surgical implantation of multiple seeds without need of interstitial needles or a seed gun; and (5) very thin plaques such as optical plaques can be contoured have the appropriate strength and appropriate intensity for effective treatment.

Although a preferred embodiment of the invention has been described with some particularity, many modifications and variations may be made without deviating from the invention. Accordingly, it is to be understood that within the scope of the appended claims, the invention can be practiced other than as expressly described.

What is claimed is:

1. A one-piece substantially spherical seamless multilayered radioactive seed, comprising:

a microsphere including a central sphere and a layer section with no substantial voids between the central sphere and the layer section;

said layer section including at least two layers concentric with the central sphere; said layer section being in intimate contact with the outer surface of the central sphere;

said microsphere enclosing first material having a therapeutic amount of radioactivity and an outside diameter no greater than 1 millimeter;

at least a first layer of said two layers enclosing said first material and containing a second material that reacts chemically with said first material; and at least a second layer containing a third material that forms a diffusion barrier to said first material.

2. A one-piece substantially spherical seamless multilayered radioactive seed according to claim 1 in which said layer section includes a spherical diffusion barrier layer, a third spherical layer designed to enhance diagnositc imaging and a fourth spherical protective layer enclosing at least the the first, second and third layers of said layer section.

3. A one-piece substantially spherical seamless multilayered radioactive seed, comprising:

a microsphere including a central sphere and a layer section with no substantial voids between the central sphere and the layer section;

said layer section including at least one layer concentric with the central sphere and in intimate contact with the outer surface of the central sphere;

said microsphere enclosing first material having a therapeutic amount of radioactivity and an outside diameter no greater than 1 millimeter;

said at least one layer including a radionuclide with a weighted average gamma energy of less than 100 KeV, and with a half-life of less than 130 days, wherein the multilayer radioactive microsphere is a low energy permanent multilayered radioactive microsphere for permanent interstitial implantation into human tumor tissues.

4. A one-piece substantially spherical seamless multilayered radioactive seed, comprising:

a microsphere including a central sphere and a layer section with no substantial voids between the central sphere and the layer section;

said layer section including at least one layer concentric with the central sphere and in intimate contact with the outer surface of the central sphere;

said microsphere enclosing first material having a therapeutic amount of radioactivity and an outside diameter no greater than 1 millimeter;

a radionuclide with a weighted average gamma energy greater than or equal to 100 KeV and with a half-life of less than 15 to 20 days, wherein the one-piece substantially spherical seamless multilayered radioactive seed is a high energy permanent multilayered radioactive microsphere for permanent interstitial implantation into human tumor tissues.

5. A one-piece substantially spherical seamless multilayered radioactive seed, comprising:

a microsphere including a central sphere and a layer section with no substantial voids between the central sphere and the layer section;

said layer section including at least one layer concentric with the central sphere and in intimate contact with the outer surface of the central sphere;

said microsphere enclosing first material having a therapeutic amount of radioactivity and an outside diameter no greater than 1 millimeter;

at least one of said layers including a radionuclide with a weighted average gamma energy greater than or equal to 100 KeV and with a half-life of less than 15 to 20 days, wherein the one-piece substantially spherical seamless multilayered radioactive seed is a high energy permanent multilayered radioactive microsphere for permanent interstitial implanatation into human tumor tissues.

6. A ribbon-multilayer radioactive unit having a plurality of substrate radioactive microspheres with outer diameters between 0.04 and 0.8 millimeters attached to a ribbon; a first material in said unit being radioactive; at least one layer of a second material enclosing said first material; said second material being a type that reacts with said first material; and a third material enclosing said first material and forming a diffusion barrier.

7. A ribbon-multilayer radioactive unit according to claim 6, in which both the ribbon and the substrate microspheres have an outer coat of the same material.

8. A multilayered seamless radioactive wire, comprising:

a central wire section and a layer section;

said layer section including at least one layer coaxial with the central wire section and in intimate contact with the outer surface of the central wire section;

said wire having a therapeutic amount of radioactivity and an outside diameter no greater than 1 millimeter; a first material in said layer section being radioactive; at least one layer of a second material enclosing said second material; said second material being a type that reacts with said first material; and a third material enclosing said first material and forming a diffusion barrier.

9. A one-piece seamless multilayered radioactive ocular applicator, comprising:

a substrate section and a layer section;

said layer section including at least one layer in intimate contact with a surface of the substrate section;

said applicator having a therapeutic amount of radioactivity in which radioactive multilayers in the layer section having a thickness no greater than 0.5 millimeters; a first material in said unit being radioactive; at least one layer of a second material enclosing said first material; said second material being a type that reacts with saif first material; and a third material enclosing said first material and forming a diffusion barrier.

10. A radioactive applicator comprising:

surgical fabric containing multiple evenly-spaced multilayer radioactive microspheres; each of said microspheres being a one-piece substantially spherical seamless multilayered radioactive seed having a central sphere and a layer section;

said layer section including at least one layer concentric with the central sphere and in intimate contact with the outer surface of the central sphere;

said microsphere having a therapeutic amount of radioactivity and an outside diameter no greater than 1 millimeter; a first material in said unit being radioactive; at least one layer of a second material enclosing said first material; said second material being a type that reacts with saif first material; and a third material enclosing said first material and forming a diffusion barrier.

11. A radioactive applicator according to claim 10, in which said surgical fabric is tissue absorbable.

12. A ribbon-multilayer radioactive unit comprising:

a ribbon;

a plurality of substrate radioactive microspheres with outer diameters between 0.04 and 0.8 millimeters attached to said ribbon;

said microspheres including a selected one of a radionuclide with a weighted average gamma energy of less than 100 KeV and a half-life of less than 130 days; and a radionuclide with a weighted average gamma energy greater than or equal to 100 KeV and a half-life of less than 15 to 20 days.

13. A multilayered seamless radioactive wire, comprising:

a central wire section and a layer section;

said layer section including at least one layer coaxial with the central wire section and in intimate contact with the outer surface of the central wire section;

said wire having a therapeutic amount of radioactivity and an outside diameter no greater than 1 millimeter;

including a radionuclide with a weighted average gamma energy of less than 100 KeV, and with a half-life of less than 130 days, wherein includes the a low energy permanent radioactive material for permanent interstitial implantation into human tumor tissues;

including a radionuclide with a weighted average gamma energy greater than or equal to 100 KeV and with a half-life of less than 15 to 20 days, wherein the includes a high energy permanent radioactive material for permanent interstitial. implanatation into human tumor tissues.

14. A one-piece seamless multilayered radioactive ocular applicator, comprising:

a substrate section and a layer section;

said layer section including at least one layer in intimate contact with a surface of the substrate section;

said applicator having a therapeutic amount of radioactivity in which radioactive multilayers in the layer section having a thickness no greater than 0.5 millimeters;

including a radionuclide with a weighted average gamma energy of less than 100 KeV, and with a half-life of less than 130 days, wherein includes the a low energy permanent radioactive material for permanent interstitial implantation into human tumor tissues;

including a radionuclide with a weighted average gamma energy greater than or equal to 100 KeV and with a half-life of less than 15 to 20 days, wherein the includes a high energy permanent radioactive material for permanent interstitial implanatation into human tumor tissues.

15. A radioactive applicator comprising;

surgical fabric containing multiple evenly-spaced multilayer radioactive microspheres; each of said microspheres being a one-piece substantially spherical seamless multilayered radioactive seed having a central sphere and a layer section;

said layer section including at least one layer concentric with the central sphere and in intimate contact with the outer surface of the central sphere;

said microsphere having a therapeutic amount of radioactivity and an outside diameter no greater than 1 millimeter;

including a radionuclide with a weighted average gamma energy of less than 100 KeV, and with a half-life of less than 130 days, wherein includes the a low energy permanent radioactive material for permanent interstitial implantation into human tumor tissues;

including a radionuclide with a weighted average gamma energy greater than or equal to 100 KeV and with a half-life of less than 15 to 20 days, wherein the includes a high energy permanent radioactive material for permanent interstitial implanatation into human tumor tissues.

16. A radioactive applicator according to claim 15, in which said surgical fabric is tissue absorbable.

* * * * *